US009944967B2

(12) United States Patent
Chang et al.

(10) Patent No.: US 9,944,967 B2
(45) Date of Patent: Apr. 17, 2018

(54) METHODS FOR THE SITE-SELECTIVE INTRODUCTION OF HALOGEN INTO NATURAL PRODUCTS

(71) Applicant: THE REGENTS OF THE UNIVERSITY OF CALIFORNIA, Oakland, CA (US)

(72) Inventors: Michelle C. Y. Chang, Berkeley, CA (US); Mark C. Walker, Berkeley, CA (US); Benjamin W. Thuronyi, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/913,601

(22) PCT Filed: Aug. 20, 2014

(86) PCT No.: PCT/US2014/051894
§ 371 (c)(1),
(2) Date: Feb. 22, 2016

(87) PCT Pub. No.: WO2015/026944
PCT Pub. Date: Feb. 26, 2015

(65) Prior Publication Data
US 2016/0201095 A1    Jul. 14, 2016

Related U.S. Application Data

(60) Provisional application No. 61/868,494, filed on Aug. 21, 2013.

(51) Int. Cl.
*C12P 19/62* (2006.01)
*C07D 309/32* (2006.01)
*C12N 9/10* (2006.01)
*C12P 7/62* (2006.01)

(52) U.S. Cl.
CPC ............ *C12P 19/62* (2013.01); *C07D 309/32* (2013.01); *C12N 9/1025* (2013.01); *C12P 7/62* (2013.01)

(58) Field of Classification Search
CPC ...................................................... C12P 19/62
USPC ........................................................ 549/292
See application file for complete search history.

(56) References Cited

U.S. PATENT DOCUMENTS 6,939,691 B1    9/2005 Khosla et al.

FOREIGN PATENT DOCUMENTS

WO    WO 2012/089349    7/2012

OTHER PUBLICATIONS

Akoka, S., et al., *Anal. Chem.*, 71:2554-2557 (1999).
Aparicio, et al., *Gene* 169:9-16 (1996).
Atsumi, et al., *Nature* 451, 86-89 (2008).
August et al., *Chemistry & Biology*, 5: 69-79 (1998).
Ball, et al., *J. Am. Chem. Soc.*, 131:3796-3797 (2009).
Baltz, *Trends Microbiol.* 6:76-83 (1998).
Bégué, et al., *J. Fluorine Chem.*, 127:992-1012 (2006).
Bennett, et al., *Nat. Chem. Biol.*, 5:593-599 (2009).
Bond-Watts, B.B., et al., *Nat. Chem. Biol.*, 7:222-227 (2011).
Bonnett, et al., *Chem. Biol.*, 18:1075-1081 (2011).
Brown, et al., *J. Gen. Microbiol.*, 102:327-336 (1977).
Cane, D.E., et al., *J. Am. Chem.*, 115:527-535 (1993).
Cane, et al., *Science* 282:63-68 (1998).
Chan, et al., *Nat. Prod. Rep.*, 26:90-114 (2009).
Cortes, et al., *Nature* 348:176-8 (1990).
Croteau, et al., in Biochemistry and molecular biology of plants, R. B. Buchanan, W. Gruissem, R. Jones, Eds. pp. 1250-1318 (ASPB, Rockville, MD, 2000).
Dalbie-McFarland et al. *Proc Natl Aced Sci USA* 79:6409 (1982).
Dong, et al., *Nature*, 427:561-565 (2004).
Donadio, et al., *Science* 252:675-79 (1991).
Eustaquio, et al., *J. Nat. Prod.*, 73:378-382 (2010).
Furuya, et al., *Nature*, 473:470-477 (2011).
Funa, N., et al., *Nature*, 400:897-899 (1999).
Geisselsoder et al. *BioTechniques* 5:786 (1987).
Gibson, D.G., et al., *Nat. Methods*, 6:343-345 (2009).
Gokhale, R.S., et al., *Science*, 284:482-485 (1999).
Goss, et al., *ChemBioChem*, 11:698-702 (2010).
Haller, et al., *Biochemistry*, 39:4622-4629 (2000).
Hinterding, K., et al., *Tetrahedron lett.*, 42:8463-8465 (2001).
Hu, et al., *Mol. Microbiol.* 14:163-72 (1994).
Hutchinson, *Curr Opin Microbiol.* 1:319-329 (1998).
Huang, F., et al., *Chem. Biol.*, 13:475-484 (2006).
Hughes, et al., *Chem. Biol.*, 18:165-176 (2011).
Izumikawa, M., et al., *J. Ind. Microbiol. Biot.*, 30:510-515 (2003).
Kakavas, et al., *J. Bacteriol.* 179:7515-22 (1997).
Kao, et al., *Science* 265:509 (1994).
Khosla, et al., *Annu. Rev. Biochem.*, 76:195-221 (2007).
Koryakina, et al., *Org. Biomol. Chem.*, 4449-4458 (2013).
Kuhstoss et al., *Gene* 183:231-36 (1996).
Kumar, et al., *J. Am. Chem. Soc.*, 125:14307-14312 (2003).
Kunkel, T. A., *Proc Natl Acad Sci USA* 82:448 (1985).
Lee, et al., *Science*, 334:639-642 (2011).
Liou, et al., *Biochemistry*, 42:200-207 (2002).

(Continued)

*Primary Examiner* — Taofiq A Solola
(74) *Attorney, Agent, or Firm* — Morgan, Lewis & Bockius LLP; Jeffry S. Mann

(57) ABSTRACT

Organohalides (e.g., organofluorides) represent a rapidly expanding proportion of molecules used in pharmaceuticals, diagnostics, agrochemicals, and materials. The present invention exploits the naturally occurring acetate condensation pathway as a means of introducing halogenated building blocks into natural product scaffolds. In an exemplary embodiment, the invention provides a pathway involving at least one polyketide synthase system and utilizes haloacetate or a haloacetate synthon (e.g., halomalonate) to incorporate an organohalide into the polyketide backbone in vitro. In an exemplary embodiment, the invention provides an analogous method for site-selective introduction of haloacetate or a synthon into polyketide products in vivo. The present invention expands the scope of existing chemical methods for producing halogenated natural product scaffolds such as complex halogenated natural products.

19 Claims, 58 Drawing Sheets

(56) References Cited

OTHER PUBLICATIONS

Llano-Sotelo, et al., *Antimicrob. Agents Chemother*, 54:4961-4970 (2010).
Luo, G., et al., *Bioorg. Med. Chem.*, 4:995-999 (1996).
McDaniel, et al., *Proc. Natl. Acad. Sci. U.S.A.*, 96:1846-1851 (1999).
MacNeil, et al., Industrial Microorganisms: Basic and Applied Molecular Genetics, Baltz, Hegeman, & Skatrud, eds. (ASM), pp. 245-256 (1993).
MacNeil, et al., *Gene* 115: 119-25 (1992).
Mo, et al., *J. Am. Chem. Soc.*, 133:976-985 (2010).
Motamedi, et al., *Eur. J. Biochem.* 244:74-80 (1997).
Motamedi, et al., *Eur. J. Biochem.* 256:528-34 (1998).
Müller, et al., *Science*, 317:1881-1886 (2007).
Nielsen, et al., *Biochem.* 30:5789-96 (1991).
O'Hagan, *Chem. Soc. Rev.* 37:308-319 (2008).
O'Hagan, *J. Fluorine Chem.*, 127:1479-1483 (2006).
Olano, et al. *Mol. Gen. Genet.* 259:299-308 (1998).
Omura, et al., *Proc. Natl. Acad. Sci. USA* 98:12215-12220 (2001).
Pfeifer, B.A., et al., *Science* 291:1790-1792 (2001).
Powers, et al., *Chem. Rev.*, 102:4639-4750 (2002).
Rauniyar, et al., *Science*, 334:1681-1684 (2011).
Reid et al., *Microbiology*, 141(6): pp. 1385-1393 (1995).
Rivkin, et al., *Org. Lett.*, 4:4081-4084 (2002).
Ro, et al., *Nature*, 440: 940-943 (2006).
Rouillard, J.M., et al., *Nucleic Acids Res*. 32:W176-W180 (2004).
Runguphan, et al., *Proc. Natl. Acad. Sci. U.S.A.*, 106:13673-13678 (2009).
Schupp, et al., *J. Bacteriology* 177: 3673-79 (1995).
Schwecke, et al., *Proc. Natl. Acad. Sci. USA* 92:7839-43 (1995).
Siskos, et al., *Chem. Biol.*, 12:1145-1153 (2005).
Staunton, et al., *Nat. Prod. Rep.* 18, 380-416 (2001).
Sundermann, et al., *ACS Chem. Biol.*, 8:443-450 (2012).
Swan, et al. *Mol. Gen. Genet.* 242:358-62 (1994).
Theodorou, V., et al., *Tetraherdon Lett.*, 48:8230-8233 (2007).
Tsuji, et al., *Biochemistry*, 40:2326-2331 (2001).
Walker et al., *Science*, 341: 1089-1094 (2013).
Watson et al., *Science*, 325:1661-1664 (2009).
Weeks, et al., *Biochemistry* 50, 5404-5418 (2011).
Weissman, et al., *Chembiochem* 5:116 (2004).
Wong, F.T., et al., *Biochemistry*, 49:95-102 (2010).
Wong, et al., *Biochemistry*, 50:6539-6548 (2011).
Wu, et al., *J. Am. Chem. Soc.*, 122:4847-4852 (2000).
Xue, et al., Gene 245:203-211 (2000).
Yuzawa et al., *Curr Opin Biotechnol.*, 23 (5): 727-735 (2012).
Zoller and Smith, Methods Enzymol. 100:468 (1983).

B

| | R = | $k_{cat}$ (s$^{-1}$) | $K_M$ (μM) | $k_{cat}/K_M$ (M$^{-1}$s$^{-1}$) |
|---|---|---|---|---|
| Malonate | H | 11.8 ± 0.3 | 71 ± 5 | (1.7 ± 0.1) x 10$^5$ |
| Methylmalonate | CH$_3$ | 1.49 ± 0.02 | 38 ± 2 | (3.9 ± 0.2) x 10$^4$ |
| Fluoromalonate | F | 0.29 ± 0.01 | 550 ± 40 | (5.3 ± 0.4) x 10$^2$ |

|  |  | $k_{cat}$ (s$^{-1}$) | $K_M$ (μM) | $k_{cat}/K_M$ (M$^{-1}$s$^{-1}$) |
|---|---|---|---|---|
| AckA | Acetate | (1.34 ± 0.03) × 10$^3$ | (2.7 ± 0.2) × 10$^4$ | (5.0 ± 0.4) × 10$^4$ |
|  | Fluoroacetate | 6.7 ± 0.2 | (3.3 ± 0.4) × 10$^4$ | (2.0 ± 0.3) × 10$^2$ |
| Pta | Acetyl-CoA | 37 ± 1 | 160 ± 20 | (2.3 ± 0.3) × 10$^5$ |
|  | Fluoroacetyl-CoA | 430 ± 20 | 160 ± 30 | (2.7 ± 0.5) × 10$^6$ |

| | |
|---|---|
| 1 | Malonyl-CoA |
| 2 | Malonyl-CoA, acetyl-CoA |
| 3 | Acetyl-CoA, ACCase, ATP |
| 4 | Malonyl-CoA, ACCase, ATP |
| 5 | Malonyl-CoA, MatB, malonate, ATP, myokinase |
| 6 | Acetyl-CoA, AckA/PTA, ACCase, ATP |
| 7 | Acetyl-CoA, AckA/PTA, ACCase, ATP, 1 eq acetate |
| 8 | Acetyl-CoA, AckA/PTA, ACCase, ATP, 2 eq acetate |
| 9 | Acetyl-CoA, AckA/PTA, ACCase, ATP, 20 eq acetate |

A

Keto 2S     Keto 2R

SEQUENCE LISTING

```
<160> NUMBER OF SEQ ID NOS: 78

<210> SEQ ID NO 1
<211> LENGTH: 21
<212> TYPE: DNA
<213> ORGANISM: Artificial Sequence
<220> FEATURE:
<223> OTHER INFORMATION: nphT7 R1

<400> SEQUENCE: 1
aaacgaacgt cggtcatggt g                                              21

<210> SEQ ID NO 2
<211> LENGTH: 40
<212> TYPE: DNA
<213> ORGANISM: Artificial Sequence
<220> FEATURE:
<223> OTHER INFORMATION: nphT7 F1
```

<400> SEQUENCE: 2
caccatgacc gacgttcgtt ttcgtatcat tggcacgggt            40

<210> SEQ ID NO 3
<211> LENGTH: 35
<212> TYPE: DNA
<213> ORGANISM: Artificial Sequence
<220> FEATURE:
<223> OTHER INFORMATION: nphT7 R2

<400> SEQUENCE: 3
gctccggcac gtacgcaccc gtgccaatga tacga                 35

<210> SEQ ID NO 4
<211> LENGTH: 38
<212> TYPE: DNA
<213> ORGANISM: Artificial Sequence
<220> FEATURE:
<223> OTHER INFORMATION: nphT7 F2

<400> SEQUENCE: 4
gcgtacgtgc cggagcgtat tgtgtccaac gacgaggt              38

<210> SEQ ID NO 5
<211> LENGTH: 38
<212> TYPE: DNA
<213> ORGANISM: Artificial Sequence
<220> FEATURE:
<223> OTHER INFORMATION: nphT7 R3

<400> SEQUENCE: 5
accagccggc gcacccacct cgtcgttgga cacaatac              38

<210> SEQ ID NO 6
<211> LENGTH: 40
<212> TYPE: DNA
<213> ORGANISM: Artificial Sequence
<220> FEATURE:
<223> OTHER INFORMATION: nphT7 F3

<400> SEQUENCE: 6
gggtgcgccg gctggtgttg atgatgactg gattacccgt            40

<210> SEQ ID NO 7
<211> LENGTH: 44
<212> TYPE: DNA
<213> ORGANISM: Artificial Sequence
<220> FEATURE:
<223> OTHER INFORMATION: nphT7 R4

<400> SEQUENCE: 7
cgttgacgaa tgccggtctt acgggtaatc cagtcatcat caac       44

<210> SEQ ID NO 8
<211> LENGTH: 36
<212> TYPE: DNA
<213> ORGANISM: Artificial Sequence
<220> FEATURE:
<223> OTHER INFORMATION: nphT7 F4

<400> SEQUENCE: 8
aagaccggca ttcgtcaacg tcgttgggcg gcggac                36

<210> SEQ ID NO 9
<211> LENGTH: 33

```
<212> TYPE: DNA
<213> ORGANISM: Artificial Sequence
<220> FEATURE:
<223> OTHER INFORMATION: nphT7 R5

<400> SEQUENCE: 9
tcggaggtcg cttggtcgtc cgccgcccaa cga                          33

<210> SEQ ID NO 10
<211> LENGTH: 33
<212> TYPE: DNA
<213> ORGANISM: Artificial Sequence
<220> FEATURE:
<223> OTHER INFORMATION: nphT7 F5

<400> SEQUENCE: 10
gaccaagcga cctccgacct ggcaaccgcg gcg                          33

<210> SEQ ID NO 11
<211> LENGTH: 32
<212> TYPE: DNA
<213> ORGANISM: Artificial Sequence
<220> FEATURE:
<223> OTHER INFORMATION: nphT7 R6

<400> SEQUENCE: 11
tcaacgccgc acgacccgcc gcggttgcca gg                           32

<210> SEQ ID NO 12
<211> LENGTH: 35
<212> TYPE: DNA
<213> ORGANISM: Artificial Sequence
<220> FEATURE:
<223> OTHER INFORMATION: nphT7 F6

<400> SEQUENCE: 12
ggtcgtgcgg cgttgaaagc agcgggtatt acgcc                        35

<210> SEQ ID NO 13
<211> LENGTH: 40
<212> TYPE: DNA
<213> ORGANISM: Artificial Sequence
<220> FEATURE:
<223> OTHER INFORMATION: nphT7 R7

<400> SEQUENCE: 13
gcaataaccg tcagttgctc cggcgtaata cccgctgctt                   40

<210> SEQ ID NO 14
<211> LENGTH: 38
<212> TYPE: DNA
<213> ORGANISM: Artificial Sequence
<220> FEATURE:
<223> OTHER INFORMATION: nphT7 F7

<400> SEQUENCE: 14
ggagcaactg acggttattg cggtcgcaac gtccaccc                     38

<210> SEQ ID NO 15
<211> LENGTH: 33
<212> TYPE: DNA
<213> ORGANISM: Artificial Sequence
<220> FEATURE:
<223> OTHER INFORMATION: nphT7 R8

<400> SEQUENCE: 15
```
ggctgcggac ggtccggggt ggacgttgcg acc					33

<210> SEQ ID NO 16
<211> LENGTH: 32
<212> TYPE: DNA
<213> ORGANISM: Artificial Sequence
<220> FEATURE:
<223> OTHER INFORMATION: nphT7 F8

<400> SEQUENCE: 16
cggaccgtcc gcagccgccg acggcggcct ac					32

<210> SEQ ID NO 17
<211> LENGTH: 35
<212> TYPE: DNA
<213> ORGANISM: Artificial Sequence
<220> FEATURE:
<223> OTHER INFORMATION: nphT7 R9

<400> SEQUENCE: 17
cgcccagatg atgttgcacg taggccgccg tcggc					35

<210> SEQ ID NO 18
<211> LENGTH: 35
<212> TYPE: DNA
<213> ORGANISM: Artificial Sequence
<220> FEATURE:
<223> OTHER INFORMATION: nphT7 F9

<400> SEQUENCE: 18
gtgcaacatc atctgggcgc aaccggcacc gcggc					35

<210> SEQ ID NO 19
<211> LENGTH: 39
<212> TYPE: DNA
<213> ORGANISM: Artificial Sequence
<220> FEATURE:
<223> OTHER INFORMATION: nphT7 R10

<400> SEQUENCE: 19
tgcacacagc gttaacatca aatgccgcgg tgccggttg				39

<210> SEQ ID NO 20
<211> LENGTH: 40
<212> TYPE: DNA
<213> ORGANISM: Artificial Sequence
<220> FEATURE:
<223> OTHER INFORMATION: nphT7 F10

<400> SEQUENCE: 20
atttgatgtt aacgctgtgt gcagcggcac ggttttgct				40

<210> SEQ ID NO 21
<211> LENGTH: 33
<212> TYPE: DNA
<213> ORGANISM: Artificial Sequence
<220> FEATURE:
<223> OTHER INFORMATION: nphT7 R11

<400> SEQUENCE: 21
ccgccacgct ggacagagca aaaaccgtgc cgc					33

<210> SEQ ID NO 22
<211> LENGTH: 35
<212> TYPE: DNA
<213> ORGANISM: Artificial Sequence
<220> FEATURE:
<223> OTHER INFORMATION: nphT7 F11

<400> SEQUENCE: 22
ctgtccagcg tggcgggcac gctggtgtat cgtgg                                    35

<210> SEQ ID NO 23
<211> LENGTH: 39
<212> TYPE: DNA
<213> ORGANISM: Artificial Sequence
<220> FEATURE:
<223> OTHER INFORMATION: nphT7 R12

<400> SEQUENCE: 23
caatgaccag tgcgtaaccg ccacgataca ccagcgtgc                                39

<210> SEQ ID NO 24
<211> LENGTH: 41
<212> TYPE: DNA
<213> ORGANISM: Artificial Sequence
<220> FEATURE:
<223> OTHER INFORMATION: nphT7 F12

<400> SEQUENCE: 24
cggttacgca ctggtcattg gtgccgatct gtattcccgt a                             41

<210> SEQ ID NO 25
<211> LENGTH: 39
<212> TYPE: DNA
<213> ORGANISM: Artificial Sequence
<220> FEATURE:
<223> OTHER INFORMATION: nphT7 R13

<400> SEQUENCE: 25
ggtccgccgg attcagaata cgggaataca gatcggcac                                39

<210> SEQ ID NO 26
<211> LENGTH: 40
<212> TYPE: DNA
<213> ORGANISM: Artificial Sequence
<220> FEATURE:
<223> OTHER INFORMATION: nphT7 F13

<400> SEQUENCE: 26
ttctgaatcc ggcggaccgc aagaccgttg ttctgtttgg                               40

<210> SEQ ID NO 27
<211> LENGTH: 38
<212> TYPE: DNA
<213> ORGANISM: Artificial Sequence
<220> FEATURE:
<223> OTHER INFORMATION: nphT7 R14

<400> SEQUENCE: 27
cgcacccgcg ccgtcaccaa acagaacaac ggtcttgc                                 38

<210> SEQ ID NO 28
<211> LENGTH: 33
<212> TYPE: DNA
<213> ORGANISM: Artificial Sequence
<220> FEATURE:
<223> OTHER INFORMATION: nphT7 F14

<400> SEQUENCE: 28
tgacggcgcg ggtgcgatgg tgctgggtcc gac                                      33

```
<210> SEQ ID NO 29
<211> LENGTH: 33
<212> TYPE: DNA
<213> ORGANISM: Artificial Sequence
<220> FEATURE:
<223> OTHER INFORMATION: nphT7 R15

<400> SEQUENCE: 29
acccgtaccc gtgctggtcg gacccagcac cat                                33

<210> SEQ ID NO 30
<211> LENGTH: 32
<212> TYPE: DNA
<213> ORGANISM: Artificial Sequence
<220> FEATURE:
<223> OTHER INFORMATION: nphT7 F15

<400> SEQUENCE: 30
cagcacgggt acgggtccga tcgtccgtcg cg                                 32

<210> SEQ ID NO 31
<211> LENGTH: 34
<212> TYPE: DNA
<213> ORGANISM: Artificial Sequence
<220> FEATURE:
<223> OTHER INFORMATION: nphT7 R16

<400> SEQUENCE: 31
caaacgtgtg cagggcaacg cgacggacga tcgg                               34

<210> SEQ ID NO 32
<211> LENGTH: 38
<212> TYPE: DNA
<213> ORGANISM: Artificial Sequence
<220> FEATURE:
<223> OTHER INFORMATION: nphT7 F16

<400> SEQUENCE: 32
ttgccctgca cacgtttggt ggtctgaccg acctgatt                           38

<210> SEQ ID NO 33
<211> LENGTH: 36
<212> TYPE: DNA
<213> ORGANISM: Artificial Sequence
<220> FEATURE:
<223> OTHER INFORMATION: nphT7 R17

<400> SEQUENCE: 33
cacccgccgg cacacgaatc aggtcggtca gaccac                             36

<210> SEQ ID NO 34
<211> LENGTH: 32
<212> TYPE: DNA
<213> ORGANISM: Artificial Sequence
<220> FEATURE:
<223> OTHER INFORMATION: nphT7 F17

<400> SEQUENCE: 34
cgtgtgccgg cgggtggcag ccgccaaccg ct                                 32

<210> SEQ ID NO 35
<211> LENGTH: 34
<212> TYPE: DNA
<213> ORGANISM: Artificial Sequence
<220> FEATURE:
<223> OTHER INFORMATION: nphT7 R18
```

```
<400> SEQUENCE: 35
tccaagccat ccgtgtccag cggttggcgg ctgc                              34

<210> SEQ ID NO 36
<211> LENGTH: 38
<212> TYPE: DNA
<213> ORGANISM: Artificial Sequence
<220> FEATURE:
<223> OTHER INFORMATION: nphT7 F18

<400> SEQUENCE: 36
ggacacggat ggcttggacg cgggtctgca atacttcg                          38

<210> SEQ ID NO 37
<211> LENGTH: 38
<212> TYPE: DNA
<213> ORGANISM: Artificial Sequence
<220> FEATURE:
<223> OTHER INFORMATION: nphT7 R19

<400> SEQUENCE: 37
cctcgcgacc gtccatagcg aagtattgca gacccgcg                          38

<210> SEQ ID NO 38
<211> LENGTH: 39
<212> TYPE: DNA
<213> ORGANISM: Artificial Sequence
<220> FEATURE:
<223> OTHER INFORMATION: nphT7 F19

<400> SEQUENCE: 38
ctatggacgg tcgcgaggtg cgtcgttttg ttaccgaac                         39

<210> SEQ ID NO 39
<211> LENGTH: 43
<212> TYPE: DNA
<213> ORGANISM: Artificial Sequence
<220> FEATURE:
<223> OTHER INFORMATION: nphT7 R20

<400> SEQUENCE: 39
cctttaatca gttgcggcaa gtgttcggta acaaaacgac gca                    43

<210> SEQ ID NO 40
<211> LENGTH: 40
<212> TYPE: DNA
<213> ORGANISM: Artificial Sequence
<220> FEATURE:
<223> OTHER INFORMATION: nphT7 F20

<400> SEQUENCE: 40
acttgccgca actgattaaa ggtttcttgc acgaggcggg                        40

<210> SEQ ID NO 41
<211> LENGTH: 40
<212> TYPE: DNA
<213> ORGANISM: Artificial Sequence
<220> FEATURE:
<223> OTHER INFORMATION: nphT7 R21

<400> SEQUENCE: 41
gctaatatct gccgcatcga cacccgcctc gtgcaagaaa                        40

<210> SEQ ID NO 42
```

-continued

```
<210> SEQ ID NO 42
<211> LENGTH: 42
<212> TYPE: DNA
<213> ORGANISM: Artificial Sequence
<220> FEATURE:
<223> OTHER INFORMATION: nphT7 F21

<400> SEQUENCE: 42
tgtcgatgcg gcagatatta gccattttgt gccgcaccaa gc                          42

<210> SEQ ID NO 43
<211> LENGTH: 40
<212> TYPE: DNA
<213> ORGANISM: Artificial Sequence
<220> FEATURE:
<223> OTHER INFORMATION: nphT7 R22

<400> SEQUENCE: 43
cgtccagcat gacaccgttc gcttggtgcg gcacaaaatg                             40

<210> SEQ ID NO 44
<211> LENGTH: 41
<212> TYPE: DNA
<213> ORGANISM: Artificial Sequence
<220> FEATURE:
<223> OTHER INFORMATION: nphT7 F22

<400> SEQUENCE: 44
gaacggtgtc atgctggacg aggtctttgg tgaactgcac c                           41

<210> SEQ ID NO 45
<211> LENGTH: 37
<212> TYPE: DNA
<213> ORGANISM: Artificial Sequence
<220> FEATURE:
<223> OTHER INFORMATION: nphT7 R23

<400> SEQUENCE: 45
atggtcgcac gcggcaggtg cagttcacca aagacct                                37

<210> SEQ ID NO 46
<211> LENGTH: 35
<212> TYPE: DNA
<213> ORGANISM: Artificial Sequence
<220> FEATURE:
<223> OTHER INFORMATION: nphT7 F23

<400> SEQUENCE: 46
tgccgcgtgc gaccatgcac cgtaccgtcg aaacc                                  35

<210> SEQ ID NO 47
<211> LENGTH: 37
<212> TYPE: DNA
<213> ORGANISM: Artificial Sequence
<220> FEATURE:
<223> OTHER INFORMATION: nphT7 R24

<400> SEQUENCE: 47
cgcacccgta ttgccgtagg tttcgacggt acggtgc                                37

<210> SEQ ID NO 48
<211> LENGTH: 39
<212> TYPE: DNA
<213> ORGANISM: Artificial Sequence
<220> FEATURE:
<223> OTHER INFORMATION: nphT7 F24

<400> SEQUENCE: 48
```

```
tacggcaata cgggtgcggc cagcattccg attacgatg                    39
```

\<210\> SEQ ID NO 49
\<211\> LENGTH: 39
\<212\> TYPE: DNA
\<213\> ORGANISM: Artificial Sequence
\<220\> FEATURE:
\<223\> OTHER INFORMATION: nphT7 R25

\<400\> SEQUENCE: 49

```
tgcacggact gctgcatcca tcgtaatcgg aatgctggc                    39
```

\<210\> SEQ ID NO 50
\<211\> LENGTH: 35
\<212\> TYPE: DNA
\<213\> ORGANISM: Artificial Sequence
\<220\> FEATURE:
\<223\> OTHER INFORMATION: nphT7 F25

\<400\> SEQUENCE: 50

```
gatgcagcag tccgtgcagg tagcttccgt ccggg                        35
```

\<210\> SEQ ID NO 51
\<211\> LENGTH: 35
\<212\> TYPE: DNA
\<213\> ORGANISM: Artificial Sequence
\<220\> FEATURE:
\<223\> OTHER INFORMATION: nphT7 R26

\<400\> SEQUENCE: 51

```
gccagcagga ccagttcacc cggacggaag ctacc                        35
```

\<210\> SEQ ID NO 52
\<211\> LENGTH: 37
\<212\> TYPE: DNA
\<213\> ORGANISM: Artificial Sequence
\<220\> FEATURE:
\<223\> OTHER INFORMATION: nphT7 F26

\<400\> SEQUENCE: 52

```
tgaactggtc ctgctggcgg gttttggtgg tggcatg                      37
```

\<210\> SEQ ID NO 53
\<211\> LENGTH: 35
\<212\> TYPE: DNA
\<213\> ORGANISM: Artificial Sequence
\<220\> FEATURE:
\<223\> OTHER INFORMATION: nphT7 R27

\<400\> SEQUENCE: 53

```
gcgcgaagct cgctgccatg ccaccaccaa aaccc                        35
```

\<210\> SEQ ID NO 54
\<211\> LENGTH: 37
\<212\> TYPE: DNA
\<213\> ORGANISM: Artificial Sequence
\<220\> FEATURE:
\<223\> OTHER INFORMATION: nphT7 F27

\<400\> SEQUENCE: 54

```
gcagcgagct tcgcgctgat cgagtggtaa gtcagcc                      37
```

\<210\> SEQ ID NO 55
\<211\> LENGTH: 38
\<212\> TYPE: DNA

```
<213> ORGANISM: Artificial Sequence
<220> FEATURE:
<223> OTHER INFORMATION: nphT7 R28

<400> SEQUENCE: 55
acccgctcta gccgtcaggc tgacttacca ctcgatca                    38

<210> SEQ ID NO 56
<211> LENGTH: 17
<212> TYPE: DNA
<213> ORGANISM: Artificial Sequence
<220> FEATURE:
<223> OTHER INFORMATION: nphT7 F28

<400> SEQUENCE: 56
tgacggctag agcgggt                                           17

<210> SEQ ID NO 57
<211> LENGTH: 58
<212> TYPE: DNA
<213> ORGANISM: Artificial Sequence
<220> FEATURE:
<223> OTHER INFORMATION: NphT7 G F

<400> SEQUENCE: 57
aatttcacac gagctcggta cccgggagga gatataccat gaccgacgtt cgttttcg    58

<210> SEQ ID NO 58
<211> LENGTH: 50
<212> TYPE: DNA
<213> ORGANISM: Artificial Sequence
<220> FEATURE:
<223> OTHER INFORMATION: NphT7 G R

<400> SEQUENCE: 58
gcgctgggtc attatatatc tccttttctt accactcgat cagcgcgaag             50

<210> SEQ ID NO 59
<211> LENGTH: 43
<212> TYPE: DNA
<213> ORGANISM: Artificial Sequence
<220> FEATURE:
<223> OTHER INFORMATION: PhaB F

<400> SEQUENCE: 59
gaaaaggaga tatataatga cccagcgcat cgcttacgta acc              43

<210> SEQ ID NO 60
<211> LENGTH: 56
<212> TYPE: DNA
<213> ORGANISM: Artificial Sequence
<220> FEATURE:
<223> OTHER INFORMATION: PhaB R

<400> SEQUENCE: 60
gcttgcatgc ctgcaggtcg actctagagg atctcatgcc ttggctttga cgtatc      56

<210> SEQ ID NO 61
<211> LENGTH: 37
<212> TYPE: DNA
<213> ORGANISM: Artificial Sequence
<220> FEATURE:
<223> OTHER INFORMATION: MatB.SCo F

<400> SEQUENCE: 61
tcgattgcac atatgtcctc tctcttcccg gccctct                     37
```

<210> SEQ ID NO 62
<211> LENGTH: 39
<212> TYPE: DNA
<213> ORGANISM: Artificial Sequence
<220> FEATURE:
<223> OTHER INFORMATION: MatB.SCo R

<400> SEQUENCE: 62
atcggatagc tcgagtcagt cacggttcag cgcccgctt                      39

<210> SEQ ID NO 63
<211> LENGTH: 32
<212> TYPE: DNA
<213> ORGANISM: Artificial Sequence
<220> FEATURE:
<223> OTHER INFORMATION: Epi.SCo F

<400> SEQUENCE: 63
atcccgaatc atatgctgac gcgaatcgac ca                             32

<210> SEQ ID NO 64
<211> LENGTH: 35
<212> TYPE: DNA
<213> ORGANISM: Artificial Sequence
<220> FEATURE:
<223> OTHER INFORMATION: Epi.SCo R

<400> SEQUENCE: 64
ttagtctggc tcgagtcagt gctcaggtga ctcaa                          35

<210> SEQ ID NO 65
<211> LENGTH: 28
<212> TYPE: DNA
<213> ORGANISM: Artificial Sequence
<220> FEATURE:
<223> OTHER INFORMATION: AckA.EC F

<400> SEQUENCE: 65
ggagatatac atatgtcgag taagttag                                  28

<210> SEQ ID NO 66
<211> LENGTH: 30
<212> TYPE: DNA
<213> ORGANISM: Artificial Sequence
<220> FEATURE:
<223> OTHER INFORMATION: AckA.EC R

<400> SEQUENCE: 66
attggatcct ctagatcagg cagtcaggcg                                30

<210> SEQ ID NO 67
<211> LENGTH: 30
<212> TYPE: DNA
<213> ORGANISM: Artificial Sequence
<220> FEATURE:
<223> OTHER INFORMATION: Pta.EC F

<400> SEQUENCE: 67
attcatatgt cccgtattat tatgctgatc                                30

<210> SEQ ID NO 68
<211> LENGTH: 28
<212> TYPE: DNA
<213> ORGANISM: Artificial Sequence
<220> FEATURE:

<223> OTHER INFORMATION: Pta.EC R

<400> SEQUENCE: 68
attctcgagg agggtaccga cgtcttac                                28

<210> SEQ ID NO 69
<211> LENGTH: 46
<212> TYPE: DNA
<213> ORGANISM: Artificial Sequence
<220> FEATURE:
<223> OTHER INFORMATION: THNS.SCo F

<400> SEQUENCE: 69
attcatatgg cgactttgtg cagaccctcg gtgtccgtcc cggagc           46

<210> SEQ ID NO 70
<211> LENGTH: 44
<212> TYPE: DNA
<213> ORGANISM: Artificial Sequence
<220> FEATURE:
<223> OTHER INFORMATION: THNS.SCo R

<400> SEQUENCE: 70
attactagtt catgcctgcc tcaccctccg cgacacgccc cgtg             44

<210> SEQ ID NO 71
<211> LENGTH: 54
<212> TYPE: DNA
<213> ORGANISM: Artificial Sequence
<220> FEATURE:
<223> OTHER INFORMATION: pCDF-MatB.SCo F

<400> SEQUENCE: 71
ttagttaagt ataagaagga gatatacata tgtcctctct cttcccggcc ctct  54

<210> SEQ ID NO 72
<211> LENGTH: 47
<212> TYPE: DNA
<213> ORGANISM: Artificial Sequence
<220> FEATURE:
<223> OTHER INFORMATION: pCDF-MatB.SCo R

<400> SEQUENCE: 72
gtttctttac cagactcgag ggtacctcag tcacggttca gcgcccg          47

<210> SEQ ID NO 73
<211> LENGTH: 51
<212> TYPE: DNA
<213> ORGANISM: Artificial Sequence
<220> FEATURE:
<223> OTHER INFORMATION: pCDF-DszsAT.SCe F

<400> SEQUENCE: 73
gtttaacttt aataaggaga tataccatga agcatacat gtttcccggg c       51

<210> SEQ ID NO 74
<211> LENGTH: 48
<212> TYPE: DNA
<213> ORGANISM: Artificial Sequence
<220> FEATURE:
<223> OTHER INFORMATION: pCDF-DszsAT.SCe R

<400> SEQUENCE: 74
cttaagcatt atgcggccgc aagcttgtta cgacgacgag gggctggg         48

```
<210> SEQ ID NO 75
<211> LENGTH: 58
<212> TYPE: DNA
<213> ORGANISM: Artificial Sequence
<220> FEATURE:
<223> OTHER INFORMATION: MBP-M2 F

<400> SEQUENCE: 75
gggatcgagg aaaacctgta ttttcagggc atgagcggtg acaacggcat gaccgagg        58

<210> SEQ ID NO 76
<211> LENGTH: 60
<212> TYPE: DNA
<213> ORGANISM: Artificial Sequence
<220> FEATURE:
<223> OTHER INFORMATION: MBP-M2 R

<400> SEQUENCE: 76
gcttgtcgac ggagctcgaa ttcggggatc ctcagtggtg gtggtggtgg tgctcgagtg      60

<210> SEQ ID NO 77
<211> LENGTH: 60
<212> TYPE: DNA
<213> ORGANISM: Artificial Sequence
<220> FEATURE:
<223> OTHER INFORMATION: MBP-M2ATnull F

<400> SEQUENCE: 77
gttatcggtc acgcgcaggg tgaaatcgcg gccgcggtgg tggcgggagc gttgtcgctg      60

<210> SEQ ID NO 78
<211> LENGTH: 60
<212> TYPE: DNA
<213> ORGANISM: Artificial Sequence
<220> FEATURE:
<223> OTHER INFORMATION: MBP-M2ATnull R

<400> SEQUENCE: 78
cgcgatttca ccctgcgcgt gaccgataac ggccgaagga acggcaccgc aggcacgcca      60
```

METHODS FOR THE SITE-SELECTIVE INTRODUCTION OF HALOGEN INTO NATURAL PRODUCTS

CROSS REFERENCE TO RELATED APPLICATIONS

This application claims, under 35 USC 119(e), the benefit of U.S. Provisional Application No. 61/868,494 filed Aug. 21, 2013, which is incorporated herein by reference in its entirety for all purposes.

STATEMENT AS TO RIGHTS TO INVENTIONS MADE UNDER FEDERALLY SPONSORED RESEARCH OR DEVELOPMENT

This invention was made with Government support under Grant No. 1-DP2-OD008696 awarded by National Institutes of Health. The Government has certain rights in the invention.

FIELD OF THE INVENTION

Reagents and methods for the in vitro and in vivo synthesis of polyketides are provided.

BACKGROUND OF THE INVENTION

The catalytic diversity of biological systems provides enormous potential for application of living cells to the scalable production of pharmaceuticals, fuels, and materials (Ro, et al., Nature, 440: 940-943 (2006); Atsumi, et al., Nature 451, 86-89 (2008); Cane, et al., Science 282:63-68 (1998); and Weeks, et al., Biochemistry 50, 5404-5418 (2011)). However, the scope of innovation of living organisms is typically limited to functions that confer a direct advantage for cell growth, thereby maximizing biomass as the end product rather than a distinct molecule or reaction of interest. In contrast, synthetic biology approaches allow us to disconnect some of these remarkable biochemical transformations from cell survival and reconnect them differently for the targeted synthesis of alternative classes of compounds. One particularly interesting area of opportunity is the development of methods to introduce halides into complex small molecule scaffolds, which has become a powerful strategy for the design of synthetic pharmaceuticals. Indeed, it is estimated that 20-30% of drugs, including many of the top sellers, contain at least one fluorine atom (Müller, et al., Science, 317:1881-1886 (2007); D. O'Hagan, Chem. Soc. Rev. 37:308-319 (2008); and Furuya, et al., Nature, 473: 470-477 (2011)). For example, tecent innovations have expanded the scope of synthetic CF bond forming methodologies, but the unusual elemental properties of fluorine that serve as the basis for its success also continue to restrict the range of molecular structures that can be accessed (Ball, et al., J. Am. Chem. Soc., 131:3796-3797 (2009); Watson et al., Science, 325:1661-1664 (2009); Rauniyar, et al., Science, 334:1681-1684 (2011); and Lee, et al., Science, 334:639-642 (2011)). As such, the invention of alternative routes for the site-selective introduction of halogens into structurally diverse molecules, particularly under mild conditions, remains an outstanding challenge.

In comparison to synthetic small molecules, halogens, e.g., fluorine, have limited distribution in naturally occurring organic compounds. For example, the only organofluorine natural products characterized to date consist of a small set of simple molecules associated with the fluoroacetate pathway of Streptomyces cattleya, a soil bacterium that houses the remarkable ability to catalyze the formation of CF bonds from aqueous fluoride (FIG. 1A) (Dong, et al., Nature, 427:561-565 (2004); and D. O'Hagan, J. Fluorine Chem., 127:1479-1483 (2006)).

The backbones of several large classes of medicinally-relevant natural products including polyketides, isoprenoids, steroids, alkaloids, eicosanoids, leukotrienes, and others are biosynthesized directly from the assembly and tailoring of simple acetate units (FIG. 1A). Introduction of the haloacetate monomer in place of acetate would allow incorporation of fluorine into the backbone of these targets and create new molecular function by combining the medicinal chemistry advantages of fluorine with the structural complexity and bioactivity of natural products. The present invention provides a method for accomplishing this goal.

BRIEF SUMMARY OF THE INVENTION

In various embodiments, the present invention is directed toward increasing the typically low yields associated with conventional synthesis of halo-polyketides and other natural products (e.g., isoprenoids, steroids, alkaloids, eicosanoids, leukotrienes) formed by the condensation of acetate groups. In various embodiments, the current invention is directed toward new methods for the synthesis of natural products such as functionalized triketides. In various embodiments, malonyl-CoA is an example of a universal extender in triketide synthesis, and the synthesis of other natural products involving condensation of acetate.

Amongst various embodiments, the present invention provides direct and efficient access to halomalonyl-CoA, a halogenated analog of one of nature's most ubiquitous carbon nucleophiles. Also provided are methods of using this compound as an extender unit, which affords a general method for direct incorporation of halogen into a large array of polyketide and other natural product structures.

It is a further object of the invention to provide a host microorganism, wherein a heterologous nucleic acid sequence comprises a DNA fragment coding for an enzyme competent to incorporate a halogenated malonyl-CoA analogue in a synthetic pathyway for a polyketide.

It is still a further object of the invention to provide a method wherein the host microorganism is a prokaryote.

It is an additional object of the invention to provide a method wherein the prokaryote is Escherichia coli.

Is it still another object of the invention to provide a method for synthesizing a halogenated ketide, e.g., a polyketide, in a host microorganism, wherein the method comprises introducing into the host microorganism a compound of Formula I, II and/or III and at least one heterologous nucleic acid sequence. Exemplary heterologous nucleic acid sequences encode for an enzyme that catalyzes the ligation of CoA onto halomalonic acid, haloacetic acid or the condensation of one of these haloacids on to a substrate for a polyketide.

It is still a further object of the invention to provide DNA fragments, expression vectors, and host cells for carrying out the methods described herein.

Additional objects, advantages, and novel features of the invention will be set forth in part in the description that follows, and in part will become apparent to those skilled in the art upon examination of the following, or may be learned through routine experimentation upon practice of the invention.

BRIEF DESCRIPTION OF THE DRAWINGS

FIG. 6A-C. Formation of fluoroacetyl-CoA using AckAPta. (A) HPLC chromatograms monitoring fluoroacetyl-CoA formation by $A_{260\ nm}$. (B) Plot of the conversion of free CoA to fluoroacetyl-CoA. (C) Kinetic parameters for AckA and Pta measured using spectrophotometric assays. (Walker, et al., ACS Chem. Biol. (2012)). Values are reported as the mean±s.e. as determined from nonlinear curve fitting.

DETAILED DESCRIPTION OF THE INVENTION

I. Introduction

Figure 1A:
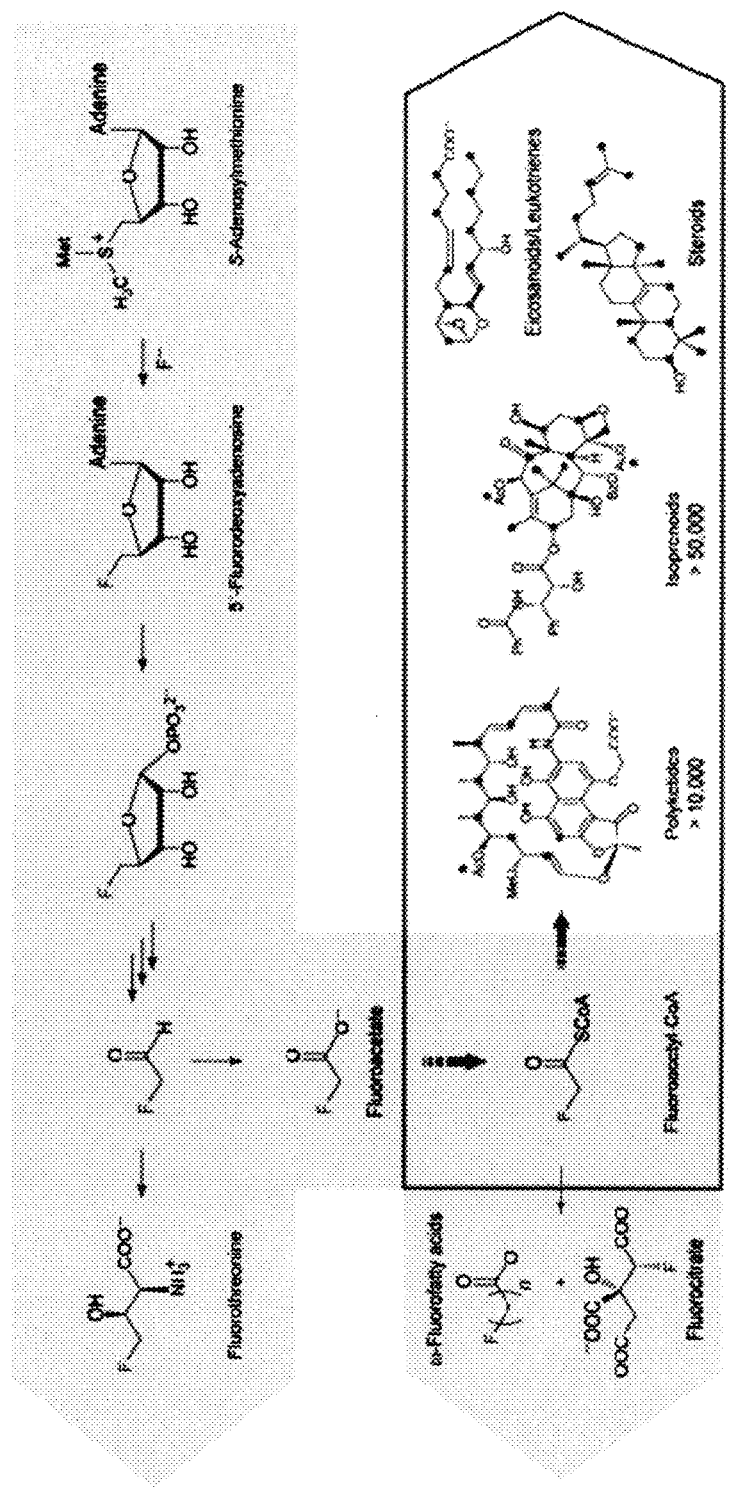
FIG. 1A-B. Synthetic biology of fluorine. (A) The fluoroacetate pathway and its metabolites represent the known scope of biological fluorine chemistry, starting with fluoride and S-adenosylmethionine, to produce fluoroacetate and fluorothreonine as the end products (right to left, grey box). This scope is greatly expanded by engineering downstream pathways to use fluoroacetate as a building block for introduction of fluorine site-selectively into large families of natural products constructed from acetate backbones (left to right, red box). Red dots represent positions that can be fluorinated by incorporation of a fluoroacetate monomer without altering the carbon skeleton, including locations where fluorine would replace a methyl group derived from propionate or where downstream tailoring steps have occurred on the final structure. (B) Assembly of acetate units in the biosynthesis of polyketide natural products.

The present invention provides compounds, cells, systems and methods which expand the halogen chemistry of living systems using engineered pathways to link simple biogenic organohalide building blocks into more complex halogenated small molecule targets. Because of the modular nature of the biosynthetic pathways used to produce polyketides and related acetate-derived natural products, the present invention opens the door to general strategies for exploring the halogen synthetic biology of complex natural products, and for producing such products.

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

In describing the present invention, the following terms will be employed, and are defined as indicated below.

II. Definitions

The terms "host microorganism" and "cell" are used interchangeably herein to refer to a living biological cell that can be transformed via insertion of an expression vector. Thus, a host organism or cell as described herein may be a prokaryotic organism (e.g., an organism of the kingdom Eubacteria) or a eukaryotic cell. As will be appreciated by one of ordinary skill in the art, a prokaryotic cell lacks a membrane-bound nucleus, while a eukaryotic cell has a membrane-bound nucleus. A preferred prokaryotic cell is *Escherichia coli*. Preferred eukaryotic cells are those derived from fungal, insect, or mammalian cell lines.

The term "heterologous DNA" as used herein refers to a polymer of nucleic acids wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid. Specifically, the present invention describes the introduction of an expression vector into a host microorganism, wherein the expression vector contains a nucleic acid sequence coding for an enzyme that is not normally found in a host microorganism. With reference to the host microorganism's genome, then, the nucleic acid sequence that codes for the enzyme is heterologous.

The term "polyketide synthase pathway" is used herein to refer to the pathway that utilizes acetyl-CoA or malonyl-CoA as extender subunits or extender subunit synthons in condensation reactions to form reactive β-keto units.

The terms "expression vector" or "vector" refer to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Preferred expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "transduce" as used herein refers to the transfer of a sequence of nucleic acids into a host microorganism or cell. Only when the sequence of nucleic acids becomes stably replicated by the cell does the host microorganism or cell become "transformed." As will be appreciated by those of ordinary skill in the art, "transformation" may take place either by incorporation of the sequence of nucleic acids into the cellular genome, i.e., chromosomal integration, or by extrachromosomal integration. In contrast, an expression vector, e.g., a virus, is "infective" when it transduces a host microorganism, replicates, and (without the benefit of any complementary virus or vector) spreads progeny expression vectors, e.g., viruses, of the same type as the original transducing expression vector to other microorganisms, wherein the progeny expression vectors possess the same ability to reproduce.

The terms "isolated" or "biologically pure" refer to material that is substantially or essentially free of components that normally accompany it in its native state.

As used herein, the terms "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing nonnucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog; internucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IUPAC-IUB Commission of Biochemical Nomenclature (Biochemistry 9:4022, 1970).

The term "operably linked" refers to a functional linkage between a nucleic acid expression control sequence (such as a promoter) and a second nucleic acid sequence, wherein the expression control sequence directs transcription of the nucleic acid corresponding to the second sequence.

"Polyketides" refers to a large group of natural products that are derived from successive condensations of simple carboxylates, such as acetate, propionate or butyrate. Naturally occurring polyketides possess a broad range of biological activities, including antibiotics such as tetracyclines and erythromycin, anticancer agents such as daunomycin and bryostatin, immunosuppressants such as FK506 and rapamycin, and veterinary products such as monensin and avermectin. Polyketides are produced in most groups of organisms and are especially abundant in a class of mycelial bacteria, the actinomycetes, which produce various types of polyketides.

"Substrate for the polyketide synthase" refers to any substrate onto which a polyketide synthase is competent to condense an extender. Exemplary extenders include halomalonyl and haloacetyl moieties. An exemplary halo moiety is fluoro.

The term "non-toxic" refers to an amount of a compound insufficient to destroy 50% of the cells of a population of a host microorganism. The compound may be present in an amount sufficient to inhibit or even arrest cell growth, but allows polyketide formation to occur efficiently.

Also, and more generally, in accordance with disclosures, discussions, examples and embodiments herein, there may be employed conventional molecular biology, cellular biology, microbiology, and recombinant DNA techniques within the skill of the art. Such techniques are explained fully in the literature. (See, e.g., Sambrook, et al., "Molecular Cloning: A Laboratory Manual," Third Edition 2001 (volumes 1-3), Cold Spring Harbor Laboratory Press, Cold Spring Harbor, N.Y.; Animal Cell Culture, R. I. Freshney, ed., 1986.)

III. The Compositions

In an exemplary embodiment, the invention provides a halogenated polyketide, or an analogue thereof. An exemplary halogenated polyketide is enzymatically synthesized either by a host microorganism or by one or more isolated enzymes by condensation of a substrate for a polyketide synthase and an extender according to Formula I:

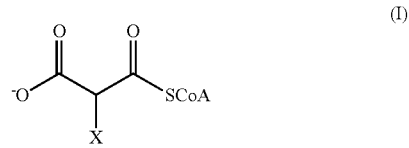

in which X is selected from F, Cl, Br and I.

In various embodiments, the extender according to Formula I is prepared from a precursor according to Formula II:

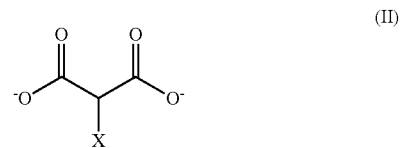

in which X is as described above.

In an exemplary embodiment, the precursor according to Formula II is converted to the compound according to Formula I by the action of malonyl-CoA sythetase (MatB). The conversion can occur using isolated enzymes or within a host microorganism (e.g., an engineered host microorganism) expressing one or more of these enzymes. In an exemplary embodiment, MatB is a wild type enzyme from *E. coli*. In another embodiment, MatB is a non-naturally occurring enzyme.

In another embodiment, the compound according to Formula I is produced by enzymatic conversion of a precursor acetyl compound of Formula III to the corresponding malonyl compound:

in which X is as described above.

In an exemplary embodiment, the compound according to Formula III is converted to the compound according to Formula I by the action of acetate kinase, phosphotransacetylase and the AccABCD subunits that make up acetyl coenzyme A carboxylase (ACCase). The conversion can occur using isolated enzymes or within a host microorganism (e.g., an engineered host microorganism) expressing one or more of these enzymes. In an exemplary embodiment, the AckA, Pta and/or the ACCase is a wild type enzyme from *E. coli*. In another embodiment, the AckA, Pta and/or ACCase is a non-naturally occurring enzyme.

In another embodiment, the extender according to Formula I is produced by conversion of the percursor of Formula III by the action of acetate kinase (AckA) and phosphotransacetylase (Pta). The conversion can occur using isolated enzymes or within a host microorganism (e.g., an engineered host microorganism) expressing this enzyme. In an exemplary embodiment, one or both of the AckA and Pta is (are) a wild type enzyme from *E. coli*. In another embodiment, one or both of the AckA and Pta is (are) a non-naturally occurring enzyme.

In various embodiments, the precursor of Formula III is converted to the extender of Formula I using acyl-CoA synthase. The conversion can occur using isolated enzymes or within a host microorganism (e.g., an engineered host microorganism) expressing this enzyme. In an exemplary embodiment, the acyl-CoA synthase is a wild type enzyme from *E. coli*. In another embodiment, the acyl-CoA synthase is a non-naturally occurring enzyme.

In an exemplary embodiment, the invention provides a polyketide synthase functionalized with a halomalonyl moiety. In various embodiments, the halomalonyl moiety is derived from a compound of Formula I and is transferred to the polyketide synthase via the action of a trans-acyl transferase.

In an exemplary embodiment, the invention provides a host microorganism cell that includes any one or more of the above-described components in an internal space of the host microorganism cell.

Polyketide Synthase

The enzymes responsible for the biosynthesis of polyketides are called polyketide synthases (PKSs). Two general classes of PKSs exist. One class, known as Type I PKSs, is represented by the PKSs for the synthesis of macrolide polyketides such as erythromycin and rapamycin. This type of PKSs has a modular enzymatic structure, in which a module is defined as a set of enzymatic domains that are necessary to catalyze the recognition and incorporation of a specific 2-carbon extending unit (usually a malonyl-CoA, a methyl malonyl-CoA or a propionyl-CoA) into the growing polyketide chain. A minimal type I PKS module contains three enzymatic domains: (1) a ketosynthase domain (KS) which is responsible for catalyzing the Claisen condensation reaction between a starter unit or a growing polyketide chain and an extender unit; (2) an acyltransferase domain (AT) which selectively binds a specific extender unit from the intracellular pools of the various CoA carboxylates and then transfers it to the acyl carrier center; (3) an acyl carrier protein domain (ACP) which contains a serine residue that has been post-translationally modified with a 4-phosphopantethein group and serves as the acceptor for the extender unit or a growing polyketide chain. In addition to the KS, AT, and ACP domains, a type I PKS module can also have one, two or three of the following domains: a ketoreductase domain (KR) which reduces the β-ketone to the hydroxyl function, a dehydratase domain (DH) which eliminates water from the α,β carbon centers to generate a double bond between them, and a enoylreductase domain (ER) which further reduces the double bond generated by DH domain to yield the β-methylene group.

A co-linear relationship exists between the primary organization of the Type I PKS and the structure of the polyketide backbone. For examples, the number of modules in the PKS determines the number of the two-carbon units in the carbon backbone of the final polyketide product, the presence of a specific AT domain determines which extender (malonate, methylmalonate or ethylmalonate, etc.) is incorporated into the growing polyketide chain, and the presence of the reduction domains (KR, DH and ER) in a module determines the extent of reduction of the .beta.-carbon formed at the give condensation.

The second class of PKSs, called Type II PKSs, is responsible for the synthesis of aromatic polyketides such as daunorubicin and tetracenomycin. Type II PKSs have a single set of enzymatic activities (KS, AT, ACP, KR, etc.) that reside in individual proteins and are used iteratively to generate polyketides with polycyclic ring structure. There is no clear correlation between the type II PKS enzymatic organization and the final polyketide structure.

The present invention provides a method of using the polyketide synthase (PKS) pathway to synthesize halogenated natural product scaffolds. The PKS of use in the invention may be naturally occurring or non-naturally occurring. In some embodiments, the PKS is a hybrid PKS comprising of a combination of naturally occurring modules which in nature are not found in this combination. In various embodiments, the PKS is naturally occurring but is heterologous to the host microorganism. In an exemplary embodiment, the PKS is encoded by heterologous DNA.

Chain length is determined by the number of condensations that take place, which in turn is determined by the number of modules employed. All chain growth uses a starter determined by the loading module, typically contributing two (S1) or three (S2) carbon atoms to the overall length of the acyl chain. Each extender module (e.g., the compound of Formula I) contributes two carbons to the backbone and a halogen. In various embodiments, the extender unit is halogenated and contributes carbons in addition to those contributed by the compound of Formula I (e.g., the extender molecule is a higher order homologue of a compound of Formula I).

In various embodiments, the invention provides a method in which a single condensation yields a molecule with 4 carbon atoms (modules S1 and D); two condensations generate a molecule that contains 6 carbons. Similarly, three condensations will yield molecules with 8 carbon backbones.

In an exemplary embodiment, the invention utilizes a compound according to Formula I in at least one cycle of chain extension and ketoreduction, at least two cycles, at least three cycles, or at least four cycles. In an exemplary embodiment, the at least one cycle generates a compound with a 2-halo-3-keto motif.

Any polyketide synthase, whether naturally occurring or non-naturally occurring can be used in practicing the methods of the invention. In an exemplary embodiment, the polyketide synthase is 6-deoxyethrythrolinide B synthase (DEBS)

The PKS can reside within a host cell, or it can be isolated or purified. The PKS can synthesize the compound having an extended product with a 2-halo-3-keto motif in vivo (in a host microorganism) or in vitro (in a cell extract or where all necessary chemical components or starting materials are provided). The present invention provides methods of producing the extended product using any of these in vivo or in vitro means.

The level of reduction is also determined by the modules employed. In general, if more reduced molecules are desired, modules D, J, or one from the H group should be used. If a hydroxyl is desired internally to enable the formation of a lactone, a module from the B or F group should be used. Lactone formation will occur if a PKS thioesterase domain (e.g. eryTE) is placed immediately downstream of the terminal external module.

Engineered Enzymes and Host Cells

The present invention provides for incorporation into a host microorganism of a recombinant nucleic acid encoding an enzyme of use in carrying out the process of the invention. As will be apparent to those of skill in the art, exemplary enzymes include acetate kinase (AckA), phosphotransacetylase (Pta), one or more subunit (e.g., AccABCD) of acetyl-CoA carboxylase, malonyl-CoA synthetase and polyketide synthase (PKS). This aspect of the invention is illustrated in a non-limiting manner by reference to PKS.

Analogues of a naturally occurring PKS are prepared by manipulation of the relevant genes. A large number of modular PKS gene clusters have been mapped and/or sequenced, including erythromycin, soraphen A, rifamycin, and rapamycin, which have been completely mapped and sequenced, and FK506 and oleandomycin which have been partially sequenced, and candicidin, avermectin, and nemadectin which have been mapped and partially sequenced. Additional modular PKS gene clusters are expected to be available as time progresses. These genes can be manipulated using standard techniques to delete or inactivate activity encoding regions, insert regions of genes encoding corresponding activities from the same or different PKS system, or otherwise mutated using standard procedures for obtaining genetic alterations.

Mutations can be made to the native sequences using conventional techniques. The substrates for mutation can be an entire cluster of genes or only one or two of them; the substrate for mutation may also be portions of one or more of these genes. Techniques for mutation include preparing synthetic oligonucleotides including the mutations and inserting the mutated sequence into the gene encoding a PKS subunit using restriction endonuclease digestion. (See, e.g., Kunkel, T. A. *Proc Natl Acad Sci USA* (1985) 82:448; Geisselsoder et al. *BioTechniques* (1987) 5:786.) Alternatively, the mutations can be effected using a mismatched primer (generally 10-20 nucleotides in length) which hybridizes to the native nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. Zoller and Smith, Methods Enzymol. (1983) 100:468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al. *Proc Natl Acad Sci USA* (1982) 79:6409. PCR mutagenesis will also find use for effecting the desired mutations.

If replacement of a particular target region in a host polyketide synthase is to be made, this replacement can be conducted in vitro using suitable restriction enzymes or can be effected in vivo using recombinant techniques involving homologous sequences framing the replacement gene in a donor plasmid and a receptor region in a recipient plasmid. Such systems, advantageously involving plasmids of differing temperature sensitivities are described, for example, in PCT publication WO 96/40968.

The vectors used to perform the various operations to replace the enzymatic activity in the host PKS genes or to support mutations in these regions of the host PKS genes may be chosen to contain control sequences operably linked to the resulting coding sequences in a manner that expression of the coding sequences may be effected in a appropriate host. However, simple cloning vectors may be used as well.

The recombinant nucleic acid can be a double-stranded or single-stranded DNA, or RNA. The recombinant nucleic acid can encode an open reading frame (ORF) of the PKS of the present invention. The recombinant nucleic acid can also comprise promoter sequences for transcribing the ORF in a suitable host cell. The recombinant nucleic acid can also comprise sequences sufficient for having the recombinant nucleic acid stably replicate in a host cell. The recombinant nucleic acid can be replicon capable of stable maintenance in a host cell. In some embodiments, the replicon is a plasmid. The present invention also provides for a vector or expression vector comprising a recombinant nucleic acid of the present invention.

It will be apparent to one of skill in the art that a variety of recombinant vectors can be utilized in the practice of aspects of the invention. Appropriate expression vectors are well known to those of skill in the art and include those that are replicable in eukaryotic cells and/or prokaryotic cells and those that remain episomal or those that integrate into the host cell genome.

The vectors may be chosen to contain control sequences operably linked to the resulting coding sequences in a manner that expression of the coding sequences may be effected in an appropriate host. Suitable control sequences include those that function in eukaryotic and prokaryotic host cells. If the cloning vectors employed to obtain PKS genes encoding derived PKS lack control sequences for expression operably linked to the encoding nucleotide sequences, the nucleotide sequences are inserted into appropriate expression vectors. This can be done individually, or using a pool of isolated encoding nucleotide sequences, which can be inserted into host vectors, the resulting vectors transformed or transfected into host cells, and the resulting cells plated out into individual colonies. Suitable control sequences for single cell cultures of various types of organisms are well known in the art. Control systems for expression in yeast are widely available and are routinely used. Control elements include promoters, optionally containing operator sequences, and other elements depending on the nature of the host, such as ribosome binding sites. Particularly useful promoters for prokaryotic hosts include those from PKS gene clusters that result in the production of polyketides as secondary metabolites, including those from Type I or aromatic (Type II) PKS gene clusters. Examples are act promoters, tcm promoters, spiramycin promoters, and the like. However, other bacterial promoters, such as those derived from sugar metabolizing enzymes, such as galactose, lactose (lac) and maltose, are also useful. Additional examples include promoters derived from biosynthetic enzymes such as for tryptophan (trp), the β-lactamase (bla), bacteriophage lambda PL, and T5. In addition, synthetic promoters, such as the tac promoter (U.S. Pat. No. 4,551,433), can be used.

As noted, particularly useful control sequences are those which themselves, or with suitable regulatory systems, activate expression during transition from growth to stationary phase in the vegetative mycelium. Illustrative control sequences, vectors, and host cells of these types include the modified *S. coelicolor* CH999 and vectors described in PCT Publication No. WO 96/40968 and similar strains of *S. lividans*. See U.S. Pat. Nos. 5,672,491; 5,830,750; 5,843, 718; and 6,177,262, each of which is hereby incorporated by reference. Other regulatory sequences may also be desirable which allow for regulation of expression of the PKS sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes that confer antibiotic resistance or sensitivity to the plasmid.

In various embodiments polypeptides obtained by the expression of the polynucleotide molecules of the present invention may have at least approximately 50%, 60%, 70%, 80%, 90%, 95%, 96%, 97%, 98%, 99% or 100% identity to one or more amino acid sequences encoded by the genes and/or nucleic acid sequences described herein for the polyketide tolerance-related and biosynthesis pathways.

As a practical matter, whether any particular polypeptide is at least 50%, 60%, 70%, 80%, 85%, 90%, 92%, 95%, 96%, 97%, 98% or 99% identical to any reference amino acid sequence of any polypeptide described herein (which may correspond with a particular nucleic acid sequence described herein), such particular polypeptide sequence can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set such that the percentage of identity is calculated over the full length of the reference amino acid sequence and that gaps in homology of up to 5% of the total number of amino acid residues in the reference sequence are allowed.

For example, in a specific embodiment the identity between a reference sequence (query sequence, i.e., a sequence of the present invention) and a subject sequence, also referred to as a global sequence alignment, may be determined using the FASTDB computer program based on the algorithm of Brutlag, et al., (Comp. App. Biosci. 6:237-245 (1990)). Preferred parameters for a particular embodiment in which identity is narrowly construed, used in a FASTDB amino acid alignment, are: Scoring Scheme=PAM (Percent Accepted Mutations) 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are lateral to the N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence are considered for this manual correction. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for.

For various embodiments of the invention the genetic manipulations may be described to include various genetic manipulations, including those directed to change regulation of, and therefore ultimate activity of, an enzyme or enzymatic activity of an enzyme identified in any of the respective pathways. Such genetic modifications may be directed to transcriptional, translational, and post-translational modifications that result in a change of enzyme activity and/or selectivity under selected and/or identified culture conditions and/or to provision of additional nucleic acid sequences such as to increase copy number and/or mutants of an enzyme related to polyketide production. Specific methodologies and approaches to achieve such genetic modification are well known to one skilled in the art, and include, but are not limited to: increasing expression of an endogenous genetic element; decreasing functionality of a repressor gene; introducing a heterologous genetic element; increasing copy number of a nucleic acid sequence encoding a polypeptide catalyzing an enzymatic conversion step to produce a polyketide; mutating a genetic element to provide a mutated protein to increase specific enzymatic activity; over-expressing; under-expressing; over-expressing a chaperone; knocking out a protease; altering or modifying feedback inhibition; providing an enzyme variant comprising one or more of an impaired binding site for a repressor and/or competitive inhibitor; knocking out a repressor gene; evolution, selection and/or other approaches to improve mRNA stability as well as use of plasmids having an effective copy number and promoters to achieve an effective level of improvement. Random mutagenesis may be practiced to provide genetic modifications that may fall into any of these or other stated approaches. The genetic modifications further broadly fall into additions (including insertions), deletions (such as by a mutation) and substitutions of one or more nucleic acids in a nucleic acid of interest. In various embodiments a genetic modification results in improved enzymatic specific activity and/or turnover number of an enzyme. Without being limited, changes may be measured by one or more of the following: $K_M$; $K_{cat}$; and $K_{avidity}$.

In various embodiments, to function more efficiently, a microorganism may comprise one or more gene deletions. Such gene disruptions, including deletions, are not meant to be limiting, and may be implemented in various combinations in various embodiments. Gene deletions may be accomplished by mutational gene deletion approaches, and/or starting with a mutant strain having reduced or no expression of one or more of these enzymes, and/or other methods known to those skilled in the art. Gene deletions may be effectuated by any of a number of known specific methodologies, including but not limited to the RED/ET methods using kits and other reagents sold by Gene Bridges (Gene Bridges GmbH, Dresden, Germany, <<www.genebridges.com>>).

Targeted deletion of parts of microbial chromosomal DNA or the addition of foreign genetic material to microbial chromosomes may be practiced to alter a host cell's metabolism so as to reduce or eliminate production of undesired metabolic products. This may be used in combination with other genetic modifications such as described herein in this general example. In this detailed description, reference has been made to multiple embodiments and to the accompanying drawings in which is shown by way of illustration specific exemplary embodiments in which the invention may be practiced. These embodiments are described in sufficient detail to enable those skilled in the art to practice the invention, and it is to be understood that modifications to the various disclosed embodiments may be made by a skilled artisan.

Further, for polyketide production, such genetic modifications may be chosen and/or selected for to achieve a higher flux rate through certain enzymatic conversion steps within the respective polyketide production pathway and so may affect general cellular metabolism in fundamental and/or major ways.

It will be appreciated that amino acid "homology" includes conservative substitutions, i.e. those that substitute a given amino acid in a polypeptide by another amino acid of similar characteristics. Typically seen as conservative substitutions are the following replacements: replacements of an aliphatic amino acid such as Ala, Val, Leu and Ile with another aliphatic amino acid; replacement of a Ser with a Thr or vice versa; replacement of an acidic residue such as Asp or Glu with another acidic residue; replacement of a residue bearing an amide group, such as Asn or Gln, with another residue bearing an amide group; exchange of a basic residue such as Lys or Arg with another basic residue; and replacement of an aromatic residue such as Phe or Tyr with another aromatic residue.

For all nucleic acid and amino acid sequences provided herein, it is appreciated that conservatively modified variants of these sequences are included, and are within the scope of the invention in its various embodiments. Functionally equivalent nucleic acid and amino acid sequences (functional variants), which may include conservatively modified variants as well as more extensively varied sequences, which are well within the skill of the person of ordinary skill in the art, and microorganisms comprising these, also are within the scope of various embodiments of the invention, as are methods and systems comprising such sequences and/or microorganisms. In various embodiments, nucleic acid sequences encoding sufficiently homologous proteins or portions thereof are within the scope of the invention. More generally, nucleic acids sequences that encode a particular amino acid sequence employed in the invention may vary due to the degeneracy of the genetic code, and nonetheless fall within the scope of the invention.

As indicated herein, polypeptides having a variant amino acid sequence can retain enzymatic activity. Such polypeptides can be produced by manipulating the nucleotide sequence encoding a polypeptide using standard procedures such as site-directed mutagenesis or various PCRn techniques. As noted herein, one type of modification includes the substitution of one or more amino acid residues for amino acid residues having a similar chemical and/or biochemical property. For example, a polypeptide can have an amino acid sequence set forth in an amino acid sequence listed or otherwise disclosed herein comprising one or more conservative substitutions.

More substantial changes can be obtained by selecting substitutions that are less conservative, and/or in areas of the sequence that may be more critical, for example selecting residues that differ more significantly in their effect on maintaining (a) the structure of the polypeptide backbone in the area of the substitution, for example, as a sheet or helical conformation; (b) the charge or hydrophobicity of the polypeptide at the target site; or (c) the bulk of the side chain. The substitutions that in general are expected to produce the greatest changes in polypeptide function are those in which: (a) a hydrophilic residue, e.g., serine or threonine, is substituted for (or by) a hydrophobic residue, e.g., leucine, isoleucine, phenylalanine, valine or alanine; (b) a cysteine or proline is substituted for (or by) any other residue; (c) a residue having an electropositive side chain, e.g., lysine, arginine, or histidine, is substituted for (or by) an electronegative residue, e.g., glutamic acid or aspartic acid; or (d) a residue having a bulky side chain, e.g., phenylalanine, is substituted for (or by) one not having a side chain, e.g., glycine. The effects of these amino acid substitutions (or other deletions or additions) can be assessed for polypeptides having enzymatic activity by analyzing the ability of the polypeptide to catalyze the conversion of the same substrate as the related native polypeptide to the same product as the related native polypeptide. Accordingly, polypeptides having 5, 10, 20, 30, 40, 50 or less conservative substitutions are provided by the invention.

Compositions of the present invention, such as genetically modified microorganisms, comprise a production pathway for a chemical product in which malonyl-CoA is a substrate, and may also comprise one or more genetic modifications to reduce the activity of enzymes encoded by one or more of the fatty acid synthetase system genes to prevent shunting of this extender into the fatty acid synthesis pathway. The compositions may be used in the methods and systems of the present invention.

The various PKS nucleic acid sequences or nucleotide sequences, or a mixture of such sequences, can be cloned into one or more recombinant vectors as individual cassettes, with separate control elements or under the control of a single promoter. The PKS subunits or components can include flanking restriction sites to allow for the easy deletion and insertion of other PKS subunits. The design of such restriction sites is known to those of skill in the art and can be accomplished using the techniques described above, such as site-directed mutagenesis and PCR. Methods for introducing the recombinant vectors of the present invention into suitable hosts are known to those of skill in the art and typically include the use of $CaCl_2$ or other agents, such as divalent cations, lipofection, DMSO, protoplast transformation, conjugation, and electroporation.

Of the more than thirty PKSs examined, the correspondence between use of modules in the biosynthesis and the structure of the polyketide produced is fully understood both at the level of the protein sequence of the PKS and the DNA sequence of the corresponding genes. The programming of modules into polyketide structure can be identified by sequence determination. It is possible to clone (or synthesize) DNA sequences corresponding to desired modules and transfer them as fully functioning units to heterologous, otherwise non-polyketide producing hosts such as *E. coli* (Pfeifer, et al., *Science* 291:1790 (2001)) and *Streptomyces* (Kao, et al., *Science* 265:509 (1994)). Additional genes employed for polyketide biosynthesis have also been identified. Genes that determine phosphopantetheine:protein transferase (PPTase) that transfer the 4-phosphopantetheine cofactor of the ACP domains, commonly present in polyketide producing hosts, have been cloned in *E. coli* and other hosts (Weissman, et al., *Chembiochem* 5:116 (2004)). Moreover, genes for the production of precursors such as methylmalonyl CoA and ethylmalonyl CoA have also been identified and cloned in heterologous hosts. It is also possible to re-program polyketide biosynthesis to produce a compound of desired structure by either genetic manipulation of a single PKS or by construction of a hybrid PKS composed of modules from two or more sources (Weissman, et al., *Chembiochem* 5:116 (2004)).

Recombinant methods for manipulating modular PKS genes to make the PKSs of the present invention are described in U.S. Pat. Nos. 5,672,491; 5,843,718; 5,830,750; 5,712,146; and 6,303,342; and in PCT publication Nos. WO 98/49315 and WO 97/02358; hereby incorporated by reference. A number of genetic engineering strategies have been used with various PKSs to demonstrate that the structures of polyketides can be manipulated to produce novel polyketides (see the patent publications referenced supra and Hutchinson, 1998, *Curr Opin Microbiol.* 1:319-329, and Baltz, 1998, *Trends Microbiol.* 6:76-83; hereby incorporated by reference). In some embodiment, the components of the hybrid PKS are arranged onto polypeptides having interpolypeptide linkers that direct the assembly of the polypeptides into the functional PKS protein, such that it is not required that the PKS have the same arrangement of modules in the polypeptides as observed in natural PKSs. Suitable interpolypeptide linkers to join polypeptides and intrapolypeptide linkers to join modules within a polypeptide are described in PCT publication No. WO 00/47724, hereby incorporated by reference.

The vast number of polyketide pathways that have been elucidated provide a host of different options to produce the halogenated compounds of the present invention. While the products can be vastly different in size and functionality, all employ virtually the same strategy for biosynthesis. In an exemplary embodiment, the exact interfaces between non-cognate enzyme partners are determined on a case-by-case basis. ACP-linker-KS and ACP-linker-TE regions from the proteins of interest are aligned to examine the least disruptive fusion point for the hybrid synthase. Genetic constructions employ sequence and ligation independent cloning (SLIC) so as to eliminate the incorporation of genetic "scarring".

A partial list of sources of PKS sequences that can be used in making the PKSs of the present invention, for illustration and not limitation, includes Ambruticin (U.S. Pat. No. 7,332,576); Avermectin (U.S. Pat. No. 5,252,474; MacNeil, et al., 1993, Industrial Microorganisms: Basic and Applied Molecular Genetics, Baltz, Hegeman, & Skatrud, eds. (ASM), pp. 245-256; MacNeil, et al., 1992, *Gene* 115: 119-25); Candicidin (FR0008) (Hu, et al., 1994, *Mol. Microbiol.* 14:163-72); Epothilone (U.S. Pat. No. 6,303,342); Erythromycin (WO 93/13663; U.S. Pat. No. 5,824,513; Donadio, et al., 1991, *Science* 252:675-79; Cortes, et al., 1990, *Nature* 348:176-8); FK506 (Motamedi, et al., 1998, *Eur. J. Biochem.* 256:528-34; Motamedi, et al., 1997, *Eur. J. Biochem.* 244:74-80); FK520 or ascomycin (U.S. Pat. No. 6,503,737; see also Nielsen, et al., 1991, *Biochem.* 30:5789-96); Jerangolid (U.S. Pat. No. 7,285,405); Leptomycin (U.S. Pat. No. 7,288,396); Lovastatin (U.S. Pat. No. 5,744,350); Nemadectin (MacNeil, et al., 1993, supra); Niddamycin (Kakavas, et al., 1997, *J. Bacteriol.* 179:7515-22); Oleandomycin (Swan, et al., 1994, *Mol. Gen. Genet.* 242:358-62; U.S. Pat. No. 6,388,099; Olano, et al., 1998, *Mol. Gen. Genet.* 259:299-308); Oligomycin (Omura, et al., J., 2001, *Proc. Natl. Acad. Sci. USA* 98:12215-12220); Pederin (PCT publication No. WO 2003/044186); Pikromycin (Xue, et al., 2000, *Gene* 245:203-211); Pimaricin (PCT publication No. WO 2000/077222); Platenolide (EP Pat. App. 791,656); Rapamycin (Schwecke, et al., 1995, *Proc. Natl. Acad. Sci. USA* 92:7839-43); Aparicio, et al., 1996, *Gene* 169:9-16); Rifamycin (August et al., 1998, *Chemistry & Biology*, 5: 69-79); Soraphen (U.S. Pat. No. 5,716,849; Schupp, et al., 1995, *J. Bacteriology* 177: 3673-79); Spiramycin (U.S. Pat. No. 5,098,837); Tylosin (EP 0 791,655; Kuhstoss et al., 1996, *Gene* 183:231-36; U.S. Pat. No. 5,876,991). Additional suitable PKS coding sequences are readily available to one skilled in the art, or remain to be discovered and characterized, but will be available to those of skill (e.g., by reference to GenBank). Each of the references cited is hereby specifically and individually incorporated by reference.

Products produced by the methods of the invention include complex polyketides. Complex polyketides comprise a large class of natural products that are synthesized in bacteria (mainly members actinomycete family; e.g. *Streptomyces*), fungi and plants. Polyketides form the aglycone component of a large number of clinically important drugs, such as antibiotics (e.g., erythromycin, tylosin), antifungal agents (e.g., nystatin), anticancer agents (e.g., epothilone), immunosuppressives (e.g., rapamycin), etc. Though these compounds do not resemble each other either in their structure or their mode of action, they share a common basis for their biosynthesis, which is carried out by a group of enzymes designated polyketide synthases.

The assembly of a loading module and at least two extender modules can be done in *E. coli*. Compounds requiring halogenated acetyl CoA or halogenated malonyl CoA as precursors can be made in *E. coli* hosts. The modules can also be cloned in vectors that can be introduced into a variety of *Streptomyces* hosts (e.g., *Streptomyces coelicolor*).

Compounds requiring propionate (methylmalonate) precursors can be made in a variety of *Streptomyces* hosts which have ample supplies of these precursors. Alternatively, *E. coli* can be fed with propionate and the enzyme methylmalonyl CoA mutase can be cloned in an *E. coli* host engineered to incorporate vitB 12.

Compounds which require module J for their synthesis will contain an ethyl side chain and will employ 2-ethylmalonyl CoA as a precursor. Ethylmalonate is produced from the isomerization of butyrate. The genes encoding the enzymes in this pathway to produce this precursor can be cloned into in a suitable *E. coli*. Numerous streptomycetes exist that produce ethylmalonyl CoA, some of which are suitable for cloning and expression of PKS genes (e.g., *Streptomyces fradiae*).

Host Microorganisms

Generally, a microorganism used for the present invention may be selected from bacteria, cyanobacteria, filamentous fungi and yeasts.

For some embodiments, microbial hosts initially selected should also utilize sugars including glucose at a high rate. Most microbes are capable of utilizing carbohydrates. However, certain environmental microbes cannot utilize carbohydrates to high efficiency, and therefore would not be suitable hosts for such embodiments that are intended for glucose or other carbohydrates as the principal added carbon source.

As the genomes of various species become known, the present invention may be easily applied to an ever-increasing range of suitable microorganisms. Further, given the relatively low cost of genetic sequencing, the genetic sequence of a species of interest may readily be determined to make application of aspects of the present invention more readily obtainable (based on the ease of application of genetic modifications to an organism having a known genomic sequence). Such modifications are within the scope of the invention.

Based on the various criteria described herein, suitable microbial hosts for the bio-production of polyketides include, but are not limited to, any gram negative organisms, more particularly a member of the family Enterobacteriaceae, such as *E. coli*, or *Oligotropha carboxidovorans*, or *Pseudomononas* sp.; any gram positive microorganism, for example *Bacillus subtilis, Lactobaccilus* sp. or *Lactococcus* sp.; a yeast, for example *Saccharomyces cerevisiae, Pichia pastoris* or *Pichia stipitis*; and other groups or microbial species.

In some embodiments a recombinant microorganism is utilized.

Media and Culture Conditions

In addition to an appropriate carbon source, bio-production media must contain suitable minerals, salts, cofactors, buffers and other components, known to those skilled in the art, suitable for the growth of the cultures and promotion of the enzymatic pathway necessary for polyketide production, or other products made under the present invention.

Another aspect of the invention regards media and culture conditions that comprise genetically modified microorganisms of the invention and optionally supplements.

Typically cells are grown at a temperature in the range of about 25° C. to about 40° C. in an appropriate medium, as well as up to 70° C. for thermophilic microorganisms. Suitable growth media in the present invention are common commercially prepared media such as Luria Bertani (LB) broth, M9 minimal media, Sabouraud Dextrose (SD) broth, Yeast medium (YM) broth, (Ymin) yeast synthetic minimal media, and minimal media as described herein, such as M9 minimal media. Other defined or synthetic growth media may also be used, and the appropriate medium for growth of the particular microorganism will be known by one skilled in the art of microbiology or bio-production science. In various embodiments a minimal media may be developed and used that does not comprise, or that has a low level of addition of various components, for example less than 10, 5, 2 or 1 g/L of a complex nitrogen source including but not limited to yeast extract, peptone, tryptone, soy flour, corn steep liquor, or casein. These minimal medias may also have limited supplementation of vitamin mixtures including biotin, vitamin B 12 and derivatives of vitamin B 12, thiamin, pantothenate and other vitamins. Minimal medias may also have limited simple inorganic nutrient sources containing less than 28, 17, or 2.5 mM phosphate, less than 25 or 4 mM sulfate, and less than 130 or 50 mM total nitrogen.

Bio-production media, which is used in embodiments of the present invention with genetically modified microorganisms, must contain suitable carbon substrates for the intended metabolic pathways. As described hereinbefore, suitable carbon substrates include carbon monoxide, carbon dioxide, and various monomeric and oligomeric sugars.

Suitable pH ranges for the bio-production of polyketides are between pH 3.0 to pH 10.0, where pH 6.0 to pH 8.0 is a typical pH range for the initial condition. However, the actual culture conditions for a particular embodiment are not meant to be limited by these pH ranges.

Bio-production of polyketides may be performed under aerobic, microaerobic, or anaerobic conditions, with or without agitation.

The amount of polyketide or other product(s), produced in a bio-production media generally can be determined using a number of methods known in the art, for example, high performance liquid chromatography (HPLC), gas chromatography (GC), GC/Mass Spectroscopy (MS), or spectrometry.

Bio-Production Reactors and Systems

Fermentation systems utilizing methods and/or compositions according to the invention are also within the scope of the invention.

Any of the microorganisms as described and/or referred to herein may be introduced into an industrial bio-production system where the microorganisms convert a carbon source into a selected chemical product, such as a polyketide, in a commercially viable operation. The bio-production system includes the introduction of such a microorganism into a bioreactor vessel, with a carbon source substrate and bio-production media suitable for growing the recombinant microorganism, and maintaining the bio-production system within a suitable temperature range (and dissolved oxygen concentration range if the reaction is aerobic or microaerobic) for a suitable time to obtain a desired conversion of a portion of the substrate molecules to a polyketide. Industrial bio-production systems and their operation are well-known to those skilled in the arts of chemical engineering and bioprocess engineering.

Bio-productions may be performed under aerobic, microaerobic, or anaerobic conditions, with or without agitation. The operation of cultures and populations of microorganisms to achieve aerobic, microaerobic and anaerobic conditions are known in the art, and dissolved oxygen levels of a liquid culture comprising a nutrient media and such microorganism populations may be monitored to maintain or confirm a desired aerobic, microaerobic or anaerobic condition. When syngas is used as a feedstock, aerobic, microaerobic, or anaerobic conditions may be utilized. When sugars are used, anaerobic, aerobic or microaerobic conditions can be implemented in various embodiments.

Further to types of industrial bio-production, various embodiments of the present invention may employ a batch type of industrial bioreactor. A classical batch bioreactor system is considered "closed" meaning that the composition of the medium is established at the beginning of a respective bio-production event and not subject to artificial alterations and additions during the time period ending substantially with the end of the bio-production event. Thus, at the beginning of the bio-production event the medium is inoculated with the desired organism or organisms, and bio-production is permitted to occur without adding anything to the system. Typically, however, a "batch" type of bio-production event is batch with respect to the addition of carbon source and attempts are often made at controlling factors such as pH and oxygen concentration. In batch systems the metabolite and biomass compositions of the system change constantly up to the time the bio-production event is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of a desired end product or intermediate.

A variation on the standard batch system is the fed-batch system. Fed-batch bio-production processes are also suitable in the present invention and comprise a typical batch system with the exception that the nutrients, including the substrate, are added in increments as the bio-production progresses. Fed-batch systems are useful when catabolite repression is apt to inhibit the metabolism of the cells and where it is desirable to have limited amounts of substrate in the media. Measurement of the actual nutrient concentration in Fed-Batch systems may be measured directly, such as by sample analysis at different times, or estimated on the basis of the changes of measurable factors such as pH, dissolved oxygen and the partial pressure of waste gases such as $CO_2$. Batch and fed-batch approaches are common and well known in the art and examples may be found in Thomas D. Brock in Biotechnology: A Textbook of Industrial Microbiology, Second Edition (1989) Sinauer Associates, Inc., Sunderland, Mass., Deshpande, Mukund V., *Appl. Biochem. Biotechnol.*, 36:227, (1992), and Biochemical Engineering Fundamentals, 2nd Ed. J. E. Bailey and D. F. Ollis, McGraw Hill, New York, 1986, herein incorporated by reference for general instruction on bio-production.

In various embodiments, the invention is directed to a system for bioproduction of a polyketide as described herein. An exemplary system comprises: a fermentation tank suitable for microorganism cell culture; a line for discharging contents from the fermentation tank to an extraction and/or separation vessel; an extraction and/or separation vessel suitable for removal of a polyketide from cell culture waste; a line for transferring polyketide to a dehydration vessel; and a dehydration vessel suitable for conversion of wet polyketide to dry polyketide. In various embodiments, the system includes one or more pre-fermentation tanks, distillation columns, centrifuge vessels, back extraction columns, mixing vessels, or combinations thereof.

The following examples are offered to illustrate certain embodiments of the invention and are not to be construed as limiting the invention to these embodiments.

EXAMPLES

Example 1

Materials and Methods
Commercial Materials.
Luria-Bertani (LB) Broth Miller, LB Agar Miller, Terrific Broth (TB), yeast extract, malt extract, glycerol, and triethylamine (TEA) were purchased from EMD Biosciences (Darmstadt, Germany). Carbenicillin (Cb), isopropyl-D-thiogalactopyranoside (IPTG), phenylmethanesulfonyl fluoride (PMSF), tris(hydroxymethyl)aminomethane hydrochloride (Tris-HCl), sodium chloride, dithiothreitol (DTT), 4-(2-hydroxyethyl)-1-piperazineethanesulfonic acid (HEPES), magnesium chloride hexahydrate, kanamycin (Km), acetonitrile, N,O-bis(trimethylsilyl)trifluoroacetamide (BSTFA), dichloromethane, ethyl acetate and ethylene diamine tetraacetic acid disodium dihydrate (EDTA), were purchased from Fisher Scientific (Pittsburgh, Pa.). S odium fluoroacetate, coenzyme A trilithium salt (CoA), acetyl-CoA, malonyl-CoA, methylmalonyl-CoA, diethylfluoromalonate, malonic acid, methylmalonic acid, tris(2-carboxyethyl)phosphine (TCEP) hydrochloride, lithium hexamethyldisilazide solution (LiHMDS), phosphoenolpyruvate (PEP), adenosine triphosphate sodium salt (ATP), nicotinamide adenine dinucleotide reduced form dipotassium salt (NADH), nicotinamide adenine dinucleotide phosphate reduced form (NADPH), myokinase, pyruvate kinase, lactate dehydrogenase, poly(ethyleneimine) solution (PEI), 5-fluorouracil, β-mercaptoethanol, sodium phosphate dibasic hepthydrate, chlorotrifluoromethane and N,N,N',N'-tetramethyl-ethane-1,2-diamine (TEMED) were purchased from Sigma-Aldrich (St. Louis, Mo.). Formic acid was purchased from Acros Organics (Morris Plains, N.J.). Acrylamide/Bis-acrylamide (30%, 37.5:1), electrophoresis grade sodium dodecyl sulfate (SDS), Bio-Rad protein assay dye reagent concentrate and ammonium persulfate were purchased from Bio-Rad Laboratories (Hercules, Calif.). Restriction enzymes, T4 DNA ligase, Antarctic phosphatase, Phusion DNA polymerase, T5 exonuclease, and Taq DNA ligase were purchased from New England Biolabs (Ipswich, Mass.). Deoxynucleotides (dNTPs) and Platinum Taq High-Fidelity polymerase (Pt Taq HF) were purchased from Invitrogen (Carlsbad, Calif.). PageRuler™ Plus prestained protein ladder was purchased from Fermentas (Glen Burnie, Md.). Oligonucleotides were purchased from Integrated DNA Technologies (Coralville, Iowa), resuspended at a stock concentration of 100 μM in 10 mM Tris-HCl, pH 8.5, and stored at either 4° C. for immediate use or −20° C. for longer term use. DNA purification kits and Ni-NTA agarose were purchased from Qiagen (Valencia, Calif.). Complete EDTA-free protease inhibitor was purchased from Roche Applied Science (Penzberg, Germany). O-(7-Azabenzotriazol-1-yl)-N,N,N',N'-tetramethyluronium hexafluorophosphate (HATU), Amicon Ultra 3,000 MWCO and 30,000 MWCO centrifugal concentrators, 5,000 MWCO regenerated cellulose ultrafiltration membranes, and LiChroCART 250-4 Purospher RP-18e HPLC column were purchased from EMD Millipore (Billerica, Mass.). Deuterium oxide and chloroform-d were purchased from Cambridge Isotope Laboratories (Andover, Mass.). $^{19}F$ NMR spectra were collected at 25° C. on Bruker AVQ-400 or AV-600 spectrometers at the College of Chemistry NMR Facility at the University of California, Berkeley or on a Bruker Biospin 900 MHz spectrometer at the QB3 Central California 900 MHz NMR Facility or on a Bruker AV-600 spectrometer equipped with a QCI-CryoProbe at Novartis Institutes for Biomedical Research (Emeryville, Calif.). Spectra were referenced to $CFCl_3$ (0 ppm) or 5-fluorouracil ($D_2O$: −168.33 ppm vs. $CFCl_3$). NMR assignments were made based on COSY, $^{13}C$-$^1H$ HSQC, $^{13}C$-$^1H$ HMBC and $^{19}F$-$^1H$ HMBC spectra where appropriate. High-resolution mass spectral analyses were carried out at the College of Chemistry Mass Spectrometry Facility.

Bacterial Strains.
*E. coli* DH10B-T1$^R$ and BL21(de3)T1$^R$ were used for DNA construction and heterologous protein production, respectively, except for DEBS modules, which were heterologously expressed in *E. coli* BAP1 (Pfeifer, B. A., et al., *Science* 291:1790-1792 (2001)).

Gene and Plasmid Construction.
Standard molecular biology techniques were used to carry out plasmid construction. All PCR amplifications were carried out with Phusion or Platinum Taq High Fidelity DNA polymerases. For amplification of GC-rich sequences from *S. coelicolor*, PCR reactions were supplemented with DMSO (5%) using the standard buffer rather than GC buffer with primer annealing temperatures 8-10° C. below the $T_m$. All constructs were verified by sequencing (Quintara Biosciences; Berkeley, Calif.).

The synthetic gene encoding NphT7 was optimized for *E. coli* class II codon usage and synthesized using PCR assembly (Table S1). Gene2Oligo was used to convert the gene sequence into primer sets using default optimization settings (Table S1) (Rouillard, J. M., et al., *Nucleic Acids Res.* 32:W176-W180 (2004)). To assemble the synthetic gene, each primer was added at a final concentration of 1 µM to the first PCR reaction (50 µL) containing 1×Pt Taq HF buffer (20 mM Tris-HCl, 50 mM KCl, pH 8.4), MgSO$_4$ (1.5 mM), dNTPs (250 µM each), and Pt Taq HF (5 U). The following thermocycler program was used for the first assembly reaction: 95° C. for 5 min; 95° C. for 30 s; 55° C. for 2 min; 72° C. for 10 s; 40 cycles of 95° C. for 15 s, 55° C. for 30 s, 72° C. for 20 s plus 3 s/cycle; these cycles were followed by a final incubation at 72° C. for 5 min. The second assembly reaction (50 µL) contained 16 ΞL of the unpurified first PCR reaction with standard reagents for Pt Taq HF. The thermocycler program for the second PCR was: 95° C. for 30 s; 55° C. for 2 min; 72° C. for 10 s; 40 cycles of 95° C. for 15 s, 55° C. for 30 s, 72° C. for 80 s; these cycles were followed by a final incubation at 72° C. for 5 min. The second PCR reaction (16 µL) was transferred again into fresh reagents and run using the same program. Following gene construction, the DNA smear at the appropriate size was gel purified and used as a template for the rescue PCR (50 µL) with Pt Taq HF and rescue primers under standard conditions. The resulting rescue product was inserted into pBAD33 and confirmed by sequencing, then amplified using the nphT7 F1/R1 primer set (Table S1) and inserted into the NdeI site of pET-16b using the Gibson protocol (Gibson, D. G., et al., *Nat. Methods*, 6:343-345 (2009)).

pET16b-His$_{10}$-AckA.EC and pET16b-His$_{10}$-Pta.EC were constructed by amplification from pRSFDuet-ackA.pta using the AckA.EC F/R and Pta.EC F/R primer sets (Table S1) and insertion into the NdeI-XhoI (Pta, Gene ID 12872491) or NdeI-BamHI (AckA, Gene ID 12874027) sites of pET16b. pET28a-His$_6$-MatB.SCo and pET28a-His$_6$-Epi.SCo were constructed by amplification from *S. coelicolor* A3(2) M145 (ATCC BAA-471) genomic DNA using the MatB.SCo F/R and epi.SCo F/R primer sets (Table S1) and insertion into the NdeI-XhoI sites of pET28a. pET16x-His$_{10}$-THNS was constructed by amplification out of *S. coelicolor* genomic DNA using the THNS F/R primer set (Table S1) and insertion into the NdeI-SpeI sites of pET16x. pCDFDuet-DszsAT.SCe-MatB.SCo and pCDFDuet-ø-MatB.SCo were constructed by amplification from pET28a-His$_6$-MatB.SCo and pFW3 (Wong, F. T., et al., *Biochemistry*, 49:95-102 (2009)) using the pCDF-MatB.SCo F/R and pCDF-DszsAT.SCe F/R primer sets (Table S1) and insertion of DszsAT.SCe and MatB.SCo into the NcoI-HindIII and NdeI-KpnI sites of pCDFDuet-1 respectively. pTRC33-NphT7-PhaB was constructed by amplifying NphT7 from pET-16b-NphT7 using the NphT7 G F/G R primer set (Table S1) and PhaB from pBT33-PhaABC (Bond-Watts, B. B., et al., *Nat. Chem. Biol.*, 7:222-227 (2011)) using the PhaB F/R primer set (Table S1) where each forward primer included the RBS from pET16b, then inserting both genes simultaneously into the BamHI-XbaI sites of pTRC33 using the Gibson protocol. pSV272-His$_6$-MBP-DEBS$_{Mod2}$ and pSV272-His$_6$-MBP-DEBS$_{Mod2}$/AT$^0$ (S2652A based on EryAI numbering) were constructed by amplification from pBP19 (Tsuji, S. Y., et al., *Biochemistry*, 40:2326-2331 (2001)) using the MBP-M2 F/R primer set (pSV272-MBP-DEBS$_{Mod2}$-His$_6$) (Table S1) or MBP-M2 F/MBP-M2ATnull R and MBP-M2ATnull F/MBP-M2 R (pSV272-MBP-DEBS$_{Mod2}$/AT$^0$-His$_6$) (Table S1) and insertion into the SfoI-HindIII sites of pSV272.1 using the Gibson protocol. pBAD33.BirA.EC was cloned by the QB3 Macrolab.

Expression of his-Tagged Proteins.

TB (1 L) containing carbenicillin, kanamycin, and chloramphenicol (50 µg/mL) as appropriate in a 2.8 L Fernbach baffled shake flask was inoculated to OD$_{600}$=0.05 with an overnight TB culture of freshly transformed *E. coli* containing the appropriate overexpression plasmid. The cultures were grown at 37° C. at 250 rpm to OD$_{600}$=0.6 to 0.8 at which point cultures were cooled on ice for 20 min, followed by induction of protein expression with IPTG (His$_{10}$-AckA, His$_{10}$-Pta: 1 mM; His$_{10}$-AccA/B/C/D, His$_{10}$-THNS, DEBS$_{Mod6}$/AT$^0$+TE-His$_6$[pAYC138, (Wong, F. T., et al., *Biochemistry*, 49:95-102 (2009))]: 0.4 mM; His$_6$-MatB, His$_6$-Epi, His$_{10}$-NphT7, DszsAT-His$_6$[pFW3, (Wong, F. T., et al., *Biochemistry*, 49:95-102 (2009))], DEBS$_{Mod6}$+TE-His$_6$[pRSG54, (Wu, N., et al., *J. Am. Chem. Soc.*, 122:4847-4852 (2000))], DEBS$_{Mod3}$+TE-His$_6$[pRSG34, (Gokhale, R. S., et al., *Science*, 284:482-485 (1999))], DEBS$_{Mod3}$/AT$^0$+TE-His$_6$[pAYC136, (Wong, F. T., et al., *Biochemistry*, 49:95-102 (2009))], MBP-DEBS$_{Mod2}$-His$_6$, MBP-DEBS$_{Mod2}$/AT$^0$-His$_6$: 0.2 mM) and overnight growth at 16° C. For His$_{10}$-AccB expression, pBAD33-BirA was co-expressed (L-arabinose, 0.2%) and the medium was supplemented with 20 nM D-(+)-biotin at induction. For MBP-DEBS$_{Mod2}$-His$_6$ and MBP-DEBS$_{Mod2}$/AT$^0$-His$_6$, pRARE2 was co-expressed. Cell pellets were harvested by centrifugation at 9,800×g for 7 min at 4° C. and stored at −80° C.

Purification of His$_{10}$-AckA, His$_{10}$-Pta, His$_6$-MatB, His$_6$-Epi, His$_{10}$-AccA/B/C/D, DszsAT-His$_6$ and His$_{10}$-NphT7.

Frozen cell pellets were thawed and resuspended at 5 mL/g cell paste with Buffer A (50 mM sodium phosphate, 300 mM sodium chloride, 20% glycerol, 20 mM BME, pH 7.5) containing imidazole (10 mM) for His$_{10}$-AckA, His$_{10}$-Pta, His$_{10}$-AccA/B/C/D, His$_{10}$-NphT7, and DszsAT-His$_6$ or Buffer B (200 mM sodium phosphate, 200 mM sodium chloride, 30% glycerol, 2.5 mM EDTA, 2.5 mM DTT, pH 7.5) for His$_6$-MatB and His$_6$-Epi. Complete EDTA-free protease inhibitor cocktail (Roche) was added to the lysis buffer before resuspension. The cell paste was homogenized before lysis by passage through a French Pressure cell (Thermo Scientific; Waltham, Mass.) at 14,000 psi. The lysate was centrifuged at 15,300×g for 20 min at 4° C. to separate the soluble and insoluble fractions. DNA was precipitated in the soluble fraction by addition of 0.15% (w/v) poly(ethyleneimine). The precipitated DNA was removed by centrifugation at 15,300×g for 20 min at 4° C. The remaining soluble lysate was diluted three-fold with Buffer A containing imidazole (10 mM) and loaded onto a Ni-NTA agarose column (Qiagen, 1 mL resin/g cell paste) by gravity flow or on an AKTApurifier FPLC (2 mL/min; GE Healthcare; Piscataway, N.J.). The column was washed with Buffer A until the eluate reached an A$_{280\ nm}$<0.05 or was negative for protein content by Bradford assay (Bio-Rad).

His$_{10}$-AckA, His$_{10}$-Pta, His$_6$-MatB, His$_{10}$-AccB, His$_{10}$-AccD, and DszsAT-His$_6$.

The column was washed with 5 to 10 column volumes with Buffer A supplemented with imidazole (His$_{10}$-AckA, 40 mM; His$_{10}$-Pta, 35 mM; His$_6$-MatB, His$_{10}$-AccB, His$_{10}$-AccD, and DszsAT-His$_6$, 20 mM). The protein was then eluted with 300 mM imidazole in Buffer A.

His$_6$-Epi.

His$_6$-Epi was eluted using a linear gradient from 0 to 300 mM imidazole in Buffer A over 30 column volumes.

His$_{10}$-AccA, His$_{10}$-AccC and His$_{10}$-NphT7.

The column was washed with a linear gradient from 10 to 90 mM imidazole in Buffer A over 15 column volumes and then eluted with 300 mM imidazole in Buffer A.

Fractions containing the target protein were pooled by $A_{280\,nm}$ and concentrated using either an Amicon Ultra spin concentrator (3 kDa MWCO, Millipore) or an Amicon ultrafiltration cell under nitrogen flow (65 psi) using a membrane with an appropriate nominal molecular weight cutoff (Ultracel-5 or YM10, Millipore). Protein was then exchanged into Buffer C (50 mM HEPES, 100 mM sodium chloride, 2.5 mM EDTA, 20% glycerol, pH 7.5) with ($His_{10}$-AckA, $His_{10}$-Pta, $His_{10}$-AccA/B/C/D, $His_{10}$-NphT7, DszsAT-$His_6$) or without ($His_6$-MatB and $His_6$-Epi) DTT (0.5-1 mM) using a Sephadex G-25 column (Sigma-Aldrich, bead size 50-150 μm, 10 mL resin/mL protein solution), then concentrated again before storage.

Final protein concentrations before storage were estimated using the $A_{280\,nm}$ calculated by ExPASY ProtParam as follows: $His_{10}$-AckA: 14.8 mg/mL ($A_{280\,nm}$=24,860 $M^{-1}$ $cm^{-1}$), $His_{10}$-Pta: 16.5 mg/mL ($A_{280\,nm}$=37,360 $M^{-1}$ $cm^{-1}$), $His_6$-MatB: 19.8 mg/mL ($A_{280\,nm}$=33,920 $M^{-1}$ $cm^{-1}$), $His_6$-Epi: 18.5 mg/mL ($A_{280\,nm}$=11,460 $M^{-1}$ $cm^{-1}$), $His_{10}$-AccA: 33.2 mg/mL ($v_{280\,nm}$=25,900 $M^{-1}$ $cm^{-1}$), $His_{10}$-AccB: 23.0 mg/mL ($A_{280\,nm}$=2,980 $M^{-1}$ $cm^{-1}$), $His_{10}$-AccC: 32.6 mg/mL ($A_{280\,nm}$=27,850 $M^{-1}$ $cm^{-1}$), $His_{10}$-AccD: 4.5 mg/mL ($A_{280\,nm}$=16,960 $M^{-1}$ $cm^{-1}$), DszsAT-$His_6$: 1.7 mg/mL ($V_{280\,nm}$=17,420 $M^{-1}$ $cm^{-1}$), $His_{10}$-NphT7: 0.4 mg/mL ($V_{280\,nm}$=26,930 $M^{-1}$ $cm^{-1}$). All proteins were aliquoted, flash-frozen in liquid nitrogen, and stored at −80° C.

Purification of $DEBS_{Mod6}$+TE-$His_6$, $DEBS_{Mod6}$/$AT^0$+TE-$His_6$, $DEBS_{Mod3}$+TE-$His_6$, and $DEBS_{Mod3}$/$AT^0$+TE-$His_6$.

The His-tagged DEBS module with thioesterase ($DEBS_{Mod6}$+TE) construct was heterologously expressed in *E. coli* BAP1 pRSG54 as described previously and purified using a modified literature protocol (Kumar, et al., *Method. Enzymol.*, 269-293 (2004)). Cleared cell lysates were prepared in Buffer B as described above, diluted three-fold with Buffer A, and passed over a Ni-NTA agarose column (Qiagen, approximately 1 mL/g cell paste) on an ÄKTApurifier FPLC. The column was washed with Buffer A until the eluate reached an $A_{280\,nm}$<0.05. Protein was eluted with Buffer D (50 mM sodium phosphate, 50 mM sodium chloride, 20 mM BME, 20% glycerol, 100 mM imidazole, pH 7.5). The eluate was diluted three-fold with Buffer E (50 mM HEPES, 2.5 mM EDTA, 2.5 mM DTT, 20% glycerol, pH 7.5), loaded onto a HiTrap Q HP column (GE Healthcare, 5 mL), and eluted with a linear gradient from 0 to 1 M sodium chloride in Buffer E over 30 column volumes (4.5 mL/min) Fractions containing the target protein (eluted at 350 mM sodium chloride) were pooled by $A_{280\,nm}$ and concentrated under nitrogen flow (65 psi) in an Amicon ultrafiltration cell using a YM10 membrane. The protein was flash-frozen in liquid nitrogen and stored at −80° C. at a final concentration of 6-30 mg/mL, which was estimated using the calculated $A_{280\,nm}$ ($DEBS_{moo}$ and $DEBS_{moo}$/$AT^0$: 203,280 $M^{-1}$ $cm^{-1}$; $DEBS_{Mod6}$ and $DEBS_{Mod6}$/$AT^0$: 206,260 $M^{-1}$ $cm^{-1}$).

Purification of MBP-$DEBS_{Mod2}$-$His_6$ and MBP-$DEBS_{Mod2}$/$AT^0$-$His_6$.

Cleared lysates were prepared as described for other DEBS modules, diluted three-fold with Buffer A containing 10 mM imidazole, and bound in batch to Ni-NTA resin (2.5 mL/g cell paste) for 2 h. The slurry was poured into a fitted column and washed with Buffer A containing 10 mM imidazole until the eluate reached $A_{280\,nm}$<0.05. The protein was eluted with Buffer A containing 300 mM imidazole and concentrated to 1 mg/mL in an Amicon ultrafiltration cell using a YM10 (30 kD NMWL) membrane. The protein was then dialyzed overnight against Buffer E containing 50 mM NaCl with TEV protease (1 mg/100 mg protein substrate) to remove the MBP tag. The protein was loaded onto a HiTrap Q HP column and eluted by a linear gradient from 0 to 500 mM NaCl in Buffer E over 20 column volumes. Fractions containing the desired protein were identified by SDS-PAGE (eluting at 350 mM NaCl), pooled, and concentrated in a YM10 (30 kD NMWL) Amicon Ultra spin concentrator. Protein aliquots were flash-frozen in liquid nitrogen and stored at −80° C. at a final concentration of 20-25 mg/mL, which was estimated using the calculated $A_{280\,nm}$ (158,360 $M^{-1}$ $cm^{-1}$).

Purification of $His_{10}$-THNS.

$His_{10}$-THNS was purified according to a modified literature procedure (Izumikawa, M., et al., *J. Ind. Microbiol. Biot.*, 30:510-515 (2003)). Cleared cell lysates were prepared in Buffer F (50 mM Tris-HCl, 500 mM sodium chloride, 20 mM BME, 10% glycerol pH 8) supplemented with imidazole (10 mM), PMSF (0.75 mM), and Tween 20 (1% v/v) as described above, diluted with Buffer G containing imidazole (10 mM) and Tween 20 (1%), and loaded onto a HisTrap FF column (GE Healthcare, 1 mL) on an AKTApurifier FPLC (1 mL/min) The column was washed with 10 mM followed by 20 mM imidazole in Buffer G, each time until the eluate reached an $A_{280\,nm}$<0.05. Protein was eluted with 300 mM imidazole in Buffer G and concentrated with an Amicon Ultra spin concentrator (10 kDa MWCO). $His_{10}$-THNS was then exchanged into Buffer C containing DTT (1 mM) using a Sephadex G-25 column (Sigma-Aldrich, bead size 50-150 μm, 10 mL/mL protein solution) and concentrated again. The protein was flash-frozen in liquid nitrogen and stored at −80° C. at a final concentration of 4.4 mg/mL, which was estimated using the calculated $A_{280\,nm}$ (33,920 $M^{-1}$ $cm^{-1}$).

ESI-MS screening method for acyl-CoAs. Preparative HPLC fractions were screened on an Agilent 1290 HPLC system using a Zorbax Eclipse Plus C-18 column (3.5 lam, 2.1×30 mm, Agilent) with a linear gradient from 0 to 65% acetonitrile over 2 min with 0.1% formic acid as the aqueous mobile phase (0.75 mL/min) Mass spectra were recorded on an Agilent 6130 single quadrupole MS with ESI source, operating in negative and positive ion scan mode.

Fluoromalonate.

Diethylfluoromalonate (0.5 mL, 3.2 mmol) was saponified with methanolic sodium hydroxide (2 M, 3.5 mL) in dichloromethane and methanol (9:1 v/v, 32 mL) and the sodium salt isolated by filtration through a Büchner funnel with a fine porosity glass frit (Theodorou, V., et al., *Tetrahedron Lett.*, 48:8230-8233 (2007)). $^{19}F$ NMR (565 MHz, $D_2O$, 5-fluorouracil=−168.3 ppm): δ −176.43 (d, J=53 Hz).

Fluoromalonyl-CoA.

Fluoromalonyl-CoA was prepared enzymatically from fluoromalonate and CoA using MatB and ATP. A myokinase/pyruvate kinase/PEP system was also used to regenerate ATP in order to avoid high concentrations of AMP that might inhibit MatB. The reaction mixture (10 mL) contained 100 mM sodium phosphate, pH 7.5, phosphoenolpyruvate (5 mM), TCEP (2.5 mM), magnesium chloride (5 mM), fluoromalonate (2.5 mM), ATP (2.5 mM), pyruvate kinase (36 U), myokinase (20 U), CoA (2 mM) and MatB (5 μM). The mixture was incubated at 37° C. for 6 h and then at room temperature for 16 h before lyophilizing overnight. The residue was dissolved in water (1.6 mL) and acidified to pH ~2 by addition of 70% perchloric acid (160 μL). Insoluble material was removed by centrifugation at 18,000×g for 10 min. The supernatant was adjusted to pH 6 by addition of 10

Figure 8A:
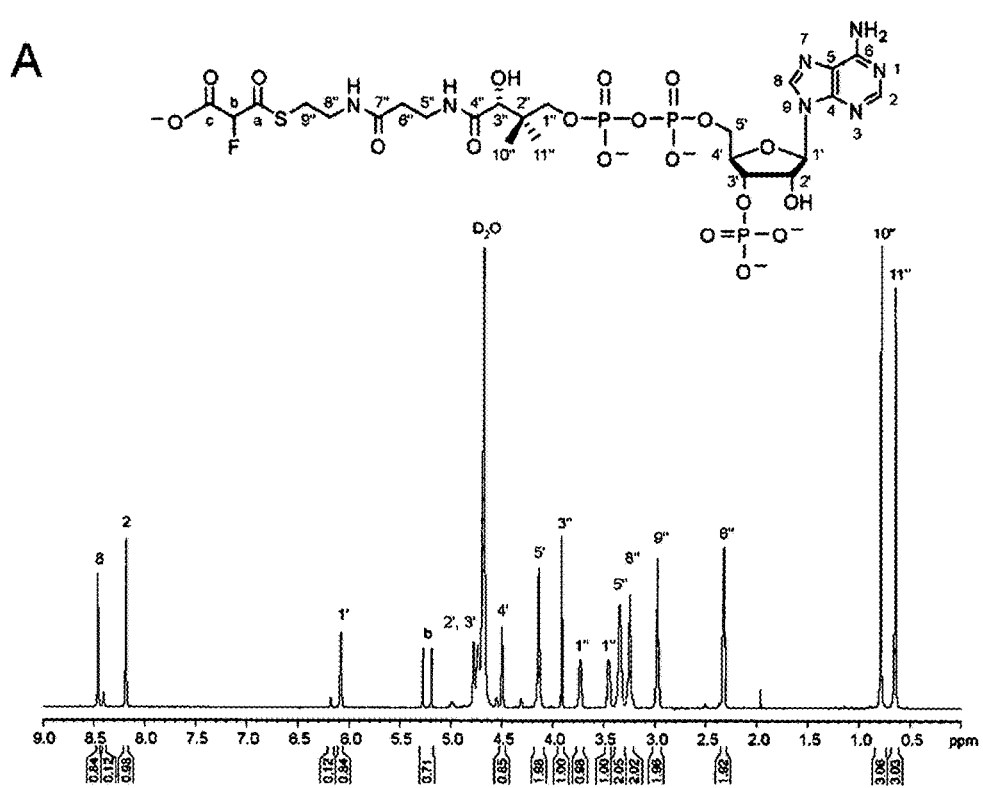
FIG. 8A-C. NMR spectra of enzymatically synthesized fluoromalonyl-CoA. (A) $^1H$ NMR. (B) $^{13}C$ NMR. (C) $^{19}F$ NMR. Spectra reflect partial ($^1H$, $^{19}F$) or complete ($^{13}C$) H-D exchange at the fluorinated position based on incubation time.
Figure 8B:
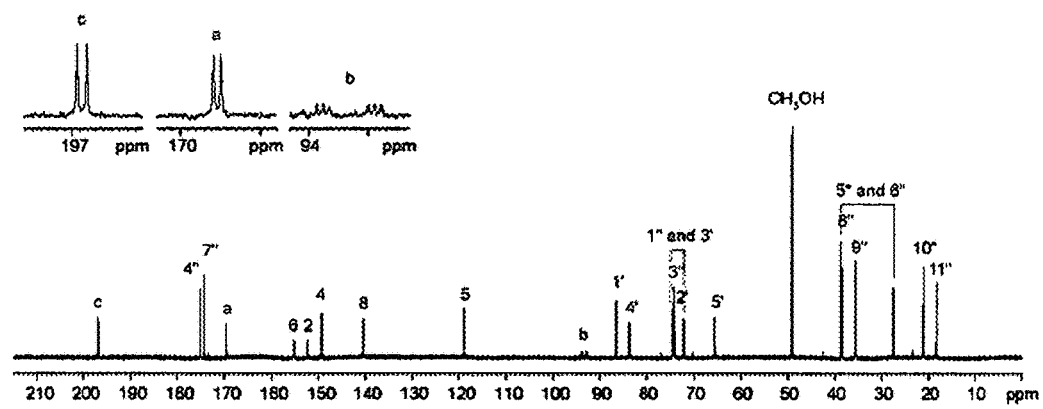
Figure 8C:
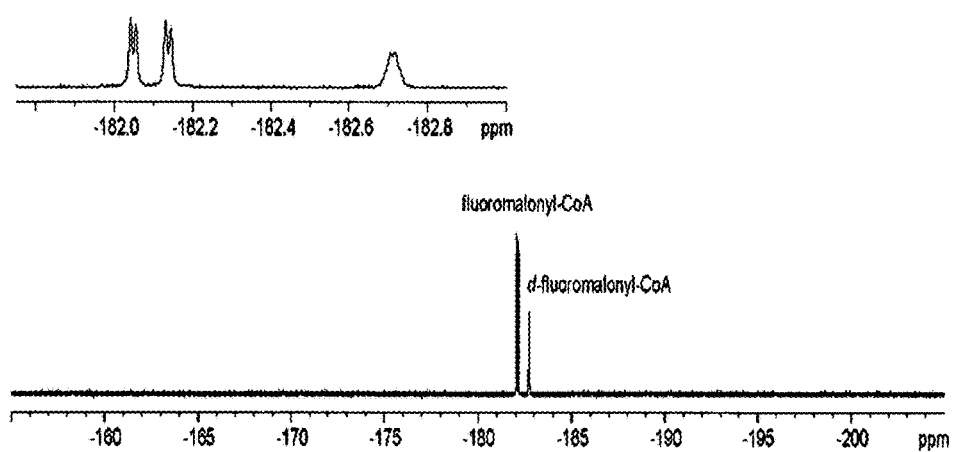

M sodium hydroxide (100 μL) and desalted on an Agilent 1200 HPLC system using a Zorbax Eclipse XDB C-18 column (5 μm, 9.4×250 mm, Agilent) with a linear gradient from 0 to 10% methanol over 9 min with 50 mM sodium phosphate, 25 mM trifluoroacetic acid, pH 4.5 as the aqueous mobile phase (3 mL/min) Fractions eluting near the void volume, containing both fluoromalonyl-CoA and CoA, were lyophilized overnight, dissolved in water (1 mL), and purified using a Zorbax Eclipse XDB C-18 column (5 μm, 9.4×250 mm) with a linear gradient from 0 to 50% methanol over 45 mM with 50 mM sodium phosphate, pH 4.5 as the aqueous mobile phase (3 mL/min) Fractions were screened by ESI-MS and those containing pure fluoromalonyl-CoA were lyophilized overnight, dissolved in water (1 mL), and desalted using a Zorbax Eclipse XDB C-18 column (5 μm, 9.4×250 mm) with a linear gradient from 0 to 15% acetonitrile over 30 min with water as the mobile phase (3 mL/min) The desalted fluoromalonyl-CoA was lyophilized and redissolved in water or $D_2O$. The fluoromalonyl-CoA solutions were stored at −20° C. but are stable for at least 24 h at room temperature. During NMR measurements in $D_2O$, complete H-D exchange occurred at the fluorine-substituted carbon over the course of 48 h. Spectra are shown in FIG. 8. $^1H$ NMR (600 MHz, $D_2O$, MeOH=3.34 ppm): δ 8.55 (s, 1H, $H_8$), 8.27 (s, 1H, $H_2$), 6.17 (d, J=6.6 Hz, 1H, $H_{1'}$), 5.23 (d, J=50.3 Hz, 1H, $O_2C$—CHF—C=O), 4.89-4.79 (m, 2H, $H_{2'}$ and $H_{3'}$), 4.59 (m, 1H, $H_{4'}$), 4.23 (m, 2H, $H_{5'}$), 4.00 (s, 1H, $H_{3''}$), 3.82 (dd, J=10.2, 4.6 Hz, 1H, pro-R— $H_{1''}$), 3.54 (dd, J=10.0, 4.4 Hz, 1H, pro-S— $H_{1''}$), 3.49-3.39 (m, 2H, $H_{5''}$), 3.38-3.29 (m, 2H, $H_{8''}$), 3.11-3.02 (m, 2H, $H_{9''}$), 2.42 (t, J=6.7 Hz, 3H, $H_{6''}$), 0.88 (s, 3H, $H_{10''}$), 0.74 (s, 3H, $H_{11'}$). $^{13}C$ NMR (226 MHz, $D_2O$, $CH_3OH$=49.15 ppm): δ 196.92, 196.85 (d, J=27.5 Hz, $\underline{C}O_2$), 175.02 ($C_{4''}$), 174.32 ($C_{7''}$), 169.52 (d, J=21.0 Hz, $O_2C$-CDF-$\underline{C}$=O), 155.37 ($C_6$), 152.40 ($C_2$), 149.57 ($C_4$), 140.37 ($C_8$), 118.91 ($C_5$), 93.32 (td, J=25 Hz, 197 Hz, $O_2C$—$\underline{C}DF$-C=O), 86.61 ($C_{1'}$), 83.81 (d, J=9 Hz, $C_{4'}$), 74.56 (d, J=5 Hz, $C_{3'}$ or $C_{1''}$), 74.35 ($C_{3''}$), 74.00 (d, J=5 Hz, $C_{2'}$), 72.16 (d, J=6 Hz, $C_{3'}$ or $C_{1''}$), 65.56 ($C_{5'}$), 38.66 ($C_{5''}$ or $C_{6''}$), 38.58 (d, J=8 Hz, $C_{8''}$) 35.58 (d, J=30 Hz, $C_{9''}$), 27.60 (d, J=3 Hz, $C_{5''}$ or $C_{6''}$), 21.16 ($C_{10''}$), 18.22 ($C_{11''}$). $^{19}F$ NMR (565 MHz, $D_2O$, $CF_3CO_2H$=−76.20 ppm): δ −182.11 (dd, J=7.8, 50.4 Hz, $O_2C$—CH$\underline{F}$—C=O), −182.72 (m, $O_2C$—CD$\underline{F}$—C=O). HR-ESI-MS [M−H]$^-$: calculated for $C_{24}H_{36}FN_2O_{19}P_3S$, m/z, 870.0989. found m/z 870.0991.

Enzyme Assays.

Kinetic parameters ($k_{cat}$, $K_M$) were determined by fitting the data using Microcal Origin to the equation: $v_o=v_{max}[S]/(K_M+[S])$, where v is the initial rate and [S] is the substrate concentration. Data are reported as mean±s.e. (n=3) unless otherwise noted with standard error derived from the nonlinear curve fitting. Error bars on graphs represent mean±s.d. (n=3). Error in $k_{cat}/K_M$ is calculated by propagation of error from the individual kinetic parameters.

Acetyl-CoA Carboxylase.

ACCase activity was measured using a discontinuous HPLC assay. Assays were performed at 30° C. in a total volume of 200 μL containing 50 mM HEPES, pH 7.5, TCEP (10 mM), bovine serum albumin (3 mg/mL), CoA (0.5 mM), ATP (2.5 mM), magnesium chloride (10 mM), sodium bicarbonate (75 mM), acetate or fluoroacetate (10 mM), phosphoenolpyruvate (10 mM), pyruvate kinase (4 U), AckA (0.1 μM), Pta (10 μM) and ACCase (15 μM). The pH of the buffer remained unchanged after addition of sodium bicarbonate. ACCase stock solution was prepared by premixing the protein subunits at equimolar ratio (85 μM) except for AccB, which was added at 1.5-fold molar excess. The reaction was initiated with addition of ATP. Aliquots (20 μL) were removed and quenched by the addition of 70% perchloric acid (1 μL). Insoluble material was removed by centrifugation and the supernatant was analyzed on an Agilent 1200 or 1290 HPLC system on a LiChroCART 250-4 Purospher RP-18e column (5 μm, 4.6×250 mm, Millipore) and monitored at $A_{260\ nm}$. For reactions with acetate, a linear gradient from 2 to 20% acetonitrile over 10 min with 5 mM sodium phosphate and 5 mM sodium citrate with 0.1% trifluoroacetic acid, pH 4.6 as the aqueous mobile phase (1 mL/min) was used to analyze the reaction. For reactions with fluoroacetate, a linear gradient from 2 to 15% acetonitrile containing 0.1% TEA over 15 min with 10 mM Tris, pH 8.0 containing 0.1% TEA as the aqueous mobile phase (1 mL/min) was used. Buffers containing TEA were made fresh daily and could be used for at least 6 h before significant change in chromatography was observed.

Malonyl-CoA Synthetase.

MatB activity was measured using a modified literature method (Williamson, J. R., et al., *Method. Enzymol.*, 434-513 (1969)). The production of AMP was coupled to pyruvate formation by myokinase and pyruvate kinase, which in turn was coupled to NADH oxidation by lactate dehydrogenase. Assays were performed at 30° C. in a total volume of 200 μL containing 100 mM HEPES, pH 7.5, TCEP (1 mM), ATP (2.5 mM), magnesium chloride (5 mM), phosphoenolpyruvate (1 mM), NADH (0.3 mM), myokinase (0.5 U), pyruvate kinase (3.6 U), lactate dehydrogenase (2.6 U), dicarboxylic acid (25 μM-1 mM malonate, 50 μM-10 mM fluoromalonate or 25 μM-1.5 mM methylmalonate) and MatB (26 nM for malonate, 1 μM for fluoromalonate and 200 nM for methylmalonate). The reaction was initiated with addition of CoA (0.5 mM) and monitored at 340 nm in a Beckman Coulter DU-800 spectrophotometer.

Acetoacetyl-CoA Synthase.

NphT7 activity was measured using a NADPH-coupled assay with PhaB. Assays were performed at 30° C. in a total volume of 500 μL containing 50 mM HEPES, pH 7.5, NADPH (160 μM), acetyl-CoA (200 μM), PhaB (0.05 mg/mL), NphT7 (0.2 μM for malonyl-CoA; 0.5 μM for fluoromalonyl-CoA) and malonyl-CoA (5-150 μM) or fluoromalonyl-CoA (5-200 μM). Reactions were initiated with the addition of malonyl- or fluoromalonyl-CoA and monitored at 340 nm in an Agilent 8453 diode array spectrophotometer. The PhaB-coupled assay was tested both by doubling NphT7, which doubled the initial velocity with both the fluorinated and non-fluorinated substrates, and also by doubling the amount of PhaB, which led to no difference in initial velocity.

Acyl-CoA Hydrolysis by DEBS.

Hydrolytic activity of $DEBS_{Mod6}$+TE was measured by monitoring the reaction of free CoA with DTNB as described previously (Huang, F., et al., *Chem. Biol.*, 13:475-484 (2006)). Assays were performed at 37° C. in a total volume of 200 μL containing 400 mM sodium phosphate, pH 7.5, 500 μM DTNB, and $DEBS_{Mod6}$+TE (1 μM). Reactions were initiated by addition of acyl-CoA (0.5 mM) and monitored at 412 nm in a Beckman Coulter DU-800 spectrophotometer. Release of CoA was quantified by comparison to a standard curve (5-100 μM).

Tetrahydroxynaphthalene Synthase.

THNS activity was measured by monitoring THN production spectrophotometrically at 340 nm as previously described (Izumikawa, M., et al., *J. Ind. Microbiol. Biot.*, 30:510-515 (2003)). The specific activity was comparable to the reported value.

Tetrahydroxynaphthalene Production Using THNS

All reactions (160 µL) contained 100 mM HEPES, pH 7.5, magnesium chloride (10 mM), BSA (300 µg/mL), sodium bicarbonate (75 mM), phosphoenolpyruvate (10 mM) and pyruvate kinase (2.9 U). The following final concentrations of substrates and enzymes were added to the appropriate reactions: AckA (10 nM), Pta (10 µM), ACCase (5 µM), MatB (5 µM), myokinase (1.6 U), sodium malonate (5 mM), malonyl-CoA (0.5 mM), acetyl-CoA (0.5 mM), and ATP (2.5 mM). ACCase was incubated at 30° C. for 10 min with the reaction mixture before initiation with THNS (2.5 µM). When AckA/Pta activation of acetate was included, reaction mixtures were pre-incubated at 30° C. for 6 min before addition of ACCase. Reactions containing TCEP (2.5 mM) were also tested, but no apparent effect on THN production was observed. All reactions were incubated at 30° C. for 24 h and flash-frozen in liquid nitrogen. Samples were thawed individually on ice before quantifying total polyketide production using a Beckman DU-800 spectrophotometer. $A_{510\ nm}$ was taken as a measure of tetrahydroxynaphthalene, flaviolin, and their spontaneous polymerization products (Funa, N., et al., *Nature*, 400:897-899 (1999)).

2-fluoro-3-hydroxybutyryl-CoA Production Using NphT7

As acetofluoroacetyl-CoA proved to degrade fairly rapidly under the assay conditions, 2-fluoro-3-hydroxybutyryl-CoA was isolated from a 10 mL reaction containing 100 mM HEPES, pH 7.5, fluoromalonate (10 mM), CoA (500 µM), NADPH (1 mM), ATP (1 mM), magnesium chloride (5 mM), phosphoenolpyruvate (10 mM), pyruvate kinase (180 U), myokinase (100 U), MatB (40 µM), PhaB (7 µM) and NphT7 (2 µM) that was initiated by the addition of acetyl-CoA (0.5 mM, limiting reagent). The reaction was incubated at 30° C. overnight followed by quenching by the addition of 70% perchloric acid (50 µL). 2-fluoro-3-hydroxybutryl-CoA was purified using a Zorbax Eclipse XDB C-8 column (5 µm, 9.4×250 mm, Agilent) with a linear gradient from 0 to 5% acetonitrile over 30 min (3 mL/min) with 50 mM sodium phosphate with 0.1% trifluoroacetic acid (pH 4.5) as the aqueous mobile phase. Fractions containing 2-fluoro-3-hydroxybutryl-CoA were identified by ESI-MS and lyophilized. The remaining solid was dissolved in water (1 mL) and purified a second time a Zorbax Eclipse XDB C-8 column (5 µm, 9.4×250 mm, Agilent) with a linear gradient from 0 to 5% acetonitrile over 30 min (3 mL/min) with 0.1% formic acid as the aqueous mobile phase. Fractions containing 2-fluoro-3-hydroxybutryl-CoA were identified by ESI-MS and lyophilized. Two diastereomers were observed by NMR in an approximately 2.5:1 ratio. $^1$H NMR (600 MHz, D$_2$O, acetonitrile=2.06 ppm): δ 8.54 (s, 1H, H$_8$), 8.30 (s, 1H, H$_2$), 6.08 (d, J=5.9 Hz, 1H, H$_1$), 4.93 (dd, J=47.8, 2.6 Hz, 0.2H, HOCH—CHF—C═O minor diastereomer), 4.85 (dd, J=46.9, 2.2 Hz, 0.8H, HOCH—CHF—C═O major diastereomer), 4.77-4.77 (m, 2H, H$_{2'}$ and H$_{3'}$), 4.46 (m, 1H, H$_{4'}$), 4.16-4.04 (m, 3H, HOC<u>H</u>—CHF—C═O, H$_{5'}$), 3.89 (s, 1H, H$_{3''}$), 3.72 (d, J=7.1 Hz, 1H, H$_{1''}$ pro-R), 3.46 (d, J=9.7 Hz, 1H, pro-S—H$_{1''}$ pro-S), 3.31 (t, J=6.5 Hz, 2H, H$_{5''}$), 3.26-3.20 (m, 2H, H$_{8''}$), 2.95 (m, 2H, H$_{9''}$), 2.30 (t, J=6.5 Hz, 2H, H$_{6''}$), 1.15 (d, J=6.7 Hz, 2H, <u>H</u>$_3$C—HOCH—CHF major diastereomer), 1.05 (d, J=6.4 Hz, 1H, <u>H</u>$_3$C—HOCH—CHF minor diastereomer), 0.79 (s, 3H, H$_{10''}$), 0.67 (s, 3H, H$_{11''}$). $^{19}$F NMR (565 MHz, D$_2$O, CF$_3$CO$_2$H=−76.20 ppm): δ −198.62 (dd, J=48.24, 23.3 Hz, HOCH—CH<u>F</u>—C═O), −206.85 (dd, J=46.9, 27.5, HOCH—CH<u>F</u>—C═O). ESI-MS [M+H]$^+$: calculated for C$_{25}$H$_{42}$FN$_7$O$_{18}$P$_3$S, m/z, 872.2. found m/z 872.0.

Triketide Lactone Production Using DEBS$_{Mod6}$+TE and MatB

Assay and preparative mixtures contained 400 mM sodium phosphate, pH 7.5, phosphoenolpyruvate (50 mM), TCEP (5 mM), magnesium chloride (10 mM), ATP (2.5 mM), pyruvate kinase (27 U/mL), myokinase (10 U/mL), CoA (0.5 mM), methylmalonyl-CoA epimerase (5 µM), MatB (40 µM or as specified) and fluoro- or methylmalonate (10-20 mM). Including NADPH resulted in only trace yields of reduced triketide product, even with the native methylmalonyl-CoA extender, so the cofactor was omitted. This mixture was incubated at 37° C. for 30-45 min and then initiated by addition of the N-acetylcysteamine thioester of (2S,3R)-2-methyl-3-hydroxypentanoic acid (NDK-SNAC, 1-10 mM) (Cane, D. E., et al., *J. Am. Chem.*, 115:527-535 (1993)) and DEBS$_{Mod6}$+TE (10 µM). Aliquots (35 µL) were removed and quenched by addition of 70% perchloric acid (1.75 µL). Samples were centrifuged at 18,000×g to pellet the precipitated protein. The supernatant (33 µL) was removed and added to 1 M sodium bicarbonate (6.6 µL) bringing the final pH to 4-5. Excess salts were precipitated by freezing in liquid nitrogen and centrifuging at 18,000×g until thawed. The supernatant was removed and analyzed on a Zorbax Eclipse XDB C-18 column (3.5 µm, 3×150 mm, 35° C., Agilent) using a linear gradient from 0 to 40% acetonitrile over 14 min with 0.1% formic acid as the aqueous mobile phase after an initial hold at 0% acetonitrile for 30 s (0.8 mL/min) Products were monitored using an Agilent G1315D diode array detector (TKL, $A_{260\ nm}$ or $A_{275\ nm}$, F-TKL, $A_{247\ nm}$, NDK-SNAC; $A_{260\ nm}$). The identity of each compound was verified using an Agilent 6130 single quadruple mass spectrometer in negative ion mode. For absolute quantification, each analyte was compared to an external standard curve. The concentration of the 2-fluoro-2-desmethyltriketide lactone (F-TKL) synthetic standard was determined by $^{19}$F NMR using the ERETIC method (Akoka, S., et al., *Anal. Chem.*, 71:2554-2557 (1999)) against an external standard of 5.00 mM 5-fluorouracil. The triketide lactone (TKL) standard was prepared enzymatically, and the 2-desmethyltriketide lactone (H-TKL) standard was synthesized as described (Hinterding, K., et al., *Tetrahedron lett.*, 42:8463-8465 (2001)). The concentrations of TKL and H-TKL were determined by $^1$H NMR in D$_2$O using the ERETIC method against an external standard of diethylfluoromalonate (75 mM).

Enzymatic Preparation of Methyl- and Fluorotriketide Lactones from Methylmalonate and Fluoromalonate.

Reaction mixtures (TKL, 4 mL; F-TKL, 8 mL) containing NDK-SNAC (10 mM) were prepared as described above and incubated for 18 h. Protein was removed by the addition of 70% perchloric acid (0.05 volumes) and centrifuged at 18,000×g for 10 min. The supernatant was removed and extracted extensively with dichloromethane (TKL, 5×15 mL; F-TKL, 5×30 mL) and the organic layers concentrated to 5-10 mL by rotary evaporation. The residue was transferred to a silanized glass vial (Sigmacote®, Sigma-Aldrich) and 50 mM sodium bicarbonate was added (1 mL). The dichloromethane was removed from the biphasic mixture by rotary evaporation to transfer the triketide into the aqueous phase. The aqueous solution of triketide was purified on a Zorbax Eclipse XDB C-18 column (5 µm, 9.4×250 mm, Agilent) using a linear gradient from 0 to 27.5% methanol with 50 mM sodium phosphate, pH 4.5 over 45 min as the aqueous mobile phase (3 mL/min) Fractions containing triketide were pooled and extracted with dichloromethane (4×3 volumes), and the combined organic layers were dried over magnesium sulfate and concentrated.

The TKL was purified further on a Zorbax Eclipse XDB C-18 (5 μm, 9.4×250 mm, Agilent) using a linear gradient from to 0 to 30% acetonitrile with 0.1% formic acid as the aqueous mobile phase over 45 min (3 mL/min) after transferring back into bicarbonate buffer as described above. Fractions containing TKL were combined and lyophilized for analysis. Due to the presence of a α-keto moiety, TKL was expected to be produced as a diastereomeric mixture, and was in fact isolated as a 100:7 mixture of (2R,4S,5R)-2,4-Dimethyl-3-oxo-5-hydroxy-n-heptanoic acid β-lactone and its 2S-epimer. The observed NMR spectra are in agreement with the literature (Luo, G., et al., *Bioorg. Med. Chem.*, 4:995-999 (1996)). $^1$H NMR (500 MHz, CDCl$_3$): δ 4.66 (ddd, J=8.4, 5.4, 2.9 Hz, 2R H$_5$), 4.48-4.42 (m, 2S H$_5$), 3.62 (q, J=6.6 Hz, 2R H$_2$), 3.25 (d, J=7.5 Hz, 2S H$_2$), 2.83 (dd, J=7.2, 4.7 Hz, 2S H$_4$), 2.63 (qd, J=7.6, 2.9 Hz, 2R H$_4$), 1.93-1.82 (m, 2R H$_{6a}$), 1.65 (dqd, J=14.8, 7.6, 5.4 Hz, 2R H$_{6b}$), 1.48 (d, J=7.5 Hz, 2S C$_2$—CH$_3$), 1.37 (d, J=6.7 Hz, 2R C$_2$—CH$_3$), 1.16 (d, J=6.4 Hz, 2S C$_4$—CH$_3$), 1.12 (d, J=7.5 Hz, 2R C$_4$—CH$_3$), 1.08 (t, J=7.5 Hz, 2R H$_7$), 1.01 (t, J=7.5 Hz, 2S H$_7$). $^{13}$C NMR (226 MHz, CDCl$_3$, only the 2R epimer was detected): δ 205.59 (C$_3$), 170.21 (C$_1$), 78.68 (C$_5$), 50.56 (C$_2$), 44.52 (C$_4$), 24.19 (C$_6$), 10.09 (C$_7$), 9.90 (C$_4$—CH$_3$), 8.40 (C$_2$—CH$_3$). HR-ESI-MS [M−H]$^−$: calculated for C$_9$H$_{13}$O$_3$, m/z 169.0870. found m/z 169.0871.

Figure 17A:
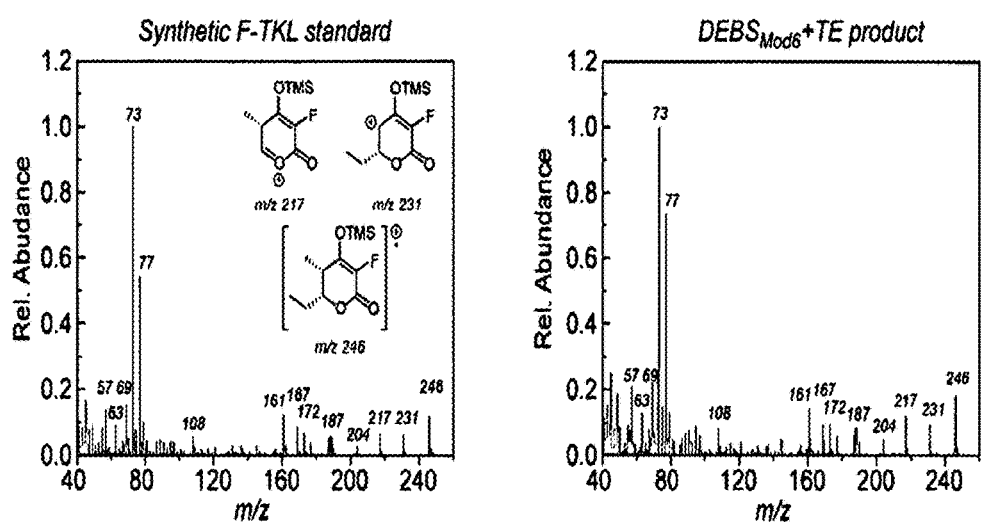
FIG. 17A-B. GC-MS and $^{19}$F NMR comparison of enzymatic F-TKL to the authentic F-TKL synthetic standard. (A) Comparison of EI mass spectra of the standard (t$_R$=8.51 min) compared to the enzymatic product (t$_R$=8.56 min) (B) Comparison of $^{19}$F NMR spectra in CDCl$_3$. The keto form is dominant at this concentration.
Figure 17B:
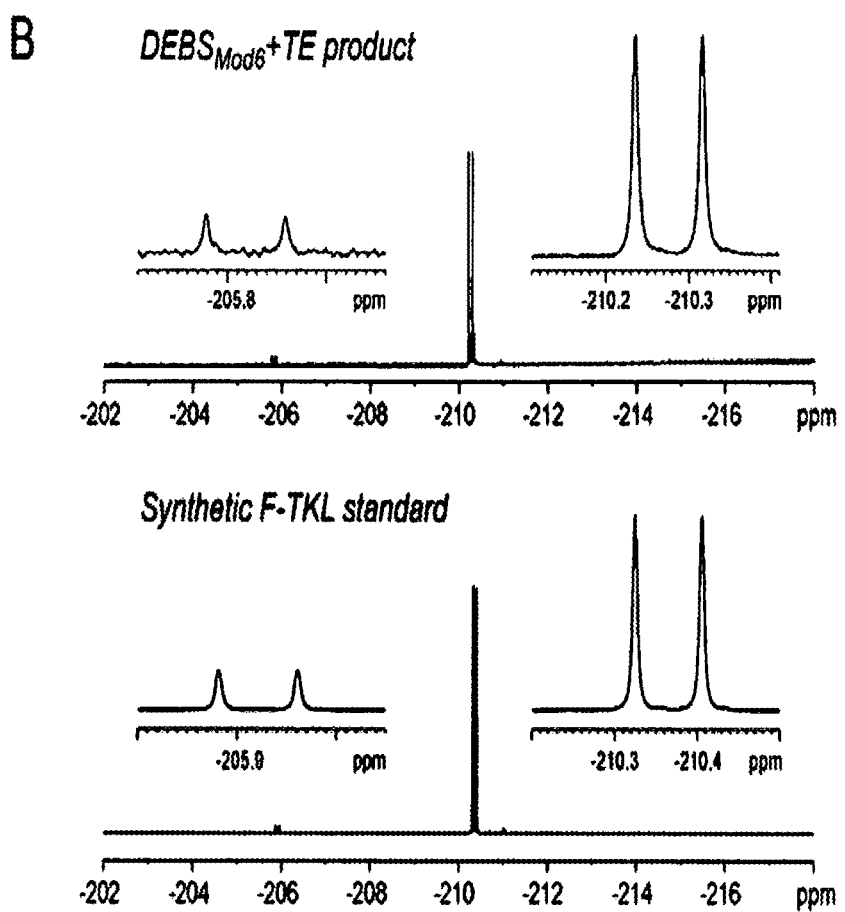

The enzymatic F-TKL was compared against an authentic synthetic standard by LC-MS, HR-ESI-MS, $^{19}$F-NMR, and GC-MS (FIG. 4, FIG. 17). $^{19}$F-NMR (565 MHz, CDCl$_3$, CFCl$_3$=0 ppm): −171.95 (broad singlet), −210.32 (d, J=45.8 Hz). GC-MS: t$_R$, 8.56 min; EI spectrum (FIG. 17). HR-ESI-MS [M−H]$^−$: calculated for C$_8$H$_{10}$FO$_3$, m/z 173.0619. found m/z 173.0623.

Enzymatic Preparation of F-TKL from Fluoroacetate

One-pot reaction mixtures containing 200 mM HEPES, pH 7.5, TCEP (2 mM), bovine serum albumin (3 mg/mL), magnesium chloride (5 mM), fluoroacetate (10 mM), NDK-SNAC (10 mM), coenzyme A (2 mM), sodium bicarbonate (75 mM), ATP (2.5 mM), phosphoenolpyruvate (50 mM), pyruvate kinase (18 U/mL), myokinase (10 U/mL), AckA (10 μM), Pta (1 μM), ACCase (15 μM), MatB (40 μM), methylmalonyl-CoA epimerase (5 μM) and DEBS$_{Mod6}$+TE (10 μM) in a total volume of 1000 μL were incubated at 37° C. for 1.5 hrs at which time sodium phosphate pH 7.5 (400 mM) was added to the reaction. The reaction was incubated at 37° C. for a further 24 hrs. An aliquot (200 μL) was removed and prior to analysis, the aliquot was quenched by the addition of 70% perchloric acid (10 μL). F-TKL production was analyzed by LC-MS as described above using single ion monitoring at m/z 173 in negative ion mode. Telescope reaction mixtures containing 200 mM HEPES, pH 7.5, TCEP (2 mM), bovine serum albumin (3 mg/mL), magnesium chloride (5 mM), fluoroacetate (10 mM), coenzyme A (1 mM), sodium bicarbonate (75 mM), ATP (2.5 mM), phosphoenolpyruvate (50 mM), pyruvate kinase (18 U/mL), AckA (10 μM), Pta (1 μM) and ACCase (15 μM) in a total volume of 1000 μL were incubated at 37° C. for 1.5 hrs. The reaction was then spun through an Amicon spin concentrator (MWCO 3 kD) to remove proteins. 792 μL of the flow through was used to prepare a reaction with 400 mM sodium phosphate, pH 7.5, TCEP (2 mM), magnesium chloride (10 mM), NDK-SNAC (10 mM), phosphoenolpyruvate (50 mM), pyruvate kinase (18U/mL), myokinase (10 U/mL), MatB (40 μM), methylmalonyl-CoA epimerase (5 μM) and DEBS$_{Mod6}$+TE (10 μM) in a total volume of 1000 μL. The reactions were allowed to proceed for 24 h and were assayed as described for the one-pot reactions.

(2S,3R)-1-((S)-4-Benzyl-2-oxooxazolidin-3-yl)-2-methyl-1-oxopentan-3-yl2-fluoroacetate (1)

(S)-4-benzyl-3-((2S,3R)-3-hydroxy-2-methylpentanoyl)oxazolidin-2-one (171 mg, 0.585 mmol) was prepared as previously described (Cane, D. E., et al., *J. Am. Chem.*, 115:527-535 (1993)) and combined with sodium fluoroacetate (70 mg, 0.703 mmol, 1.2 eq) and HATU (267 mg, 0.702 mmol, 1.2 eq) in a flame-dried round-bottom flask under a nitrogen atmosphere. Anhydrous THF (5.9 mL) and diisopropylethylamine (306 μL, 1.76 mmol, 3 eq) were added and the reaction was capped and stirred vigorously at room temperature for 44 h, during which time the white suspension turned orange-brown. The mixture was diluted with ethyl acetate and washed with saturated sodium bicarbonate, resulting in two clear layers. The orange-brown organic layer was washed again with saturated sodium bicarbonate, dried over MgSO$_4$, filtered through a plug of silica, and concentrated to give an orange-brown oil. The residue was purified by flash chromatography on silica (30 g) using a step gradient from 100% heptane to 25% ethyl acetate in heptane with the desired compound beginning to elute in 20% ethyl acetate. Fractions were concentrated to yield the product (173 mg, 84%) as a clear, colorless oil, R$_f$ 0.35 (25% ethyl acetate/hexanes). $^1$H NMR (500 MHz, CDCl$_3$): δ 7.39-7.16 (m, Ph-H), 5.31 (ddd, J=7.9, 5.9, 3.2 Hz, H$_3$), 4.87 (d, J=47.0, CH$_2$F—C=O), 4.60 (dddd, J=9.8, 7.7, 3.5, 2.3 Hz, H$_4$), 4.31 (ddd, J=8.7, 7.7, 0.8 Hz, H$_5$ pro-R), 4.19 (dd, J=8.9, 2.3 Hz, H$_5$ pro-S), 4.09 (qd, J=6.9, 3.2 Hz, H$_{2'}$), 3.28 (dd, J=13.4, 3.5 Hz, H$_{6a}$), 2.78 (dd, J=13.4, 9.8 Hz, H$_{6b}$), 1.79-1.64 (m, H$_{4'}$), 1.22 (d, J=6.9 Hz, C$_2$—CH$_3$), 0.95 (t, J=7.4 Hz, H$_5$). $^{13}$C NMR (151 MHz, CDCl$_3$): δ 173.95 (C$_{1'}$), 168.04 (d, J=22.0 Hz, CH$_2$F—C=O), 153.83 (N—C=O—O), 135.41 (C$_{aryl}$), 129.56 (C$_{aryl}$), 129.07 (C$_{aryl}$), 127.48 (C$_{aryl}$), 77.44 (d, J=182.3 Hz, CH$_2$F—C=O), 76.40 (C$_{3'}$), 66.58 (C$_5$), 55.94 (C$_4$), 41.00 (C$_{2'}$), 38.05 (C$_6$), 25.16 (C$_{4'}$), 10.15 (C$_2$—CH$_3$), 10.04 (C$_{5'}$). $^{19}$F NMR (565 MHz, CDCl$_3$, CFCl$_3$=0 ppm): δ −230.44 (t, J=47.0 Hz). HR-ESI-MS [M+Na]$^+$: calculated for C$_{18}$H$_{22}$FNO$_5$Na, m/z 374.1374. found m/z 374.1381.

Preparation of (2S,4S,5R)-2-fluoro-4-methyl-3-oxo-5-hydroxy-n-heptanoic Acid δ-lactone (F-TKL)

Figure 14A:
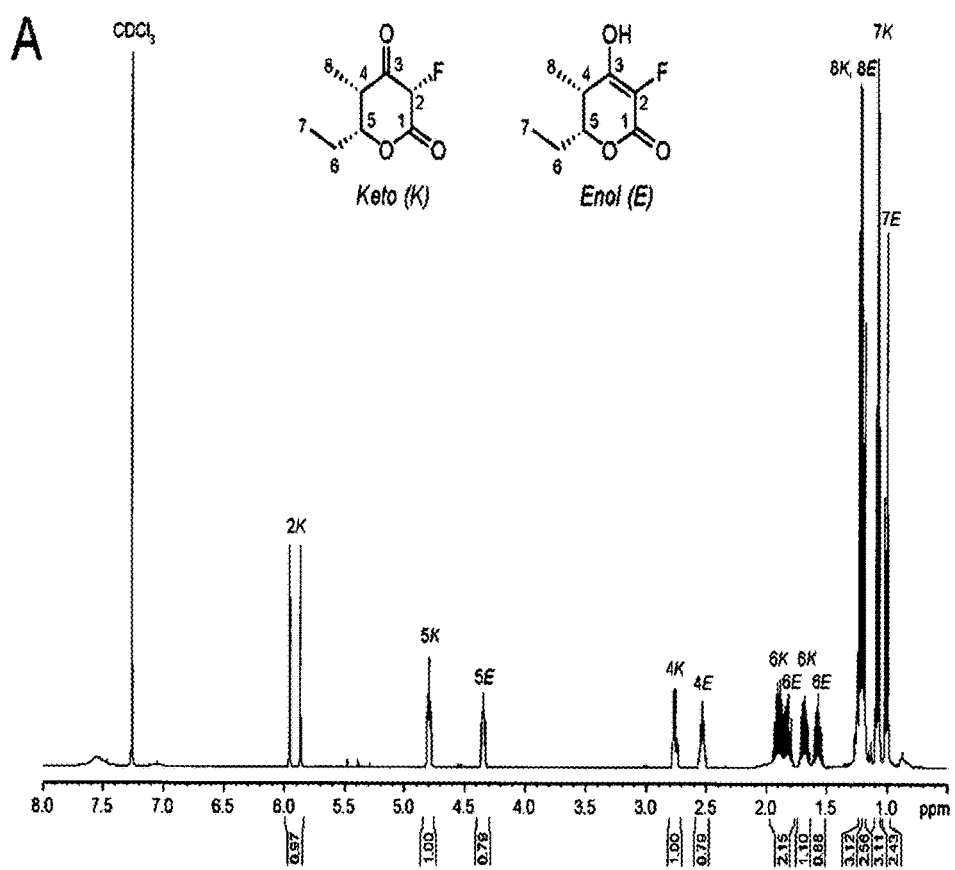
FIG. 14A-C. 1D-NMR spectra of synthetic F-TKL standard in CDCl$_3$. (A) $^1$H NMR. (B) $^{13}$C NMR. (C) $^{19}$F NMR. The relative keto:enol ratio in CDCl$_3$ depends on concentration and increases with decreasing concentration.
Figure 14B:
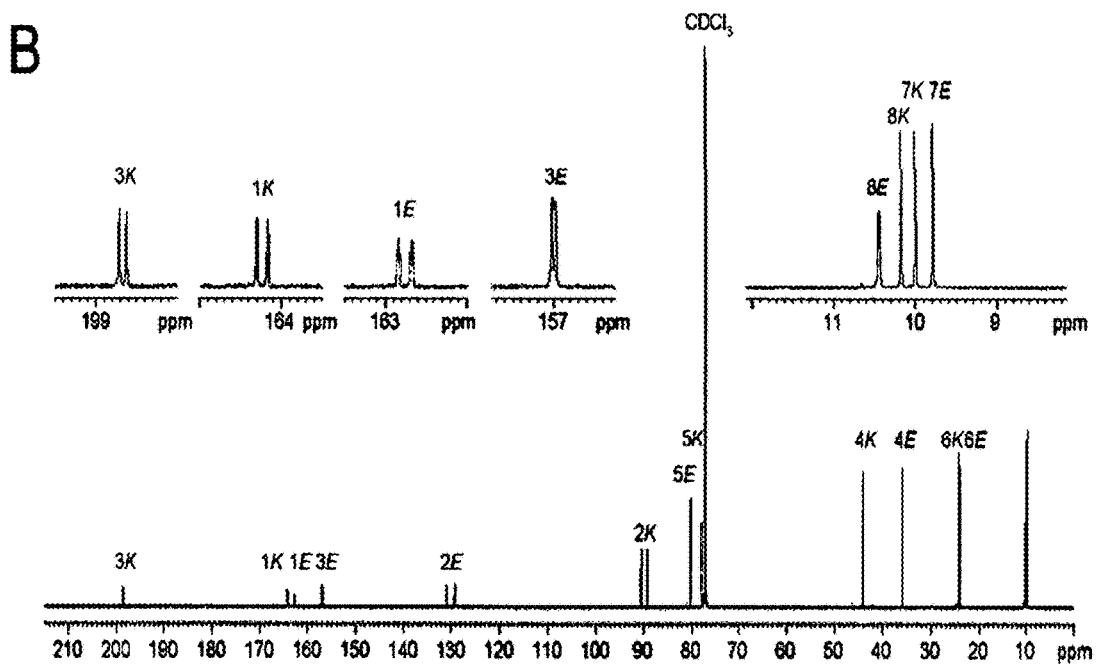
Figure 14C:
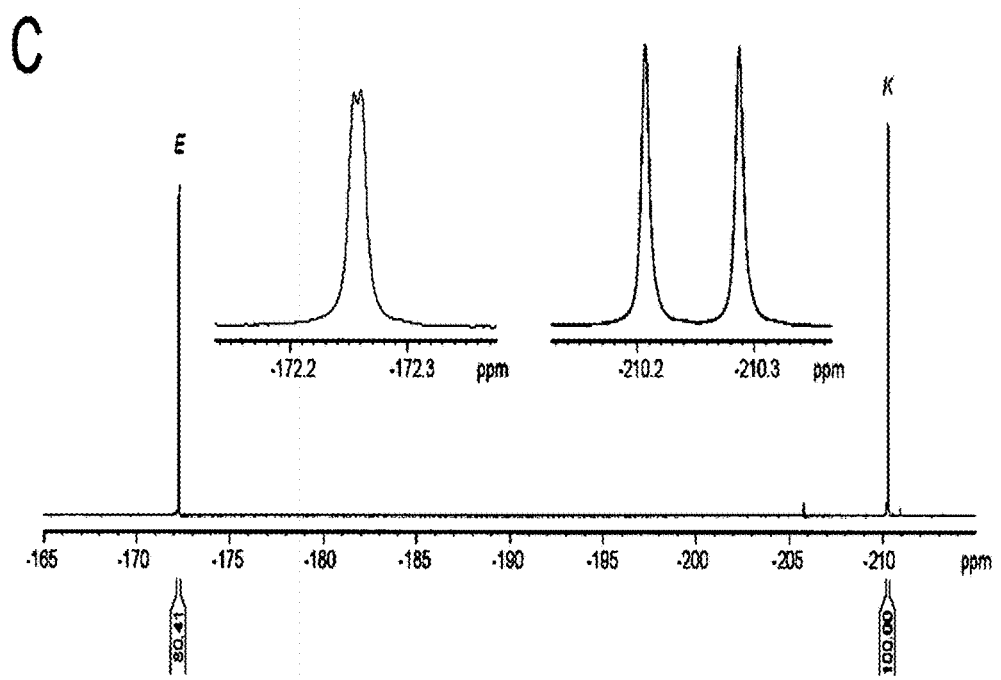
Figure 15A:
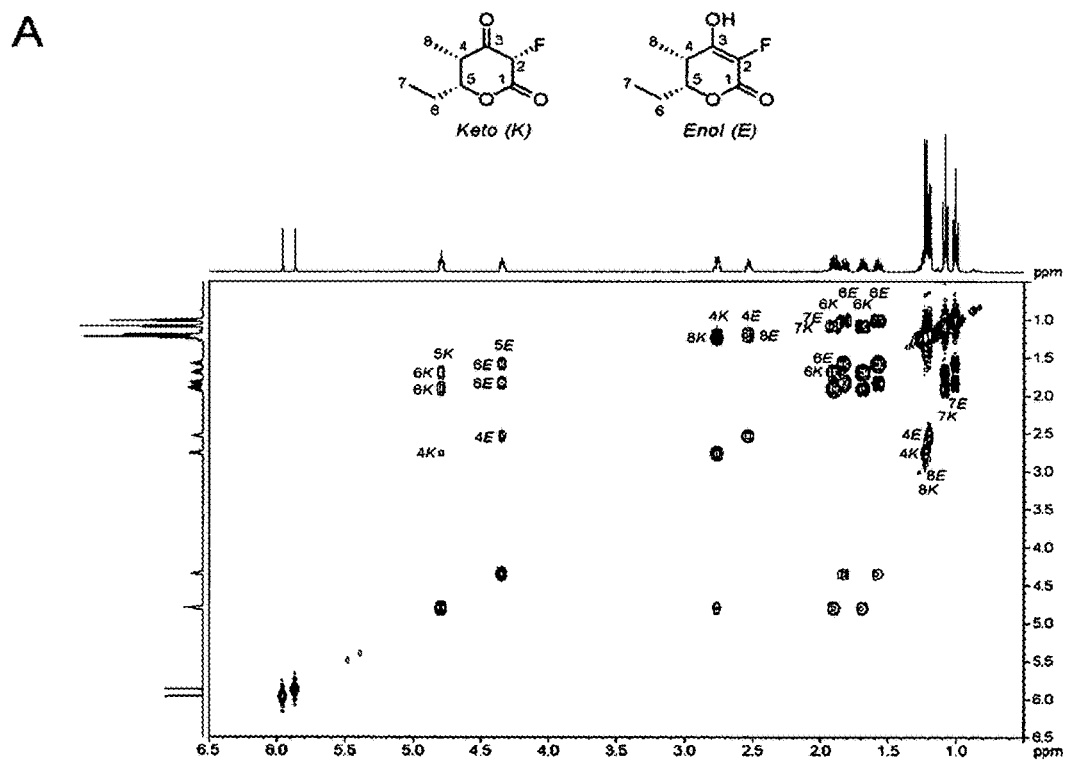
FIG. 15A-D. 2D-NMR spectra of synthetic F-TKL standard in CDCl$_3$. (A) COSY. (B) $^1$H-$^{13}$C HSQC. (C) $^1$H-$^{13}$C HMBC. (D) $^1$H-$^{19}$F HMBC (see also FIG. 16C).
Figure 15B:
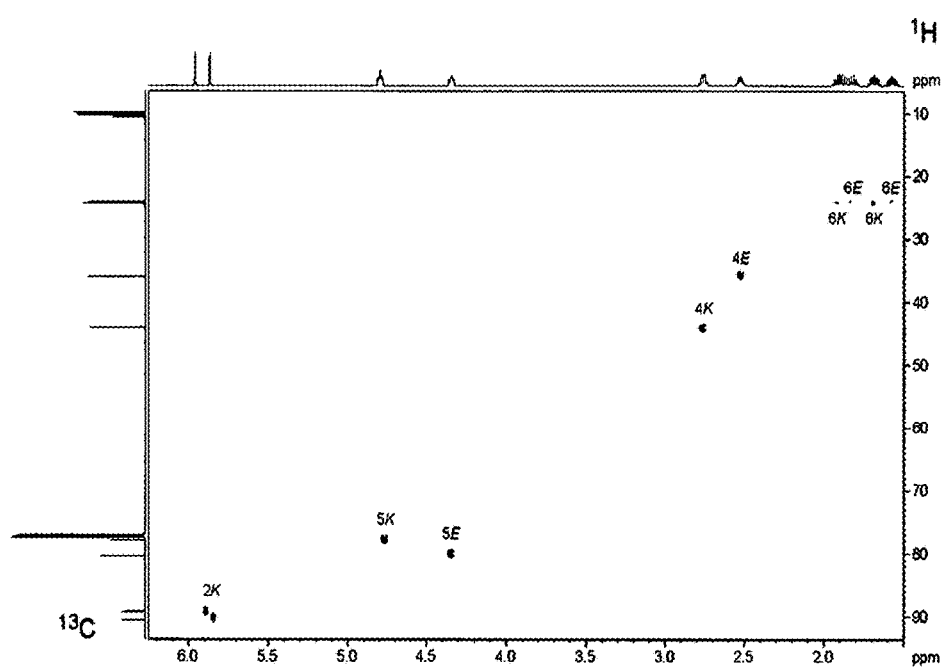
Figure 15C:
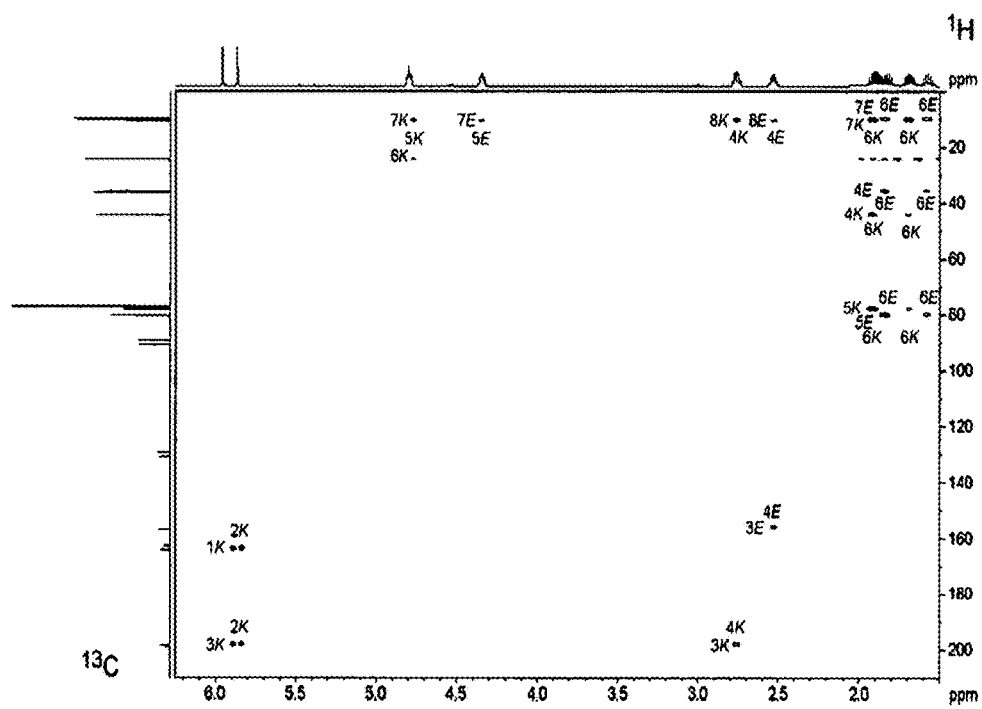
Figure 15D:
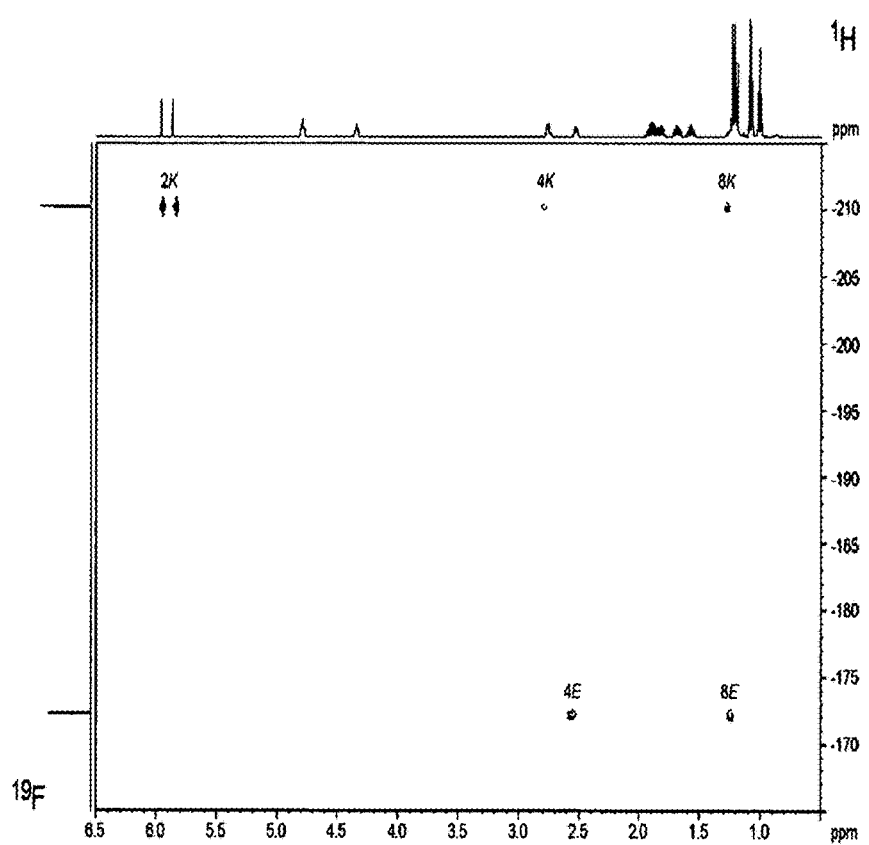
Figure 16A:
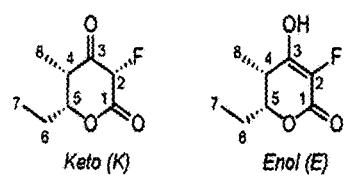
FIG. 16A-C. Stereochemical analysis for F-TKL. (A) $^1$H NOESY spectrum of synthetic F-TKL standard in CDCl$_3$. The same ratio between epimers is observed for enzymatically produced F-TKL. (B) Molecular modeling results for F-TKL. The lowest energy conformations of the two F-TKL keto diastereomers were selected based on a conformational search (Macromodel) using Maestro 9.3 (Schrödinger, Inc). Only the 2S epimer would be expected to show a single NOE coupling between H$_2$ and H$_5$, as observed. (C) $^1$H-$^{19}$F HMBC of keto isomer region of synthetic F-TKL standard in CDCl$_3$, showing crosspeaks for the major and minor epimers.
Figure 16A:
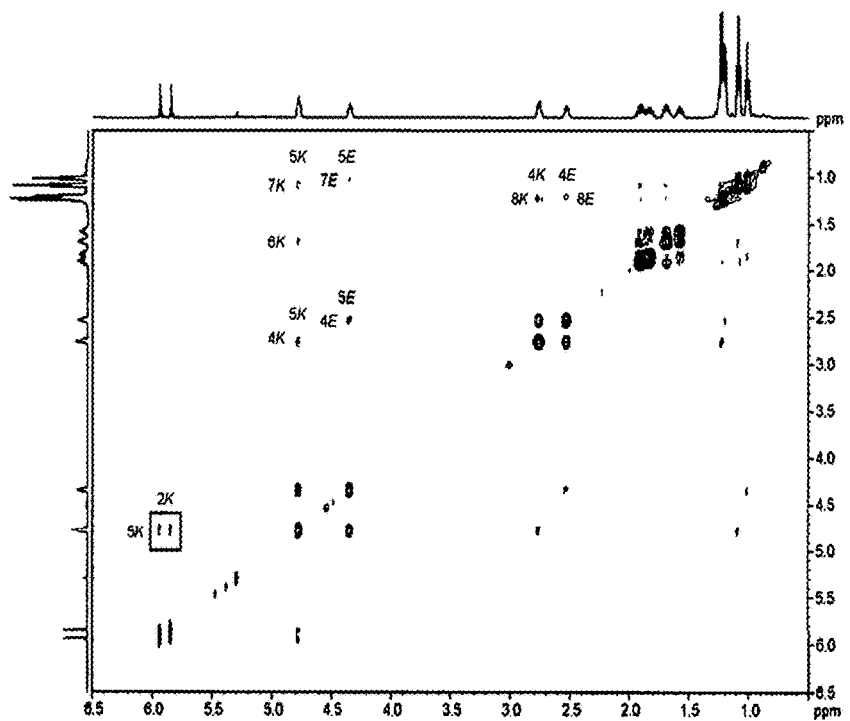
Figure 16B:
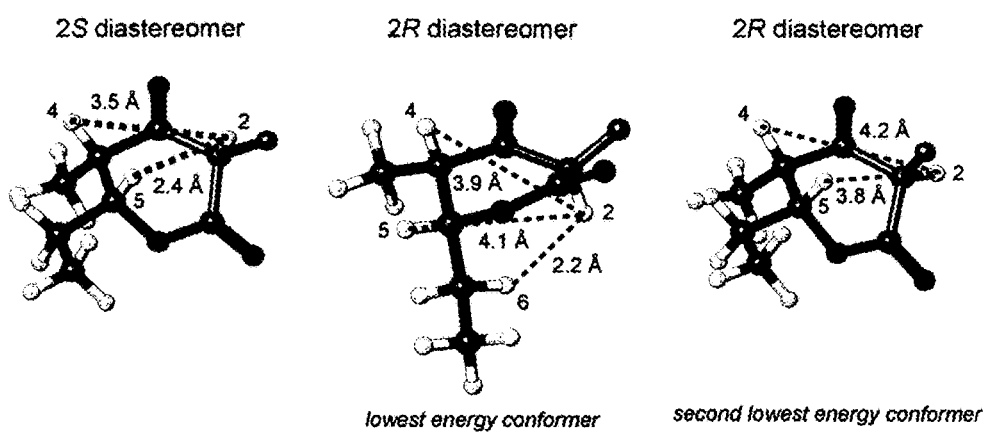
Figure 16C:
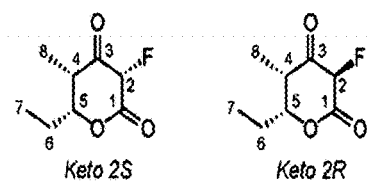
Figure 16C:
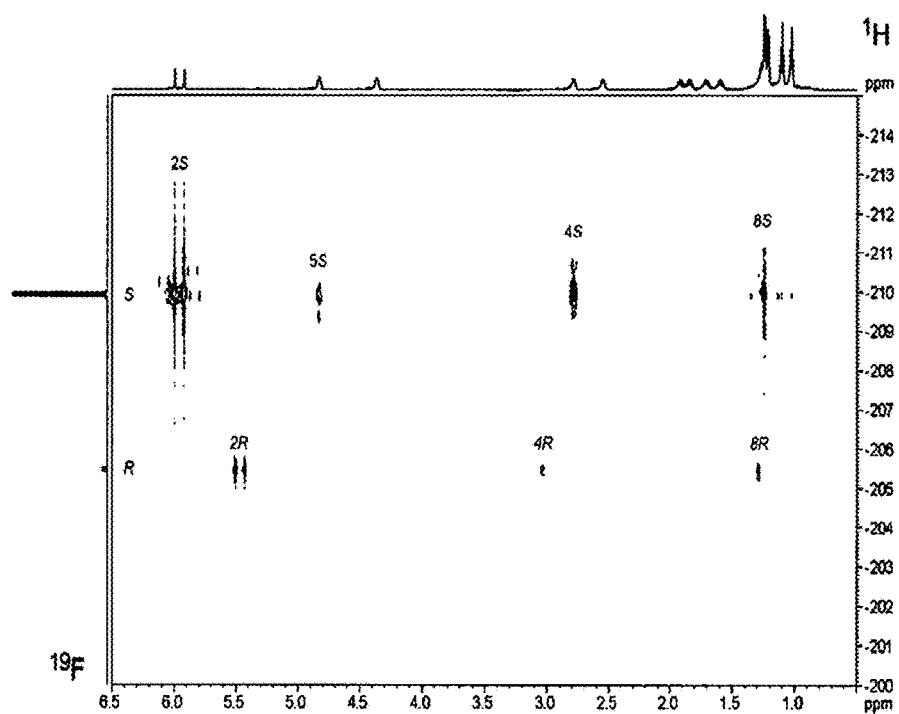

Lactonization of 1 was carried out using literature methods (Hinterding, K., et al., *Tetrahedron lett.*, 42:8463-8465 (2001)). 1 (160 mg, 0.455 mmol) was dried under vacuum in a pear-shaped flask then placed under nitrogen. In a flame-dried round-bottom flask, anhydrous THF (4.5 mL) and LiHMDS (1.0 M in THF, 1.366 mL, 3 eq) were combined, stirred and cooled to −78° C. under nitrogen. The starting material was dissolved in anhydrous THF (3.5 mL), cooled to −78° C., and cannulated dropwise into the solution of base over 20 min. A rinse of anhydrous THF (1.5 mL) was also transferred by cannula. The reaction mixture was stirred for 3 h at −78° C. and quenched by addition of saturated ammonium chloride/methanol/water (1:1:1 v/v/v, 13 mL). The mixture was then allowed to warm to room temperature while stirring. The pH of the quenched mixture was adjusted to 9 using 10 M NaOH and extracted with 3×40 mL ethyl acetate to remove the oxazolidinone auxiliary. The aqueous layer was adjusted to pH 2 using 12 M HCl and then extracted with 5×20 mL dichloromethane. The combined organic layers were concentrated to give a clear, colorless oil, which contained approximately 1 mol % starting material by $^1$H NMR (36 mg, 45%). The product was further purified by flash chromatography on silica by washing extensively with dichloromethane ($R_f$<0.05) then eluting with ethyl acetate ($R_f$~0.4), and concentrated to yield a white, crystalline solid (13 mg, 16%). A mixture of enol (53%) and keto (47%) tautomers was observed in CDCl$_3$ (FIGS. 14 and 15). The keto form was almost exclusively the 2S diastereomer as determined by $^1$H NOESY and molecular modeling (FIG. 16). The doublet in the $^{19}$F NMR spectrum in CDCl$_3$ at −205.96 ppm was assigned to the 2R keto diastereomer based on $^1$H-$^{19}$F HMBC (FIG. 16C). $^1$H NMR (500 MHz, CDCl$_3$): δ 5.83 (d, J=45.7 Hz, keto H$_2$), 4.71 (ddd, J=8.4, 5.2, 3.0 Hz, keto H$_5$), 4.26 (ddd, J=8.8, 6.0, 3.3 Hz, enol H$_5$), 2.68 (qd, J=7.5, 3.0 Hz, keto H$_4$), 2.45 (qt, J=7.2, 3.8 Hz, enol H$_4$), 1.88-1.78 (m, keto H$_{6a}$), 1.75 (m, enol H$_{6a}$), 1.60 (m, keto H$_{6b}$), 1.55-1.44 (m, enol H$_{6b}$), 1.14 (d, J=7.5 Hz, keto H$_8$), 1.11 (d, J=7.1 Hz, enol H$_8$), 1.00 (t, J=7.4 Hz, keto H$_7$), 0.92 (t, J=7.5 Hz, enol H$_7$). $^{13}$C NMR (151 MHz, CDCl$_3$): δ 198.58 (d, J=13.4 Hz, keto C$_3$), 164.15 (d, J=20.0 Hz, keto C$_1$), 162.67 (d, J=24 Hz, enol C$_1$), 156.94 (d, J=6.5 Hz, enol C$_3$), 130.00 (d, J=232.3 Hz, enol C$_2$), 89.82 (d, J=206.9 Hz, keto C$_2$), 80.27 (enol C$_5$), 77.89 (d, J=1.7 Hz, keto C$_5$), 43.97 (keto C4), 35.84 (enol C$_4$), 24.15 (keto C$_6$), 23.96 (enol C$_6$), 10.38 (d, J=2.7 Hz, enol C$_8$), 10.11 (keto C$_8$), 9.93 (keto C$_7$), 9.72 (enol C$_7$). $^{19}$F NMR (565 MHz, CDCl$_3$, CFCl$_3$=0 ppm): δ −172.36 (d, J=4.3 Hz, enol), −205.96 (d, J=44.9 Hz, 2S keto), −210.40 (d, J=45.6 Hz, 2R keto). $^{19}$F NMR (565 MHz, 10% D$_2$O, 50 mM sodium phosphate pH 4.5): δ −178.66. $^{19}$F NMR (565 MHz, 15% D$_2$O, 85 mM Tris pH 7.5, 5-fluorouracil=−168.3 ppm): δ −190.20. GC-MS: t$_R$, 8.51 min; EI spectrum (FIG. 17). HR-ESI-MS [M−H]$^−$: calculated for C$_8$H$_{10}$FO$_3$, m/z 173.0619. found m/z 173.0617.

GC-MS Analysis of F-TKL

Samples were dissolved in dichloromethane and BSTFA containing 1% trimethylsilyl chloride (Sigma-Aldrich, 0.1 volumes) was added. Samples were analyzed on a Trace GC Ultra (Thermo Scientific) coupled to a DSQII single-quadrupole mass spectrometer using an HP-5MS column (0.25 mm×30 m, 0.25 µM film thickness, J & W Scientific). The injection volume was 1 µL and the oven program was as follows: 75° C. for 3 min, ramp to 25° C. at 25° C. min$^{-1}$, ramp to 300° C. at 50° C. min$^{-1}$, hold for 1 min. The comparison between the synthetic and enzymatic F-TKL is shown in FIG. 17.

Covalent Inhibition Assay for DEBS$_{Mod6}$+TE

Two triketide reaction mixtures (200 µL) were prepared as described above, one containing fluoromalonate (10 mM) and the other methylmalonate (10 mM). DEBS$_{Mod6}$+TE (10 µM) and NDK-SNAC (2.5 mM) were added to each and the reactions were incubated at 37° C. for 18 h. The protein fraction was isolated from each mixture at room temperature by desalting on a Sephadex G-25 column (3 mL) using 400 mM sodium phosphate, pH 7.5. Fractions were pooled by Bradford assay and concentrated to 200 µL using Amicon Ultra spin concentrators (3 kDa MWCO). The isolated DEBS$_{Mod6}$+TE was assayed by adding TCEP (2.5 mM), methylmalonyl-CoA (1 mM) and NDK-SNAC (1 mM) to this mixture to give a final volume of 210 µL and incubating at 37° C. for 3 h, then analyzed by HPLC as described above.

Triketide Lactone Production Using DEBS$_{Mod3/6}$+TE/AT$^0$

All assay mixtures contained 400 mM sodium phosphate, pH 7.5, phosphoenolpyruvate (50 mM), TCEP (5 mM), magnesium chloride (10 mM), ATP (2.5 mM), pyruvate kinase (27 U/mL), myokinase (10 U/mL), methylmalonyl-CoA epimerase (5 µM), CoA (1 mM), MatB (40 µM), methyl- or fluoromalonate (20 mM) and NDK-SNAC (5 mM). When used, DszsAT (5 µM) was also added to the reaction mixture. Reactions were initiated by addition of the appropriate DEBS+TE construct (Mod6 or Mod6/AT$^0$, 10 µM; Mod3 and Mod3/AT$^0$, 5 µM in reactions containing DszsAT and 8 µM otherwise) and incubated at 37° C. for 18-20 h. Aliquots were removed, quenched, processed and analyzed as described above.

Triketide Lactone Production Using DEBS$_{Mod2}$/AT$^0$

All assay mixtures contained 400 mM sodium phosphate, pH 7.5, phosphoenolpyruvate (20 mM), TCEP (5 mM), magnesium chloride (5 mM), ATP (2.5 mM), pyruvate kinase (18 U/mL), myokinase (10 U/mL), methylmalonyl-CoA epimerase (5 µM), CoA (1 mM), MatB (20 µM), NDK-SNAC (500 µM) and either methylmalonate, fluoromalonate or malonate (5 mM) as appropriate. Reactions were initiated by addition of DEBS$_{Mod2}$/AT$^0$ (10 µM) and incubated at 37° C. overnight. Aliquots were removed, quenched by addition of HCl to 1 M, then processed and analyzed as described above.

Tetraketide Lactone Production

All reactions contained 400 mM sodium phosphate (pH 7.5 for the 2,4-dimethyl- and 2-fluoro-4-methyl-tetraketide lactone reactions and pH 6 for the 2-methyl-4-fluoro-tetraketide lactone reaction), glycerol (20%), phosphoenolpyruvate (20 mM), TCEP (10 mM), magnesium chloride (5 mM), ATP (2.5 mM), pyruvate kinase (18 U/mL), myokinase (10 U/mL), methylmalonyl-CoA epimerase (5 µM), MatB (20 µM), CoA (1 mM), methylmalonyl-CoA (100 µM), NDK-SNAC (1 mM) and reduced nicotinamide adenine dinucleotide phosphate (NADPH; 5 mM).

The reaction to produce 2,4-dimethyl-tetraketide lactone also contained methylmalonate (5 mM), DEBS$_{Mod2}$ (10 µM) and DEBS$_{Mod3}$+TE (2 µM). The reaction to produce 2-fluoro-4-methyl-tetraketide lactone also contained fluoromalonate (5 mM), DEBS$_{Mod2}$ (10 µM), DEBS$_{Mod3}$/AT$^0$ (2 µM) and DzAT (2 µM). The reaction to produce 2-methyl-4-fluoro-tetraketide lactone also contained fluoromalonate (5 mM), DEBS$_{Mod2}$/AT$^0$ (10 µM) and DEBS$_{Mod3}$ (2 µM).

All reactions were initialized by the addition of DEBS$_{Mod2}$ or DEBS$_{Mod2}$/AT$^0$ and incubated at 37° C. overnight. Reactions were then saturated with sodium chloride and the aqueous layer was acidified by the addition of 0.1 volumes of 70% perchloric acid and extracted four times into 2 volumes of chloroform. The chloroform layer was concentrated by vacuum centrifugation and the tetraketide lactones were resuspended in water for analysis. Tetraketide lactones were analyzed by LC-MS using a Phenomenex Kinetex XB-C18 1.7 µm 150×2.1 mm column with a mobile phase of ammonium acetate (50 mM) with a gradient from 0 to 60% acetonitrile over 15 min and detected on an Agilent single quadruple mass spectrometer in negative ion mode.

ESI-MS/MS Analysis of Tetraketide Lactones

MS/MS spectra were collected using an LTQ FT (Thermo Scientific). Negative ions were generated using ES and analyzed in linear ion trap mode. MS/MS spectra were collected with the following normalized collision energies: TKL, 26; F-TKL, 35; tetraketide lactones, 26.

Triketide Lactone Production Under Competitive Conditions

For reactions with substrate regeneration, assay mixtures contained 400 mM sodium phosphate, pH 7.5, phosphoenolpyruvate (50 mM), TCEP (5 mM), magnesium chloride (10 mM), ATP (2.5 mM), pyruvate kinase (27 U/mL), myokinase (10 U/mL), methylmalonyl-CoA epimerase (5 µM), NDK-SNAC (15 mM) and DEBS$_{Mod6}$+TE (10 µM). Reactions were initiated by simultaneous addition of MatB (40 µM), fluoromalonyl-CoA (1 µM) and malonyl-CoA (1 µM) and incubated at 37° C. for 18-20 h. Protein was removed by filtration through a 3 kDa NWCO membrane at 14,000×g and the filtrate was analyzed by LC-MS. Standards of H-TKL and F-TKL were prepared using a mock reaction mixture (acyl-CoAs replaced by CoAs and NDK-SNAC replaced by N-acetyl cysteamine) as diluent. TKLs were quantified using single ion monitoring, H-TKL in positive mode and F-TKL in negative mode. For reactions without substrate regeneration, assay mixtures contained 400 mM sodium phosphate, pH 7.5, TCEP (5 mM), methylmalonyl-CoA epimerase (5 µM), NDK-SNAC (3 mM) and DEBS$_{Mod6}$+TE (10 µM). Reactions were initiated by adding fluoromalonyl-CoA (1 mM) and malonyl-CoA (1 mM) simultaneously. The mixtures were incubated at 37° C. for 20 h, then quenched, processed and analyzed as described above. H-TKL was monitored using an Agilent 6130 MS operating in positive ion mode, and the limit of detection was verified by spiking samples to 50 nM H-TKL using a standard solution.

$^{19}$F-NMR Analysis of E. coli

LB (250 mL) containing kanamycin and chloramphenicol (50 µg/mL each) in a 1 L baffled shake flask was inoculated to OD$_{600}$=0.05 with an overnight LB culture of E. coli BAP1 freshly co-transformed with pET28a-His$_6$-MatB.SCo and pTRC33-NphT7-PhaB. Cells were grown, induced, washed and resuspended at OD$_{600}$ 90-110 as described above for F-TKL production in resting cells. To 850 µL of this cell suspension fluoromalonate (43 mM) was added and the cells were incubated at 16° C. for 1 d. Cells were pelleted by centrifugation at 18,000×g and the supernatant (650 µL) was removed. The volume of the supernatant was adjusted to 850 µL by addition of D$_2$O (extracellular fraction). Cells were resuspended in 605 µL potassium phosphate buffer, pH 7.4, and centrifuged again. The supernatant was removed and the cells were resuspended to give a final volume of 850 µL, 17% D$_2$O and 35 mM sodium phosphate pH 7.5. Cells were lysed by sonication and insoluble material removed by centrifugation at 18,000×g for 20 min at room temperature. The supernatant was removed and acidified by addition of 0.025 volumes 70% perchloric acid. Insoluble material was removed by centrifugation at 18,000×g for 20 min and the supernatant was removed. The pH was adjusted to 7 using 10 M sodium hydroxide (intracellular fraction). CFCl$_3$ was added as a chemical shift reference to both the extracellular and intracellular fractions, which were analyzed by $^{19}$F NMR using the ERETIC method.

F-TKL Production in E. coli Cell Lysates

TB (1 L) containing Cb and Km (50 µg/mL each) in a 2.8 L Fernbach baffled shake flask was inoculated to OD$_{600}$=0.05 with an overnight TB culture of E. coli BAP1 freshly co-transformed with pET28a-His$_6$-MatB.SCo/pRSG54 or pET28a/pET16b as the empty vector control. The cultures were grown at 37° C. at 250 rpm to OD$_{600}$=0.6 to 0.8 at which point cultures were cooled on ice for 20 min, followed by induction of protein expression with IPTG (0.2 mM) and overnight growth at 16° C. Cell pellets were harvested by centrifugation at 9,800×g for 7 min at 4° C. and stored at −80° C. Frozen cell pellets were thawed and resuspended at 5 mL/g cell paste with sodium phosphate (500 mM, pH 7.5) and lysed by passage through a French pressure cell at 14,000 psi. The lysate was centrifuged at 15,300×g for 20 min at 4° C. to separate the soluble and insoluble fractions. Assay mixtures (100 µL) containing soluble cell lysate (77 µL), phosphoenolpyruvate (50 mM), TCEP (5 mM), magnesium chloride (10 mM), pyruvate kinase (27 U/mL), myokinase (10 U/mL), methylmalonyl-CoA epimerase (5 µM), fluoromalonate (10 mM), coenzyme A (500 µM), ATP (2.5 mM), and NDK-SNAC (10 mM) were incubated overnight at 37° C. Reactions were quenched by the addition of 70% perchloric acid (5 µL) and insoluble material was removed by centrifugation. Production of F-TKL was analyzed by LC-MS as described above.

F-TKL Production in E. coli Growing and Resting Cell Culture

LB (50 mL) containing carbenicillin and kanamycin (50 µg/mL each) with or without spectinomycin (100 µg/mL) in a 250 mL baffled shake flask was inoculated to OD$_{600}$=0.05 with an overnight LB culture of E. coli BAP1 freshly co-transformed with pET28a-His$_6$-MatB.SCo and the appropriate DEBS+TE plasmid, with or without pCDFDuet-DszsAT.

For F-TKL production in LB, cultures were grown at 37° C. at 200 rpm to OD$_{600}$=0.4 at which point cultures were cooled on ice for 10 min, followed by induction of protein expression with IPTG (0.2 mM). The cultures were grown at 30° C. for 2 h following induction, at which the culture (10 mL) was transferred to a 30 mL tube. Fluoromalonate (50 mM final concentration), diethylfluoromalonate (10 mM final concentration, added as a 1 M solution in DMSO) and either NDK-SNAC (stock, 100 mM solution in 10% DMSO; final, 5 mM) or 10% DMSO were added. The cultures were grown at 30° C. for 20 h. The culture supernatant was collected by centrifugation at 18,000×g for 15 min and acidified by addition of HCl to a final concentration of 1 M. The acidified supernatant was then extracted with 5×3 volumes of dichloromethane and the combined organic layers were concentrated to 5-10 mL by rotary evaporation. The residue was transferred to a silanized glass vial (Sigmacote®, Sigma-Aldrich) and water (200 µL) was added. The dichloromethane was removed from the biphasic mixture by rotary evaporation and the aqueous solution of triketide was analyzed by LC-MS as described above.

For F-TKL production by resting cells, cultures were grown at 37° C. at 200 rpm to OD$_{600}$=0.8-0.9, at which point cultures were cooled on ice for 15 min, followed by induction of protein expression with IPTG (0.2 mM). The cultures were grown at 16° C. for 20-24 h following induction. Cells were collected by slow centrifugation at 1,000×g for 15 min at 4° C. The cells were washed once with 100 mM potassium phosphate, pH 7.4, then resuspended in the same buffer at an OD$_{600}$ of 90-110. To 50 µL of this suspension in a 0.6 mL tube, fluoromalonate (50 mM final concentration) and NDK-SNAC (stock, 100 mM solution in 10% DMSO; final, 5 mM) were added. The cell suspensions were incubated with shaking at 16° C. for 20 h. The culture supernatant was collected by centrifugation at 18,000×g for 15 min and analyzed by LC-MS as described above with no further concentration. The identity of the F-TKL produced in vivo was also confirmed by HR-ESI-MS. HR-ESI-MS [M−H]⁻: calculated for $C_8H_{10}FO_3$, m/z 173.0619. found m/z 173.0619.

Example 2

Supplementary Results

TABLE 1

(A) Strains and plasmids used for this study. (B) Oligonucleotides used for gene and plasmid construction. (C) The primer map for construction of the synthetic nphT7 gene is also shown with non-coding portions in lowercase.

A. Strains and plasmids

| Strain | Genotype | Source |
|---|---|---|
| BL21(de3) | F⁻ ompT gal dcm lon hsdS$_B$(r$_B$⁻ m$_B$⁻) Δ(DE3 [lacI lacUV5-T7 gene 1 ind1 sam7 nin5]) | Novagen |
| BAP1 | F⁻ ompT gal dcm lon hsdS$_B$(r$_B$⁻ m$_B$⁻) Δ(DE3 [lacI lacUV5-T7 gene 1 ind1 sam7 nin5]) ΔprpRBCDE (sfp (T7), prpE (T7))] | Pfeifer, B. A., et al., Science 291:1790-1792 (2001) |

| Plasmid | Description | Source |
|---|---|---|
| pET16b-His$_{10}$-NphT7 | His$_{10}$-nphT7 (T7), lacI, Cb$^r$, ColE1 | This study |
| pET16b-His$_{10}$-AckA.EC | His$_{10}$-ackA.EC (T7), lacI, Cb$^r$, ColE1 | This study |
| pET16b-His$_{10}$-Pta.EC | His$_{10}$-pta.EC (T7), lacI, Cb$^r$, ColE1 | This study |
| pET28a-His$_6$-MatB.SCo | His$_6$-matB.SCo (T7), lacI, Km$^r$, ColE1 | This study |
| pET28a-His$_6$-Epi.SCo | His$_6$-epi.SCo (T7), lacI, Km$^r$, ColE1 | This study |
| pET16b-His$_{10}$-THNS | His$_{10}$-thns (T7), lacI, Cb$^r$, ColE1 | This study |
| pCDFDuet-DszsAT.SCe-MatB.SCo | DszsAT.SCe (T7), matB.SCo (T7), lacI, Sp$^r$, CloDF13 | This study |
| pCDFDuet-ø-MatB.SCo | matB.SCo (T7), lacI, Sp$^r$, CloDF13 | This study |
| pFW3 | DszsAT.SCe-His$_6$ (T7), lacI, Cb$^r$, ColE1 | Wong, F. T., et al., Biochemistry, 49:95-102 (2009) |
| pTRC33-NphT7-PhaB | nphT7.phaB (trc), lacIq, Cb$^r$, M13 | This study |
| pBP19 | DEBS$_{Mod2}$-His$_6$(T7), lacI, Cb$^r$, ColE1 | Tsuji, S. Y., et al., Biochemistry, 40:2326-2331 (2001) |
| pSV272-His$_6$-MBP-DEBS$_{Mod2}$ | His$_6$-MBP-DEBS$_{Mod2}$ (T7), lacI, Km$^r$, ColE1 | This study |
| pSV272-His$_6$-MBP-DEBS$_{Mod2}$/AT$^0$ | His$_6$-MBP-DEBS$_{Mod2}$/AT$^0$ (T7), lacI, Km$^r$, ColE1 | This study |
| pAYC138 | DEBS$_{Mod6}$ + TE/AT$^0$-His$_6$ (T7), lacI, Cb$^r$, ColE1 | Wong, F. T., et al., Biochemistry, 49:95-102 (2009) |
| pRSG54 | DEBS$_{Mod6}$ + TE-His$_6$(T7), lacI, Cb$^r$, ColE1 | Gokhale, R. S., et al., Science, 284:482-485 (1999) |
| pRSG34 | DEBS$_{Mod3}$ + TE-His$_6$(T7), lacI, Cb$^r$, ColE1 | Gokhale, R. S., et al., Science, 284:482-485 (1999) |
| pAYC136 | DEBS$_{Mod3}$ + TE/AT$^0$-His$_6$ (T7), lacI, Cb$^r$, ColE1 | Wong, F. T., et al., Biochemistry, 49:95-102 (2009) |
| pRARE2 | ileX, argU, thrU, tyrU, glyT, thrT, argW, metT, leuW, proL, laI, Cm$^r$, p15a | Novagen |
| pBAD33-BirA | birA.EC (ara), araC, Cm$^r$, p15a | This study |

B. Oligonucleotide sequences

| Name | Sequence |
|---|---|
| nphT7 R1 | aaacgaacgtcggtcatggtg |
| nphT7 F1 | caccatgaccgacgttcgtttcgtatcattggcacgggt |
| nphT7 R2 | gctccggcacgtacgcacccgtgccaatgatacga |
| nphT7 F2 | gcgtacgtgccggagcgtattgtgtccaacgacgaggt |
| nphT7 R3 | accagccggcgcacccacctcgtcgttggacacaatac |
| nphT7 F3 | gggtgcgccggctggtgttgatgatgactggattacccgt |

TABLE 1-continued (A) Strains and plasmids used for this study. (B) Oligonucleotides used for gene and plasmid construction. (C) The primer map for construction of the synthetic nphT7 gene is also shown with non-coding portions in lowercase.

| | |
|---|---|
| nphT7 R4  | cgttgacgaatgccggtcttacgggtaatccagtcatcatcaac |
| nphT7 F4  | aagaccggcattcgtcaacgtcgttgggcggcggac |
| nphT7 R5  | tcggaggtcgcttggtcgtccgccgcccaacga |
| nphT7 F5  | gaccaagcgacctccgacctggcaaccgcggcg |
| nphT7 R6  | tcaacgccgcacgacccgccgcggttgccagg |
| nphT7 F6  | ggtcgtgcggcgttgaaagcagcgggtattacgcc |
| nphT7 R7  | gcaataaccgtcagttgctccggcgtaatacccgctgctt |
| nphT7 F7  | ggagcaactgacggttattgcggtcgcaacgtccaccc |
| nphT7 R8  | ggctgcggacggtccggggtggacgttgcgacc |
| nphT7 F8  | cggaccgtccgcagccgccgacggcggcctac |
| nphT7 R9  | cgcccagatgatgttgcacgtaggccgccgtcggc |
| nphT7 F9  | gtgcaacatcatctgggcgcaaccggcaccgcggc |
| nphT7 R10 | tgcacacagcgttaacatcaaatgccgcggtgccggttg |
| nphT7 F10 | atttgatgttaacgctgtgtgcagcggcacggttttgct |
| nphT7 R11 | ccgccacgctggacagagcaaaaaccgtgccgc |
| nphT7 F11 | ctgtccagcgtggcgggcacgctggtgtatcgtgg |
| nphT7 R12 | caatgaccagtgcgtaaccgccacgatacaccagcgtgc |
| nphT7 F12 | cggttacgcactggtcattggtgccgatctgtattcccgta |
| nphT7 R13 | ggtccgccggattcagaatacgggaatacagatcggcac |
| nphT7 F13 | ttctgaatccggcggaccgcaagaccgttgttctgtttgg |
| nphT7 R14 | cgcacccgcgccgtcaccaaacagaacaacggtcttgc |
| nphT7 F14 | tgacggcgcgggtgcgatggtgctgggtccgac |
| nphT7 R15 | acccgtacccgtgctggtcggacccagcaccat |
| nphT7 F15 | cagcacgggtacgggtccgatcgtccgtcgcg |
| nphT7 R16 | caaacgtgtgcagggcaacgcgacggacgatcgg |
| nphT7 F16 | ttgccctgcacacgtttggtggtctgaccgacctgatt |
| nphT7 R17 | cacccgccggcacacgaatcaggtcggtcagaccac |
| nphT7 F17 | cgtgtgccggcgggtggcagccgccaaccgct |
| nphT7 R18 | tccaagccatccgtgtccagcggttggcggctgc |
| nphT7 F18 | ggacacggatggcttggacgcgggtctgcaatacttcg |
| nphT7 R19 | cctcgcgaccgtccatagcgaagtattgcagacccgcg |
| nphT7 F19 | ctatggacggtcgcgaggtgcgtcgttttgttaccgaac |
| nphT7 R20 | cctttaatcagttgcggcaagtgttcggtaacaaaacgacgca |
| nphT7 F20 | acttgccgcaactgattaaaggtttcttgcacgaggcggg |
| nphT7 R21 | gctaatatctgccgcatcgacacccgcctcgtgcaagaaa |
| nphT7 F21 | tgtcgatgcggcagatattagccattttgtgccgcaccaagc |
| nphT7 R22 | cgtccagcatgacaccgttcgcttggtgcggcacaaaatg |
| nphT7 F22 | gaacggtgtcatgctggacgaggtctttggtgaactgcacc |

TABLE 1-continued (A) Strains and plasmids used for this study. (B) Oligonucleotides used for gene and plasmid construction. (C) The primer map for construction of the synthetic nphT7 gene is also shown with non-coding portions in lowercase.

| | |
|---|---|
| nphT7 R23 | atggtcgcacgcggcaggtgcagttcaccaaagacct |
| nphT7 F23 | tgccgcgtgcgaccatgcaccgtaccgtcgaaacc |
| nphT7 R24 | cgcacccgtattgccgtaggtttcgacggtacggtgc |
| nphT7 F24 | tacggcaatacgggtgcggccagcattccgattacgatg |
| nphT7 R25 | tgcacggactgctgcatccatcgtaatcggaatgctggc |
| nphT7 F25 | gatgcagcagtccgtgcaggtagcttccgtccggg |
| nphT7 R26 | gccagcaggaccagttcacccggacggaagctacc |
| nphT7 F26 | tgaactggtcctgctggcgggttttggtggtggcatg |
| nphT7 R27 | gcgcgaagctcgctgccatgccaccaccaaaaccc |
| nphT7 F27 | gcagcgagcttcgcgctgatcgagtggtaagtcagcc |
| nphT7 R28 | acccgctctagccgtcaggctgacttaccactcgatca |
| nphT7 F28 | tgacggctagagcgggt |
| NphT7 G F | aatttcacacgagctcggtacccgggaggagatataccatgaccgacgttcgttttcg |
| NphT7 G R | gcgctgggtcattatatatctccttttcttaccactcgatcagcgcgaag |
| PhaB F | gaaaaggagatatataatgacccagcgcatcgcttacgtaacc |
| PhaB R | gcttgcatgcctgcaggtcgactctagaggatctcatgccttggctttgacgtatc |
| MatB.SCo F | tcgattgcacatatgtcctctctcttcccggccctct |
| MatB.SCo R | atcggatagctcgagtcagtcacggttcagcgcccgctt |
| Epi.SCo F | atcccgaatcatatgctgacgcgaatcgacca |
| Epi.SCo R | ttagtctggctcgagtcagtgctcaggtgactcaa |
| AckA.EC F | ggagatatacatatgtcgagtaagttag |
| AckA.EC R | attggatcctctagatcaggcagtcaggcg |
| Pta.EC F | attcatatgtcccgtattattatgctgatc |
| Pta.EC R | attctcgaggagggtaccgacgtcttac |
| THNS.SCo F | attcatatggcgactttgtgcagaccctcggtgtccgtcccggagc |
| THNS.SCo R | attactagttcatgcctgcctcaccctccgcgacacgccccgtg |
| pCDF-MatB.SCo F | ttagttaagtataagaaggagatatacatatgtcctctctcttcccggccctct |
| pCDF-MatB.SCo R | gtttctttaccagactcgagggtacctcagtcacggttcagcgcccg |
| pCDF-DszsAT.SCe F | gtttaactttaataaggagatataccatgaaagcatacatgtttcccgggc |
| pCDF-DszsAT.SCe R | cttaagcattatgcggccgcaagcttgttacgacgacgaggggctggg |
| MBP-M2 F | gggatcgaggaaaacctgtattttcagggcatgagcggtgacaacggcatgaccgagg |
| MBP-M2 R | gcttgtcgacggagctcgaattcggggatcctcagtggtggtggtggtggtgctcgagtg |
| MBP-M2ATnull F | gttatcggtcacgcgcagggtgaaatcgcggccgcggtggtggcgggagcgttgtcgctg |
| MBP-M2ATnull R | cgcgatttcaccctgcgcgtgaccgataacggccgaaggaacggcaccgcaggcacgcca |

C. Primer map for synthetic nphT7 construction caccATGACC GACGTTCGTT TTCGTATCAT TGGCACGGGT GCGTACGTGC gtggTACTGG CTGCAAGCAA AAGCATAGTA ACCGTGCCCA CGCATGCACG

TABLE 1-continued (A) Strains and plasmids used for this study. (B) Oligonucleotides used for gene and plasmid construction. (C) The primer map for construction of the synthetic nphT7 gene is also shown with non-coding portions in lowercase.

CGGAGCGTAT TGTGTCCAAC GACGAGGTGG GTGCGCCGGC

TGGTGTTGAT

GCCTCGCATA ACACAGGTTG CTGCTCCACC CACGCGGCCG

ACCACAACTA

GATGACTGGA TTACCCGTAA GACCGGCATT CGTCAACGTC

GTTGGGCGGC

CTACTGACCT AATGGGCATT CTGGCCGTAA GCAGTTGCAG

CAACCCGCCG

GGACGACCAA GCGACCTCCG ACCTGGCAAC CGCGGCGGGT

CGTGCGGCGT

CCTGCTGGTT CGCTGGAGGC TGGACCGTTG GCGCCGCCCA

GCACGCCGCA

TGAAAGCAGC GGGTATTACG CCGGAGCAAC TGACGGTTAT

TGCGGTCGCA

ACTTTCGTCG CCCATAATGC GGCCTCGTTG ACTGCCAATA

ACGCCAGCGT

ACGTCCACCC CGGACCGTCC GCAGCCGCCG ACGGCGGCCT

ACGTGCAACA

TGCAGGTGGG GCCTGGCAGG CGTCGGCGGC TGCCGCCGGA

TGCACGTTGT

TCATCTGGGC GCAACCGGCA CCGCGGCATT TGATGTTAAC

GCTGTGTGCA

AGTAGACCCG CGTTGGCCGT GGCGCCGTAA ACTACAATTG

CGACACACGT

GCGGCACGGT TTTTGCTCTG TCCAGCGTGG CGGGCACGCT

GGTGTATCGT

CGCCGTGCCA AAAACGAGAC AGGTCGCACC GCCCGTGCGA

CCACATAGCA

GGCGGTTACG CACTGGTCAT TGGTGCCGAT CTGTATTCCC

GTATTCTGAA

TABLE 1-continued (A) Strains and plasmids used for this study. (B) Oligonucleotides used for gene and plasmid construction. (C) The primer map for construction of the synthetic nphT7 gene is also shown with non-coding portions in lowercase.

CCGCCAATGC GTGACCAGTA ACCACGGCTA GACATAAGGG

CATAAGACTT

TCCGGCGGAC CGCAAGACCG TTGTTCTGTT TGGTGACGGC

GCGGGTGCGA

AGGCCGCCTG GCGTTCTGGC AACAAGACAA ACCACTGCCG

CGCCCACGCT

TGGTGCTGGG TCCGACCAGC ACGGGTACGG GTCCGATCGT

CCGTCGCGTT

ACCACGACCC AGGCTGGTCG TGCCCATGCC CAGGCTAGCA

GGCAGCGCAA

GCCCTGCACA CGTTTGGTGG TCTGACCGAC CTGATTCGTG

TGCCGGCGGG

CGGGACGTGT GCAAACCACC AGACTGGCTG GACTAAGCAC

ACGGCCGCCC

TGGCAGCCGC CAACCGCTGG ACACGGATGG CTTGGACGCG

GGTCTGCAAT

ACCGTCGGCG GTTGGCGACC TGTGCCTACC GAACCTGCGC

CCAGACGTTA

ACTTCGCTAT GGACGGTCGC GAGGTGCGTC GTTTTGTTAC

CGAACACTTG

TGAAGCGATA CCTGCCAGCG CTCCACGCAG CAAAACAATG

GCTTGTGAAC

CCGCAACTGA TTAAAGGTTT CTTGCACGAG GCGGGTGTCG

ATGCGGCAGA

GGCGTTGACT AATTTCCAAA GAACGTGCTC CGCCCACAGC

TACGCCGTCT

TATTAGCCAT TTTGTGCCGC ACCAAGCGAA CGGTGTCATG

CTGGACGAGG

ATAATCGGTA AAACACGGCG TGGTTCGCTT GCCACAGTAC

GACCTGCTCC

TABLE 1-continued (A) Strains and plasmids used for this study. (B) Oligonucleotides used for gene and plasmid construction. (C) The primer map for construction of the synthetic nphT7 gene is also shown with non-coding portions in lowercase.

```
TCTTTGGTGA ACTGCACCTG CCGCGTGCGA CCATGCACCG

TACCGTCGAA

AGAAACCACT TGACGTGGAC GGCGCACGCT GGTACGTGGC

ATGGCAGCTT

ACCTACGGCA ATACGGGTGC GGCCAGCATT CCGATTACGA

TGGATGCAGC

TGGATGCCGT TATGCCCACG CCGGTCGTAA GGCTAATGCT

ACCTACGTCG

AGTCCGTGCA GGTAGCTTCC GTCCGGGTGA ACTGGTCCTG

CTGGCGGGTT

TCAGGCACGT CCATCGAAGG CAGGCCCACT TGACCAGGAC

GACCGCCCAA

TTGGTGGTGG CATGGCAGCG AGCTTCGCGC TGATCGAGTG GTAAgtcagc ctgacggcta gagcgggt

AACCACCACC GTACCGTCGC TCGAAGCGCG ACTAGCTCAC CATTcagtcg gactgccgat ctcgccca
```

TABLE 2

Rates of acyl-CoA hydrolysis by DEBS$_{Mod6}$ + TE. Steady-state hydrolysis rates were measured using DEBS$_{Mod6}$ + TE (1 µM) and acyl-CoA (500 µM). Values are reported as the mean ± s.d. (n = 4).

| | $v_0$ (µM min$^{-1}$) | Relative rate |
|---|---|---|
| Methylmalonyl-CoA | 1.36 ± 0.05 | 1.0 |
| Fluoromalonyl-CoA | 3.5 ± 0.3 | 2.6 |
| Malonyl-CoA | 6.1 ± 0.4 | 4.5 |

TABLE 3

F-TKL and H-TKL production under competitive conditions. DEBS$_{Mod6}$ + TE was incubated with equimolar amounts of malonyl-CoA and fluoromalonyl-CoA (1 mM). Without substrate regeneration, no detectable H-TKL was formed (<50 nM). MatB and regeneration enzymes were then included to amplify and quantify H-TKL formation. Values are reported as the mean ± s.d. (n = 3).

| Condition | [F-TKL] (nM) | [H-TKL] (nM) | [F-TKL]/[H-TKL] |
|---|---|---|---|
| No regeneration | 450 ± 60 | <50 | >9 |
| MatB regeneration | 7,390 ± 520 | 720 ± 50 | 10.3 ± 0.1 |

TABLE 4

Concentrations of extra- and intracellular organofluorines in fluorohydroxybutyrate-producing cells. Fluoromalonate (42 mM) was added to a suspension of cells expressing MatB, NphT7, and PhaB. Organofluorine concentrations were determined by $^{19}$F NMR using the ERETIC method and normalized to the total suspension volume, of which the wet cell pellet constituted 33%. Chemical shifts are reported relative to the internal standard (CFCl$_3$).

| | | Concentration (mM) | |
|---|---|---|---|
| Species | ∂ (ppm) | Extracellular | Intracellular |
| Fluoromalonate | −178.3 | 36.9 | 0.9 |
| Fluorohydroxybutyrate | −197.4 | 0.2 | 0.1 |
| Fluoroacetate | −217.9 | 1.1 | 0.2 |

Scheme 1. Hydrolysis and regeneration reactions for F-TKL production by DEBS$_{Mod6}$+TE. Reaction scheme showing enzymes present in F-TKL forming reactions including observed non-productive hydrolysis reactions (red) and the ATP regenerating system (blue).

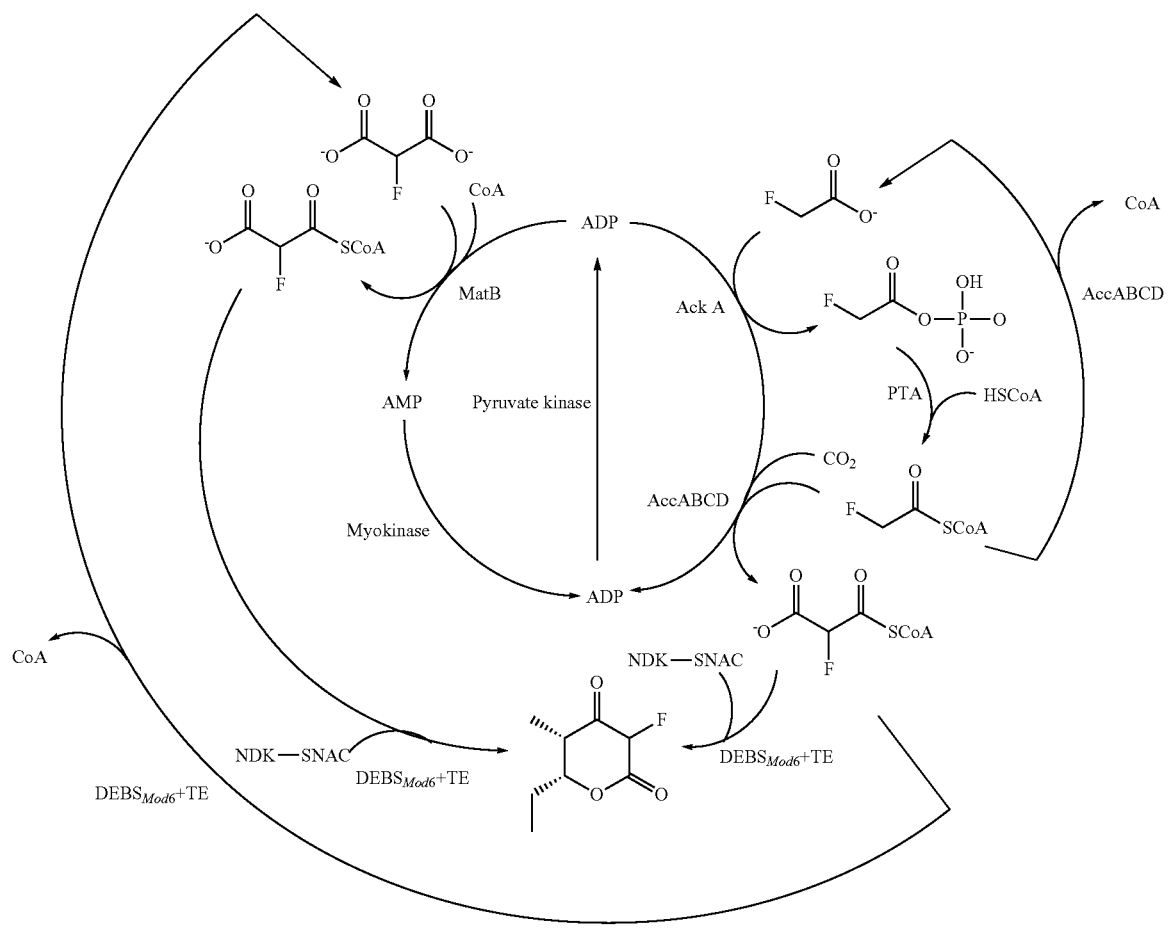

Results and Discussion

The introduction of fluorine via synthetic or semisynthetic routes has enabled the improvement of the clinical properties of several natural products but remains challenging to achieve (Rivkin, et al., *Org. Lett.*, 4:4081-4084 (2002); Bégué, et al., *J. Fluorine Chem.*, 127:992-1012 (2006); Llano-Sotelo, et al., *Antimicrob. Agents Chemother*, 54:4961-4970 (2010); and Mo, et al., *J. Am. Chem. Soc.*, 133:976-985 (2010)). While previous studies have shown that distal fluorine substituents can be accommodated in natural product biosynthetic pathways (Runguphan, et al., *Proc. Natl. Acad. Sci. U.S.A.*, 106:13673-13678 (2009); and Goss, et al., *ChemBioChem*, 11:698-702 (2010)), access to fluoromalonyl-CoA, a fluorinated analog of one of nature's most powerful carbon nucleophiles, as an extender unit would enable a general method for direct incorporation of fluorine into any polyketide structure.

Figure 1B:
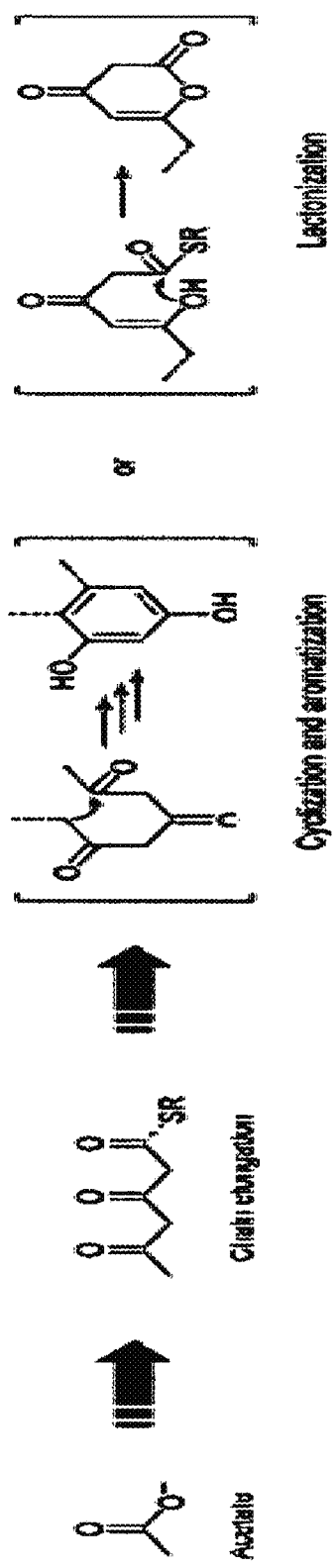

Many acetate-based natural products, polyketides in particular, are generated through the iterative condensation of activated thioesters, resulting in reactive β-keto units that condense further to produce a wide range of structures (Staunton, et al., *Nat. Prod. Rep.* 18, 380-416 (2001); Croteau, et al., in *Biochemistry and molecular biology of plants*, R. B. Buchanan, W. Gruissem, R. Jones, Eds. (ASPB, Rockville, Md., 2000) pp. 1250-1318)). (FIG. 1B). The structural diversity of polyketides is especially striking given that the majority of polyketides draw on only two monomers, acetate and propionate, as the extender units that form their carbon skeletons (Cane, et al., *Science*, 282:63-68 (1998); Staunton, et al., *Nat. Prod. Rep.*, 18:380-416 (2001); and Chan, et al., *Nat. Prod. Rep.*, 26:90-114 (2009)). Although polyketide synthases (PKSs) have been observed to be promiscuous with regard to their starter units (McDaniel et al., *Proc. Natl. Acad. Sci. U.S.A.*, 96:1846-1851 (1999)), the encoding of extender units has been found to be quite selective and many cellular acyl-CoAs are excluded from the backbone (Chan, et al., *Nat. Prod. Rep.*, 26:90-114 (2009)). However, progress in engineering extender unit incorporation has been made by domain engineering (McDaniel, et al., *Proc. Natl. Acad. Sci. U.S.A.*, 96:1846-1851 (1999); Sundermann, et al., *ACS Chem. Biol.*, 8:443-450 (2012); and Koryakina, et al., *Org. Biomol. Chem.*, 4449-4458 (2013)) or incorporation via a domain that encodes a rare extender unit (Mo, et al., *J. Am. Chem. Soc.*, 133:976-985 (2010); and Eustaquio, et al., *J. Nat. Prod.*, 73:378-382 (2010)). Although fluoroacetate serves as a starter unit in nature to produce highly toxic ω-fluorofatty acids (FIG. 1A) (D. O'Hagan, *J. Fluorine Chem.*, 127:1479-1483 (2006)), fluorine has never been observed to date within the backbone, implying that chain extension reactions with the fluorinated acyl-CoA do not occur in these systems. The apparent inability of living systems to utilize fluoroacetate for the biosynthesis of complex small molecules likely results in part from the extreme properties of fluorine that affect biological as well as chemical synthesis. For example, the pKa of the α-proton, electrophilicity of the carbonyl group, and the stability of the acyl-CoA and its corresponding carbanion are all highly impacted by fluorine substitution. Furthermore, the fluoroacetyl group bears a clear similarity to the fluoromethylketone motif used for the design of covalent inhibitors, suggesting that the irreversible alkylation of active-site nucleophiles could also create problems (Powers, et al., Chem. Rev., 102:4639-4750 (2002)). Thus, the development of a system to incorporate fluorinated extender units could dramatically increase the range of complex structures that can be accessed but must also address the challenges involved in activating the fluoroacetate monomer for the downstream CC bond forming chemistry involved in chain extension reactions.

Figure 2A:
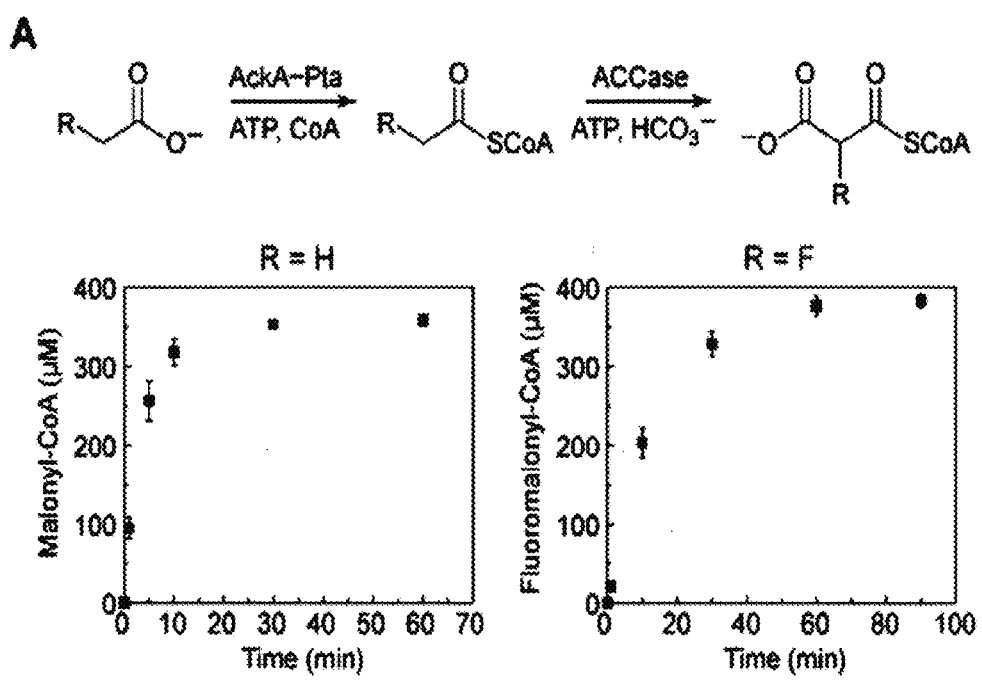
FIG. 2A-D. Enzymatic production of activated extender units for CC bond formation reactions. (A) Formation of malonyl-CoA (left) and fluoromalonyl-CoA (right) from 500 µM CoA and either acetate or fluoroacetate, respectively (AckA, acetate kinase; Pta, phosphotransacetylase; ACCase, acetyl-CoA carboxylase). Values are reported as the mean±s.d. (n=3). (B) Kinetic parameters for malonate activation (MatB, malonyl-CoA synthetase). Kinetic parameters are reported as mean±s.e. (n=3) as determined from non-linear curve-fitting. Error in the $k_{cat}/K_M$ parameter was obtained from propagation of error from the individual kinetic terms. (C) Reaction catalyzed by $DEBS_{Mod6}$+TE using the NDKSNAC substrate with various extender units (NDK-SNAC, native diketide N-acetylcysteamine thioester, (2S,3R)-2-methyl-3-hydroxypentanoyl-Nacetylcysteamine thioester). (D) Chain extension by $DEBS_{Mod6}$+TE to form triketide lactones monitored by LC-MS [TKL, mass/charge ratio (m/z) =169; F-TKL, m/z=173]. CoA, APT, and APT regeneration system are included in all in vitro reactions. Data are normalized with respect to the TKL peak.
Figure 2B:
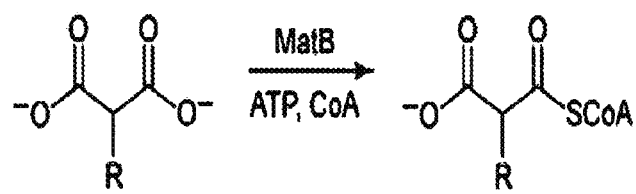
Figure 2C:
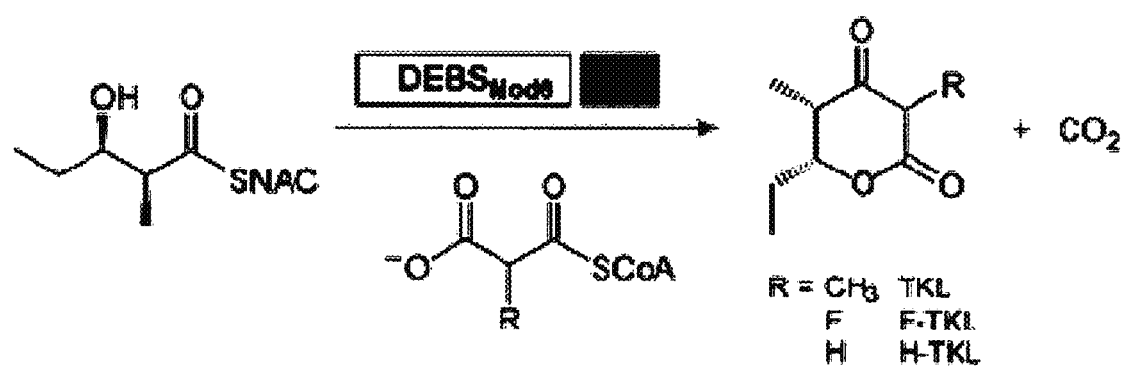
Figure 2D:
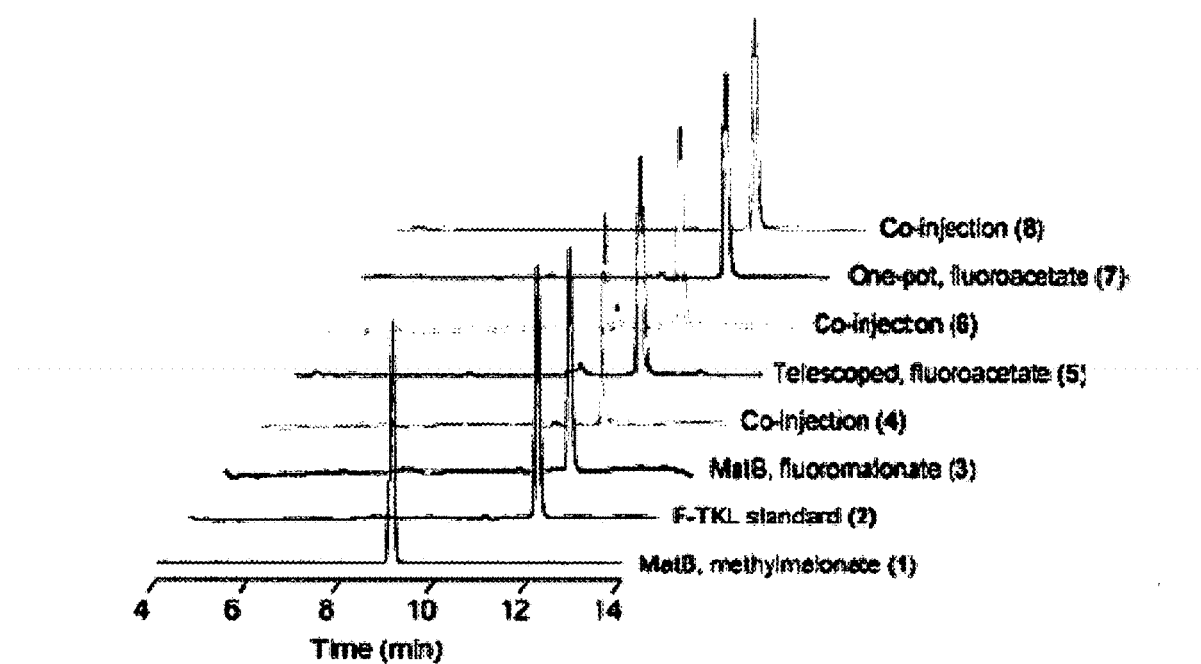
Figure 5A:
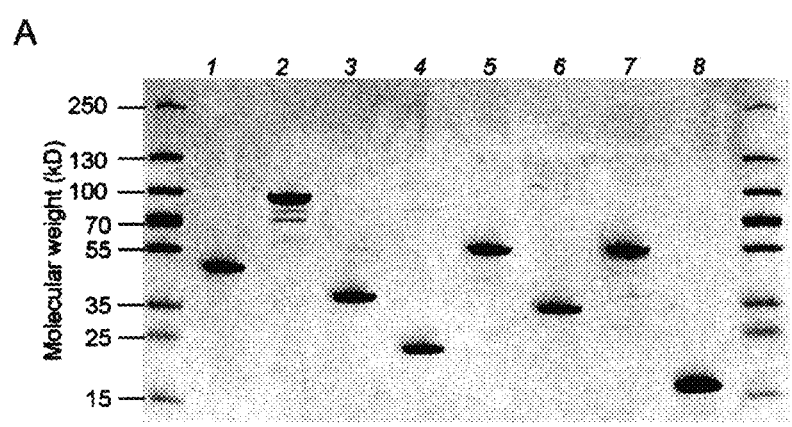
FIG. 5A-B. SDS-PAGE gels of purified proteins. (A) Enzymes used in generation of malonyl-CoA extender units (1, AckA; 2, Pta; 3, AccA; 4, AccB; 5, AccC; 6, AccD; 7, MatB; 8, Epi). (B) Enzymes used for chain extension reactions (9, THNS; 10, NphT7). (C) Enzymes used for polyketide production (11, $DEBS_{Mod2}$; 12, $DEBS_{Mod2}/AT^0$; 13, $DEBS_{Mod3}$+TE; 14, $DEBS_{Mod3}/AT^0$+TE; 15, $DEBS_{Mod6}$+TE; 16, $DEBS_{Mod6}/AT^0$+TE; 17, DszsAT).
Figure 5B:
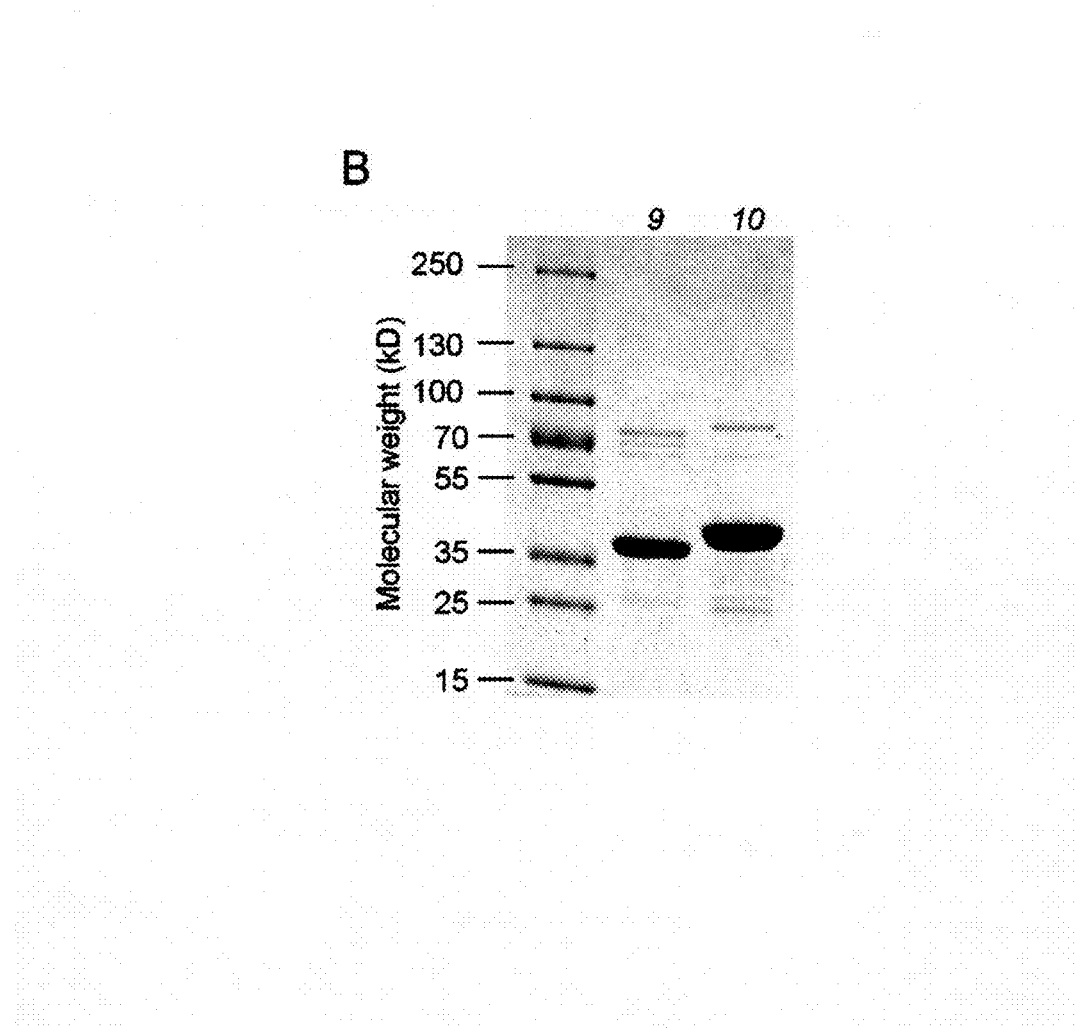
Figure 5C:
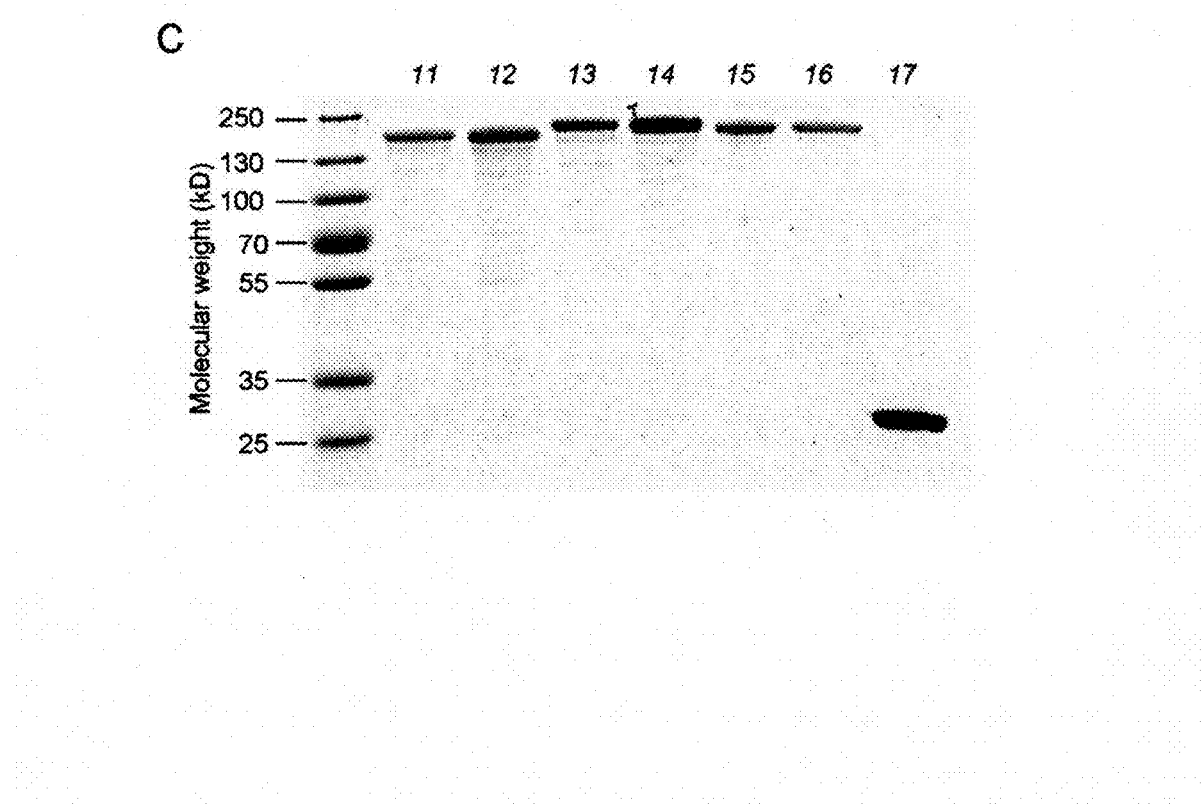
Figure 6A:
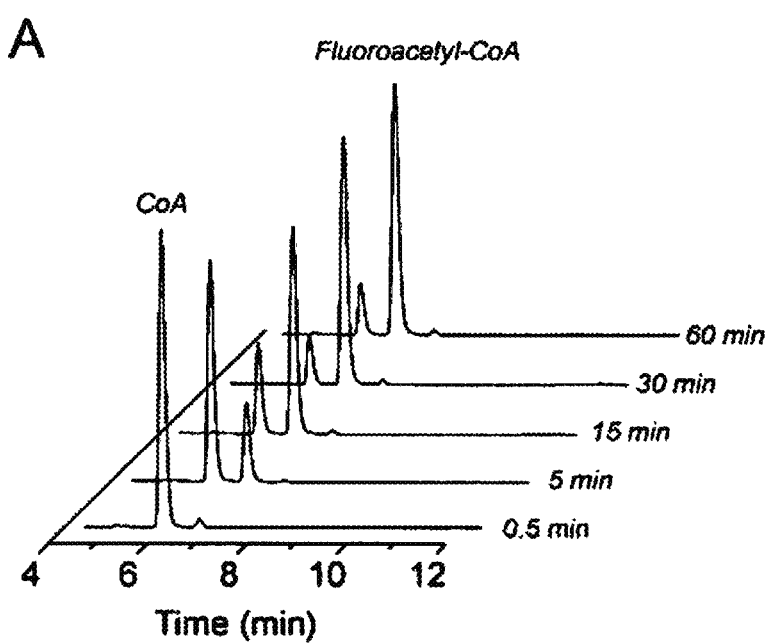
Figure 6B:
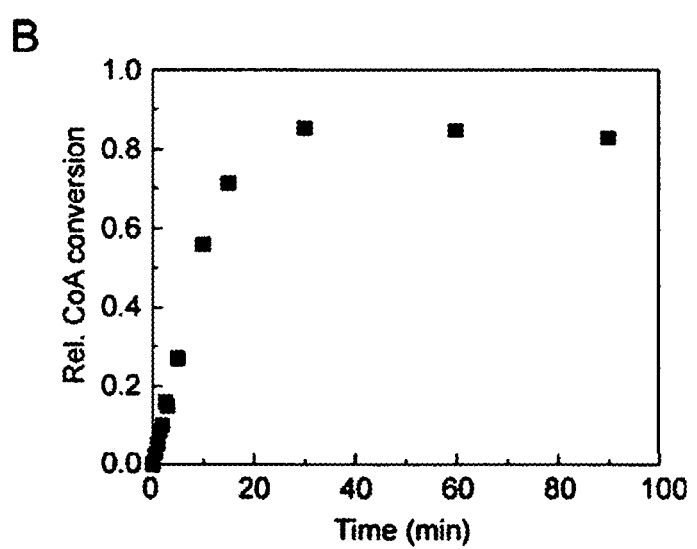
Figure 7A:
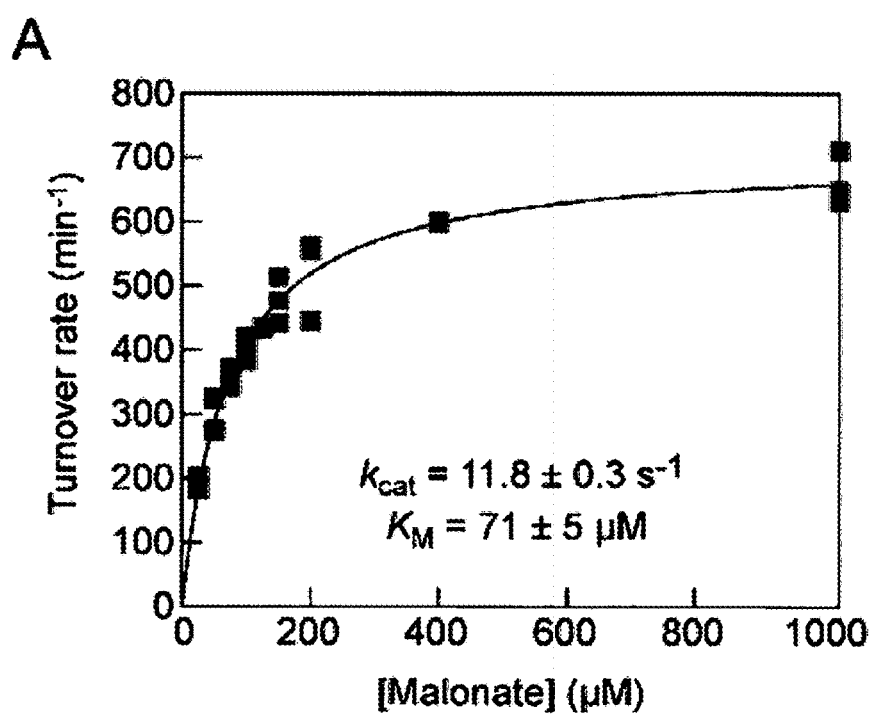
FIG. 7A-C. Steady state kinetic analysis of MatB. (A) Malonate. (B) Methylmalonate. (C) Fluoromalonate. Values are reported as the mean±s.e as determined from nonlinear curve fitting.
Figure 7B:
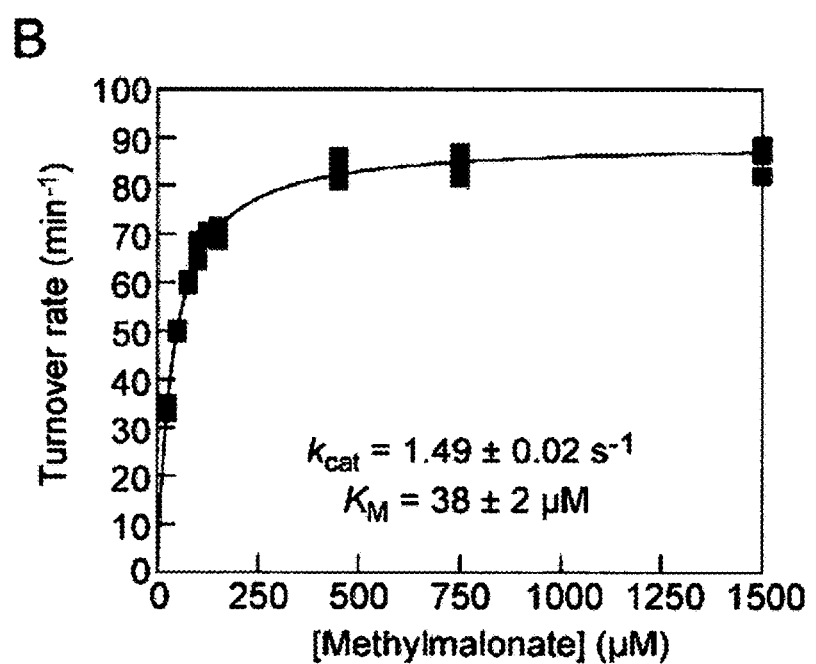
Figure 7C:
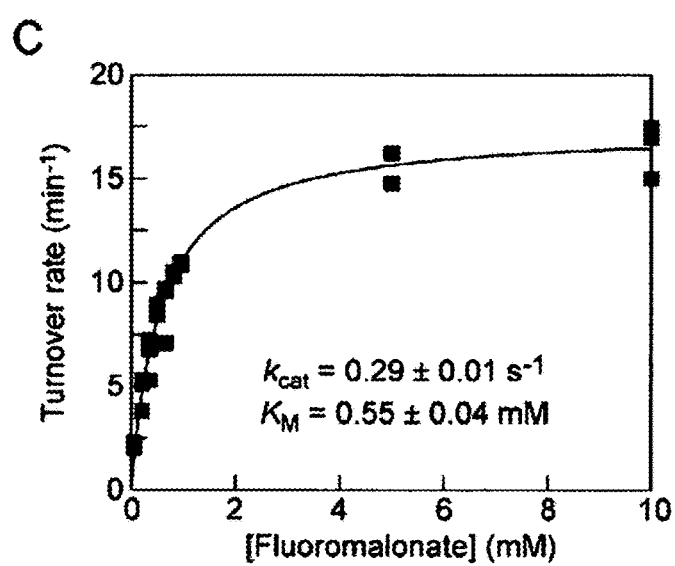
Figure 9:
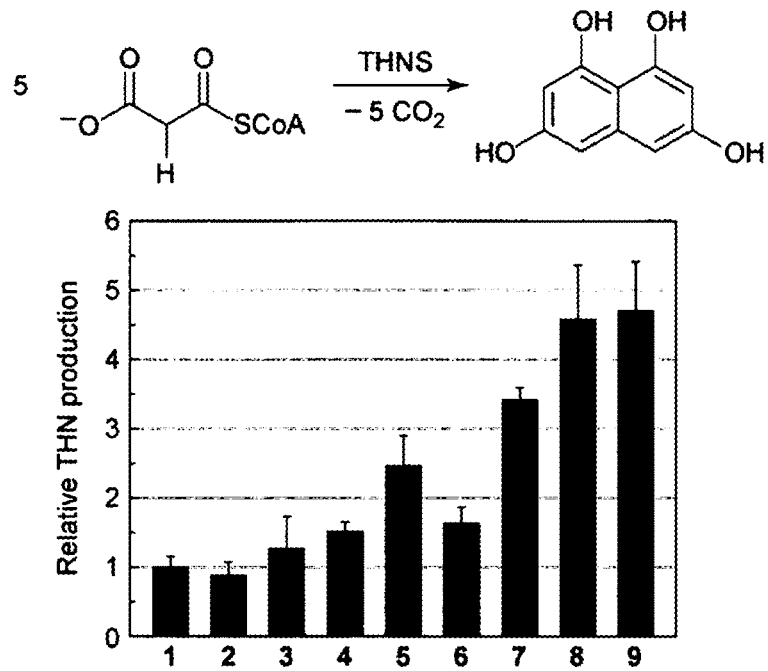
FIG. 9. Efficiency of polyketide production with tetrahydroxynaphthalene synthase (THNS) using different extender regeneration systems. THNS uses only malonyl-CoA as both starter and extender unit (Kumar, et al., Method. Enzymol., 269-293 (2004)). All samples contained a fixed amount of malonyl- or acetyl-CoA (0.5 mM), and relative THN production was monitored at $A_{510\ nm}$. Samples with no regeneration system (1, 2) were compared to those containing regeneration systems related to non-productive decarboxylation (3, 4) and hydrolysis (5), while also providing additional substrate (5-9) in situ. Values are reported as the mean±s.d. (n=3).

Chain elongation in polyketides and related fatty acid-based natural products relies on a separate pool of extender units formed by carboxylation of acyl-CoAs at the α-position. These malonyl-CoA derivatives are then used as masked enolates for CC bond formation following decarboxylation. The fluorinated extender, fluoromalonyl-CoA, can be made through two routes: either a two-step activation of the biogenic fluoroacetate or a direct ligation of CoA to fluoromalonate (FIG. 2). We reasoned that the acetate kinase (AckA) phosphotransacetylase (Pta) pair would be effective at fluoroacetate activation, as mutations in this gene locus have been shown to lead to fluoroacetate resistance in Escherichia coli (Brown, et al., J. Gen. Microbiol., 102:327-336 (1977)). The enzymes from E. coli were thus overexpressed and characterized biochemically, confirming that AckA and Pta serve as an effective activation system to rapidly produce both acetyl- and fluoroacetyl-CoA in nearly quantitative yield (FIGS. 5 and 6). Analysis of the kinetic parameters for these enzymes with respect to fluorinated substrates indicated that neither appears to be affected by the fluorine substituent beyond inductive effects that alter the nucleophilicity of the carboxylic acid (AckA) or electrophilicity of the carbonyl (Pta). Next, we purified the individual AccABCD subunits that make up the acetyl-CoA carboxylase (ACCase) from E. coli and added these enzymes to the AckAPta system in order to carry out the carboxylation of fluoroacetate in a one-pot reaction to generate the fluoromalonyl-CoA extender unit (FIG. 2A, FIG. 5). Under these conditions, the ligation of CoA with AckAPta to produce the acyl-CoA is rapid and production of the carboxylated product is limited by the ACCase. Although the rate of conversion is 4.5-fold slower for fluoroacetate compared to acetate, the overall extent of reaction is similar for both congeners and suggests that covalent inactivation of the ACCase by fluoroacetyl-CoA is not significant. In addition to the route from fluoroacetate, we also tested a malonyl-CoA synthetase (MatB) (Hughes, et al., Chem. Biol., 18:165-176 (2011)) for coupling CoA directly to fluoromalonate. Although MatB exhibits a 103-fold selectivity for malonate over fluoromalonate, fluoromalonyl-CoA is still produced at reasonable efficiency (FIG. 2B, FIGS. 7 and 8). Both of these systems also provide in situ regeneration capacity that can amplify product yields from polyketide synthases and we found that either system increased polyketide production by tetrahydroxynaphthalene synthase (Izumikawa, et al., J. Ind. Microbiol. Biot., 30:510-515 (2003)) compared to simple addition of malonyl-CoA (FIG. 9).

Figure 3A:
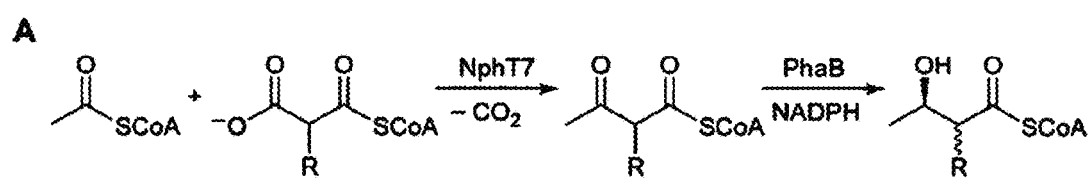
FIG. 3A-B. A chain extension and ketoreduction cycle with a fluorinated extender using a simple polyketide synthase, NphT7. (A) Reactions catalyzed by NphT7 and PhaB. (B) Steady-state kinetic parameters for NphT7-catalyzed C—C bond formation measured using a coupled assay with PhaB. Data points are reported as the mean±s.d. (n=3). Kinetic parameters are reported as mean±s.e. (n=3) as determined from non-linear curve-fitting. Error in the $k_{cat}/K_M$ parameter was obtained from propagation of error from the individual kinetic terms.
Figure 3B:
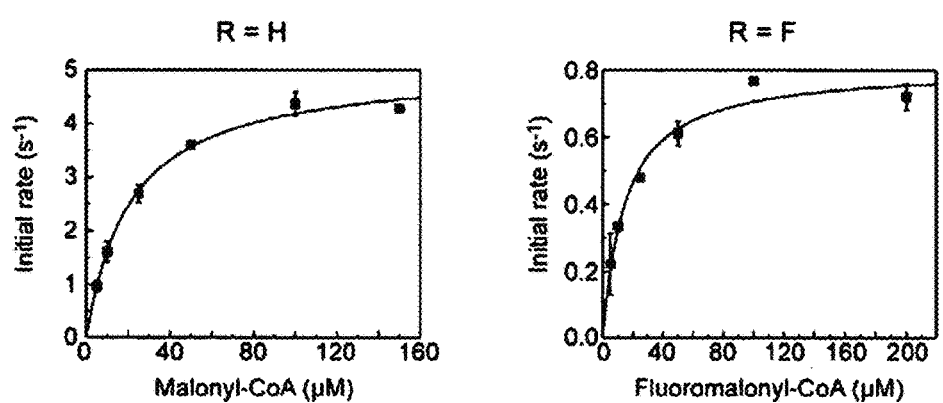
Figure 10:
FIG. 10. Structural alignment of NphT7 and the $DEBS_{Mod5}$ ketosynthase (KS) domain. The NphT7 structure was predicted using Phyre2 (Kelley, et al., Nat. Prot., 4:363-371 (2009)) and based on a type III 3-oxoacyl-(acyl-carrier protein) synthase from Burkholderia xenovorans (PDB ID 4EFI). Despite low sequence identity (<20%), the predicted structure overlays well with the KS domain from $DEBS_{Mod5}$ (Tang, et al., Proc. Nat. Ac. Sc U.S.A., 103:11124-11129 (2006)). Active site residues (C119, H334 H374 (N in NphT7); DEBS numbering) are highlighted.
Figure 11A:
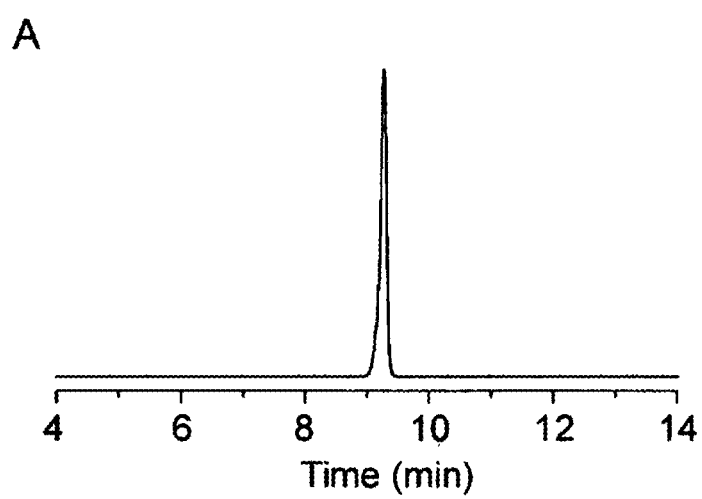
FIG. 11. Characterization of enzymatically synthesized 2-fluoro-3-hydroxybutyryl-CoA. (A) LC/MS trace of 2-fluoro-3-hydroxybutyryl-CoA isolated from enzymatic reaction mixtures (m/z 872). (B) $^{19}F$ NMR spectrum indicates that both diastereomers are produced. (C) $^1H$-$^{19}F$ HMBC in $D_2O$. Based on data from other -fluoroalcohols (Mohanta, et al., J. Am. Chem. Soc., 127:11896-11897 (2005)), the $^{19}F$ resonance for the anti configuration of the fluorine and hydroxyl groups should be found upfield of the syn and was assigned as the major product. If PhaB maintains its native selectivity as an R-specific acetoacetyl-CoA reductase, the anti product is (2S,3R)-2-fluoro-3-hydroxybutyryl-CoA.
Figure 11B:
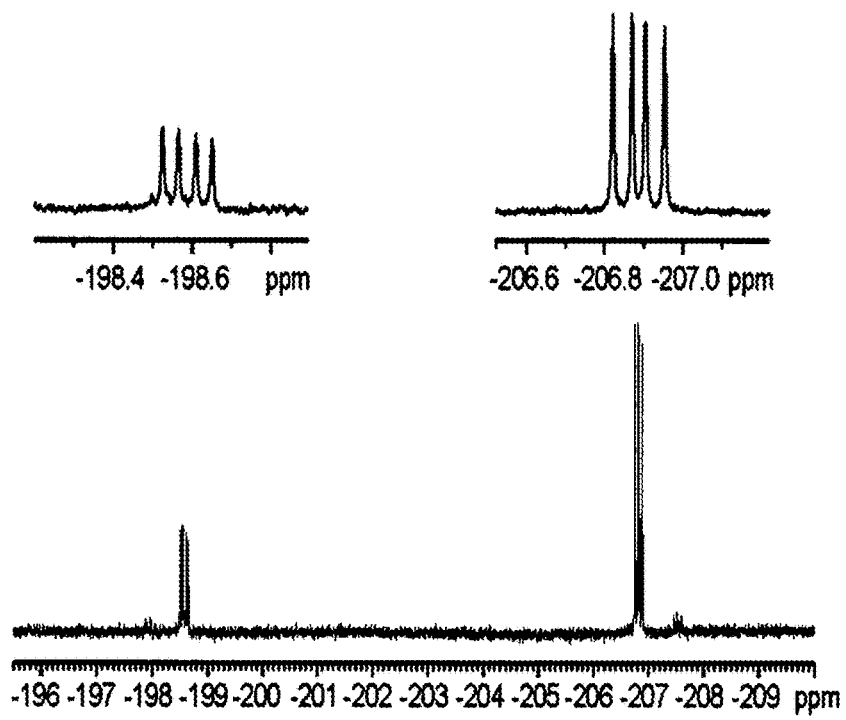
Figure 11C:
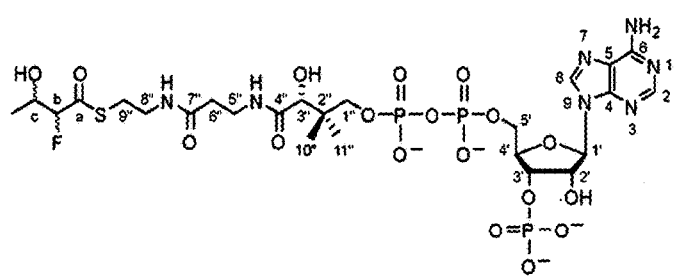
Figure 11C:
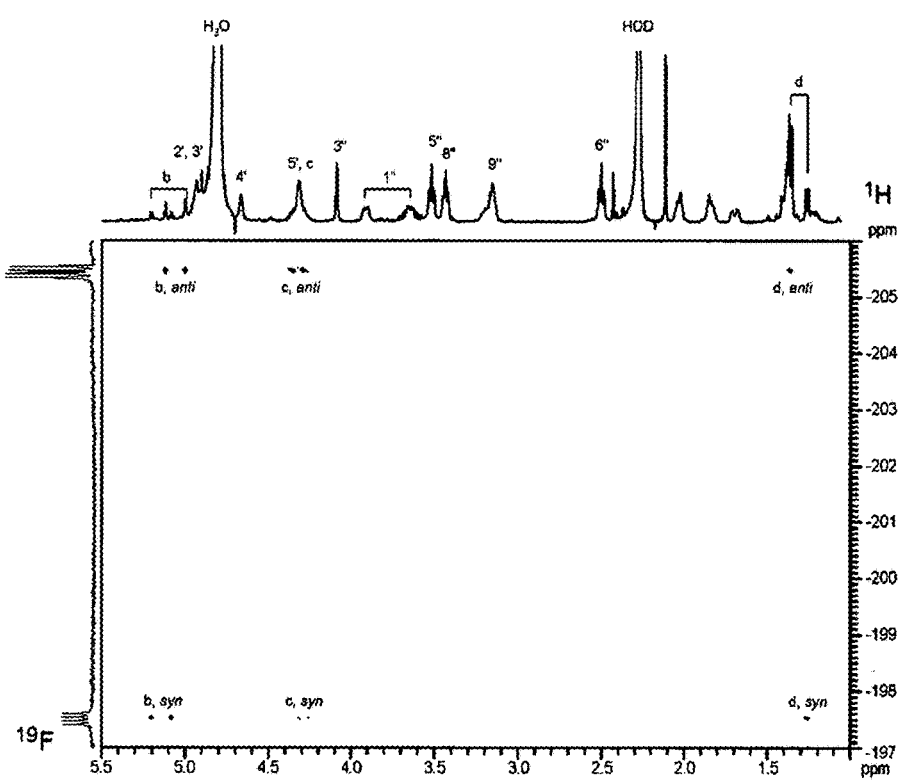

We next turned our attention to utilizing the fluoromalonyl-CoA monomer for downstream chain elongation reactions. To start, we examined the behavior of a simple polyketide synthase system with regard to one cycle of chain extension and ketoreduction, which is a key functionality of larger multimodular systems for controlling downstream cyclization and rearrangements within the polyketide backbone (FIG. 3A) (Cane, et al., Science, 282: 63-68 (1998); and Staunton, et al., Nat. Prod. Rep., 18:380-416 (2001)). We constructed a synthetic gene encoding NphT7 from Streptomyces sp. CL190 (Okamura, et al., Proc. Natl. Acad. Sci. U.S.A, 107:11265 (2010)), which appears to be a free-standing ketosynthase that is related at the structural level to the ketosynthase domain of more complex polyketide synthases (FIG. 10), and isolated the heterologously-expressed enzyme for biochemical characterization (FIG. 5). Using a coupled assay with an R-hydroxyl forming acetoacetyl-CoA reductase (PhaB), we found that NphT7 is competent to catalyze the formation of acetofluoroacetyl-CoA using an acetyl-CoA starter and fluoromalonyl-CoA extender with only a five-fold defect in catalytic efficiency (kcat/KM) derived from a drop in kcat with the fluorinated substrate (FIG. 3). This lower turnover rate observed with the fluorinated substrate is possibly related to the reduced reactivity of the enolate species, which would be stabilized by the fluorine substituent. However, the overall yield was comparable for both fluorinated and nonfluorinated substrates, which shows that a decarboxylative Claisen condensation with fluoromalonyl-CoA can take place at a similar extent of conversion compared to malonyl-CoA.

Furthermore, these experiments also show that the 2-fluoro-3-keto motif produced with the fluoromalonyl-CoA extender can be accepted by ketoreductases, as PhaB is capable of efficiently reducing the acetofluoroacetyl-CoA substrate (FIG. 11). The 1H and 19F NMR spectra of the reduced product indicate that both diastereomers are produced in this reaction (FIG. 11), which may result either from lack of stereochemical preference of NphT7 with respect to the fluorine substituent or from racemization of the product prior to reduction by PhaB. Although PhaB does not appear to show diastereoselectivity with respect to the fluorine group, the polyketide synthase ketoreductases are known to be selective with regard to their native α-substituent and could potentially carry out the stereochemical resolution of the fluorine modification upon reduction (Siskos, et al., Chem. Biol., 12:1145-1153 (2005)).

With this information in hand, we sought to extend our biosynthetic method for fluorine introduction to more complex polyketide synthase systems, which use the chain elongation reaction for the biosynthesis of many bioactive and clinically important natural products, such as erythromycin and rapamycin (Cane, et al., Science 282:63-68 (1998); and Staunton, et al., Nat. Prod. Rep. 18, 380-416 (2001)). Of the multimodular polyketide systems, 6-deoxyerythronolide B synthase (DEBS) is likely the best understood and also responsible for production of the erythromycin precursor (Khosla, et al., Annu. Rev. Biochem., 76:195-221 (2007)). We therefore focused our studies on the sixth module of DEBS, including the terminal thioesterase (DEBSMod6+TE) (Gokhale, et al., Science, 284:482-485 (1999)). Using a diketide substrate (NDK-SNAC), DEBSMod6+TE can catalyze a single round of chain elongation with its native methylmalonyl-CoA extender unit and then cyclize the tethered product to form a methyltriketide lactone (TKL)

Figure 4A:
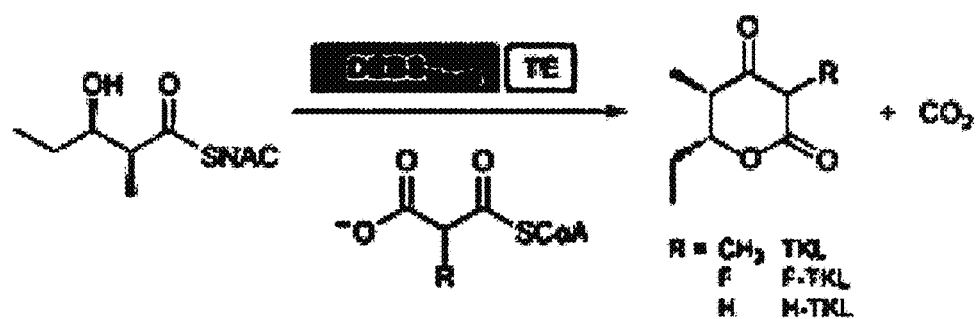
FIG. 4A-D. Production of fluorinated polyketides in vitro and in vivo by $DEBS_{Mod6}$+TE. (A) Reaction catalyzed by $DEBS_{Mod6}$+TE using the NDK-SNAC substrate with various extender units (NDK-SNAC, native diketide N-acetylcysteamine thioester, (2S,3R)-2-methyl-3-hydroxypentanoyl-N-acetylcysteamine thioester). (B) Chain extension by $DEBS_{Mod6}$+TE to form triketide lactones monitored by LC-MS (TKL, m/z=169; F-TKL, m/z=173). CoA, ATP, and ATP regeneration system are included in all in vitro reactions. Data are normalized with respect to the TKL peak. (C) Selectivity of $DEBS_{Mod6}$+TE and $DEBS_{Mod3}$+TE for methylmalonyl-CoA vs. fluoromalonyl-CoA extender unit as monitored by TKL (m/z=169) and F-TKL (m/z=173) formation. Conditions include wild-type modules, $AT^0$ modules, and $AT^0$ modules in conjunction with the trans-AT from the disorazole PKS (DszsAT). Values are reported as the mean±s.d. (n=3). (KR*, the KR domain of Mod3 is inactive). (D) LC-MS traces showing regioselective tetraketide lactone formation using the DEBS mini-PKS consisting of $DEBS_{Mod2}$ and $DEBS_{Mod3}$+TE (Me/Me, 2-methyl-4-methyl-tetraketide lactone, m/z=227; Me/F, 2-fluoro-4-methyl-tetraketide lactone, m/z=231; F/Me, 2-methyl-4-fluoro-tetraketide lactone, m/z=231). Me/Me was produced using $DEBS_{Mod2}$/$DEBS_{Mod3}$+TE and methylmalonate (1). Me/F was produced using $DEBS_{Mod2}$/$DEBS_{Mod3}AT^0$+TE, DszsAT, methylmalonyl-CoA, and fluoromalonate (2). F/Me was produced using $DEBS_{Mod2}AT^0$/$DEBS_{Mod3}$+TE, methylmalonyl-CoA, and fluoromalonate (3). Data are normalized with respect to the Me/Me peak. All reactions contained MatB and the ATP regeneration system.
Figure 4B:
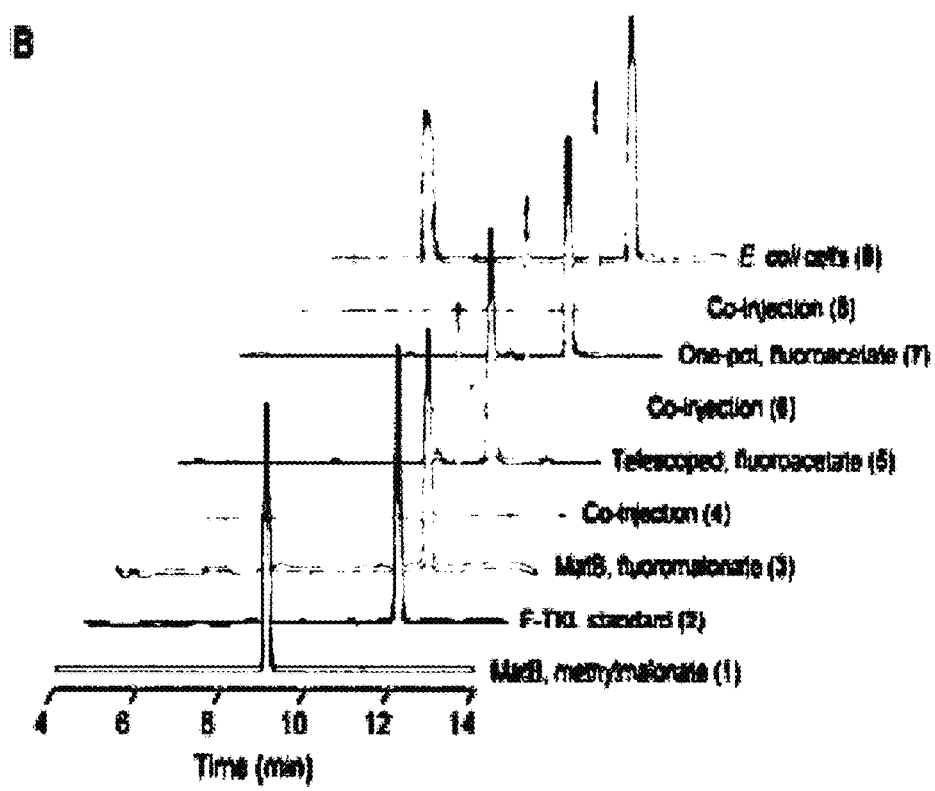
Figure 12A:
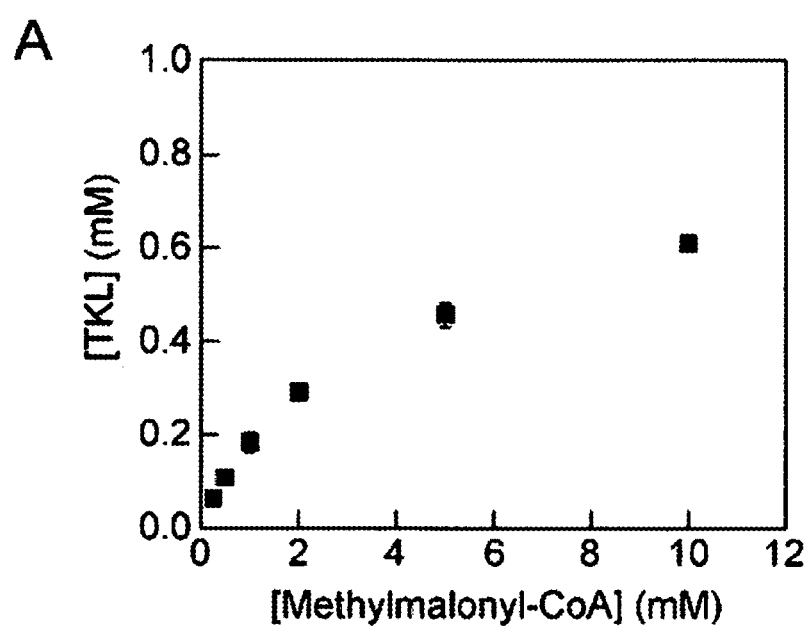
FIG. 12. Amplification of TKL formation using MatB. All reactions contained 400 mM sodium phosphate, pH 7.5, phosphoenolpyruvate (50 mM), TCEP (5 mM), magnesium chloride (10 mM), ATP (2.5 mM), pyruvate kinase (27 U/mL), myokinase (10 U/mL), methylmalonyl-CoA epimerase (5 µM), methylmalonate (20 mM), NDK-SNAC (1 mM) and DEBS$_{Mod6}$+TE (10 µM). The source of extender unit was either methylmalonyl-CoA (0.5-10 mM) or MatB (40 µM) and CoA (0.5 mM). (A) Dependence of TKL formation on methylmalonyl-CoA. Data are average±s.d. (n=3). (B) Comparison of TKL yield with and without MatB regeneration. Values are reported as the mean±s.d. (n=3).
Figure 12B:
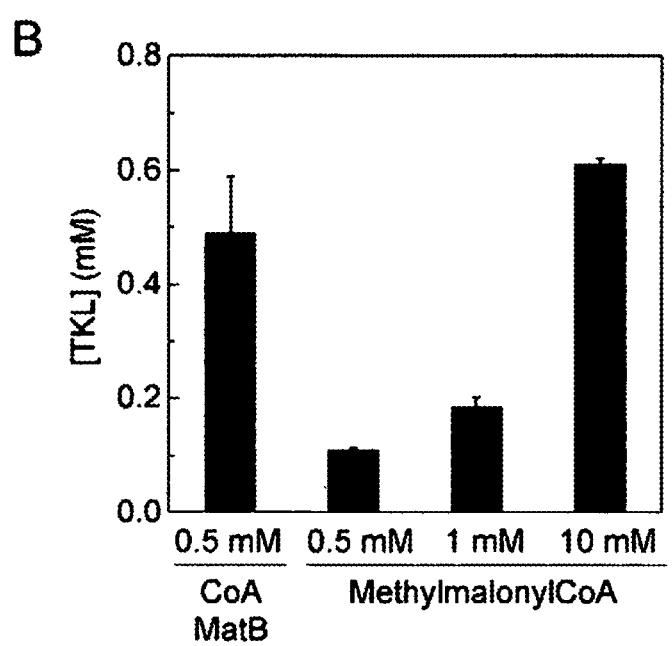
Figure 13A:
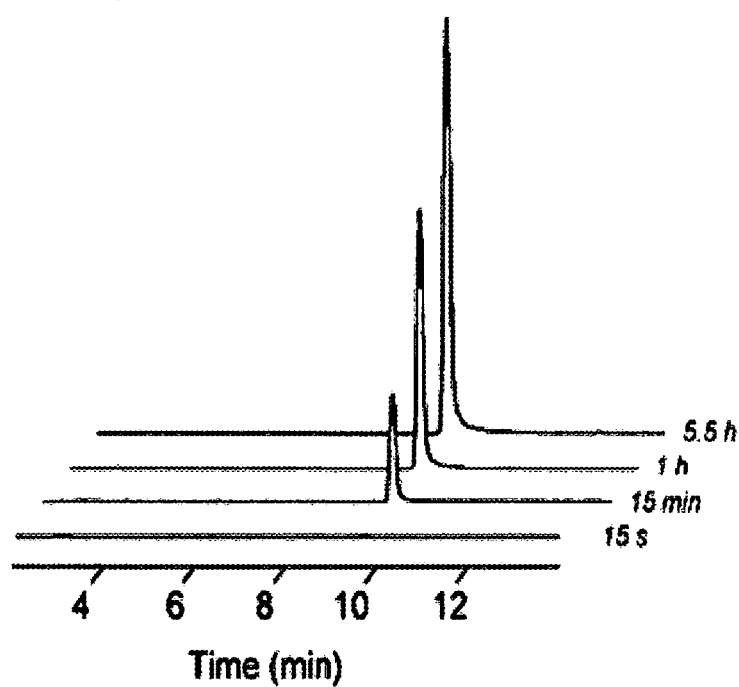
FIG. 13A-C. Time-course for TKL and F-TKL formation by DEBS$_{Mod6}$+TE with substrate regeneration. (A) LC/MS traces monitoring TKL formation (m/z 169) from 2.5 mM NDK-SNAC. (B) Plot of NDK-SNAC and TKL concentrations. Initial rate: 1.5 min$^{-1}$ (C) LC/MS traces monitoring F-TKL formation (m/z 173) from 10 mM NDK-SNAC. (D) Plot of NDK-SNAC and F-TKL concentrations. Initial rate: 0.14 h$^{-1}$. (■, NDK-SNAC; ■, TKL; ■, F-TKL).
Figure 13B:
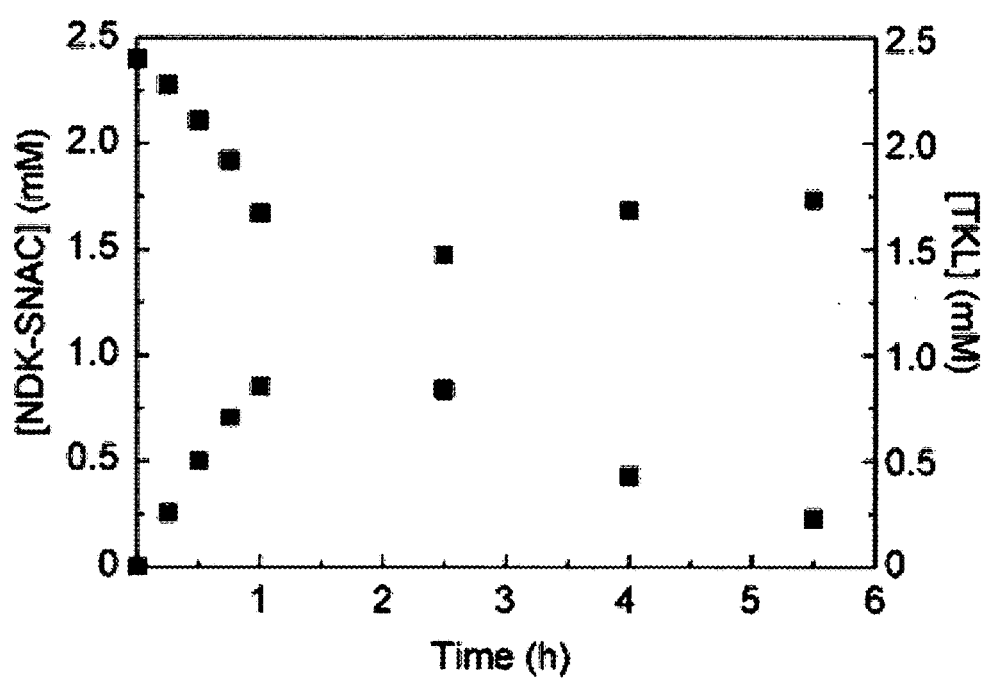
Figure 13C:
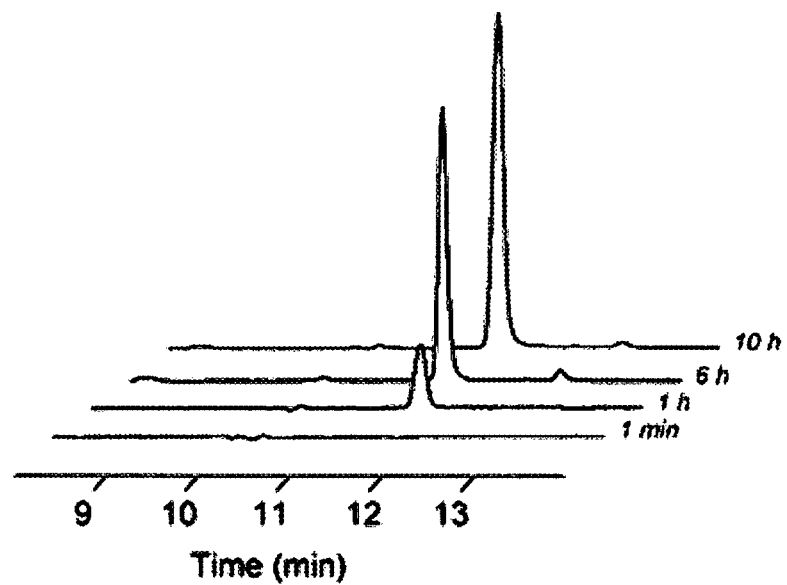
Figure 13D:
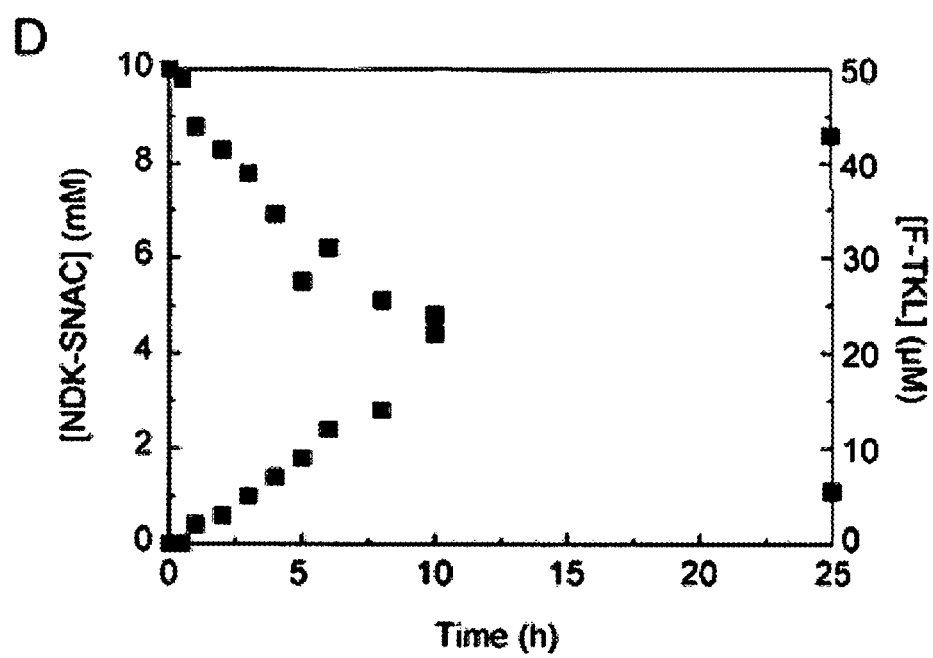

(FIG. 4A, R═CH₃; FIG. 4B, 1; FIG. 12) (Wu, et al., *J. Am. Chem. Soc.*, 122:4847-4852 (2000)). We found that DEBSMod6+TE is also able to accept the fluorinated monomer in chain extension catalysis to form the 2-fluoro-2-desmethyltriketide lactone (F-TKL) and incorporate fluorine into the polyketide backbone (FIG. 4B, 2-4; FIG. 13). The identity of the F-TKL was established by comparison to an authentic synthetic standard by reverse-phase HPLC monitored by ESI-MS and further confirmed by characterization of the isolated compound by high resolution MS, GC-MS, and 19F NMR spectroscopy (FIGS. 14-17). Although the 2S keto tautomer is generated in ≥94% diastereomeric excess (d.e.) (FIG. 16), this ratio appears to be set by the compound's stereoelectronic factors rather than the stereochemical preference of DEBSMod6+TE, as the FTKL is fully enolized in aqueous solution. The F-TKL can also be produced directly from fluoroacetate using the AckAPta/ACCase activation system in either a multi-stage (FIG. 4B, 5-6) or single-pot reaction (FIG. 4B, 7-8) with DEBSMod6+TE in a similar yield to the MatB reaction, which allows us to connect fluorinated polyketide production directly to the biosynthetically available fluorinated building block (FIG. 1A, Scheme 1).

Figure 18:
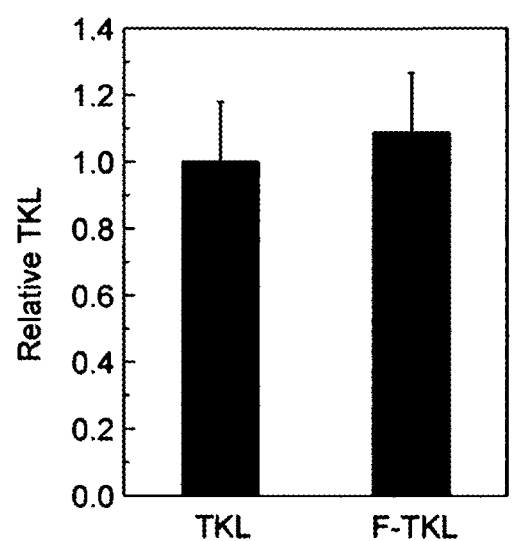
FIG. 18. Test for covalent inhibition of DEBS$_{Mod6}$+TE by fluoromalonyl-CoA. DEBS$_{Mod6}$+TE was incubated for 18 h in a F-TKL or TKL reaction. The enzyme was then isolated by Sephadex G-25 and tested for its ability to produce TKL. Values are reported as the mean±s.d. (n=3).
Figure 19:
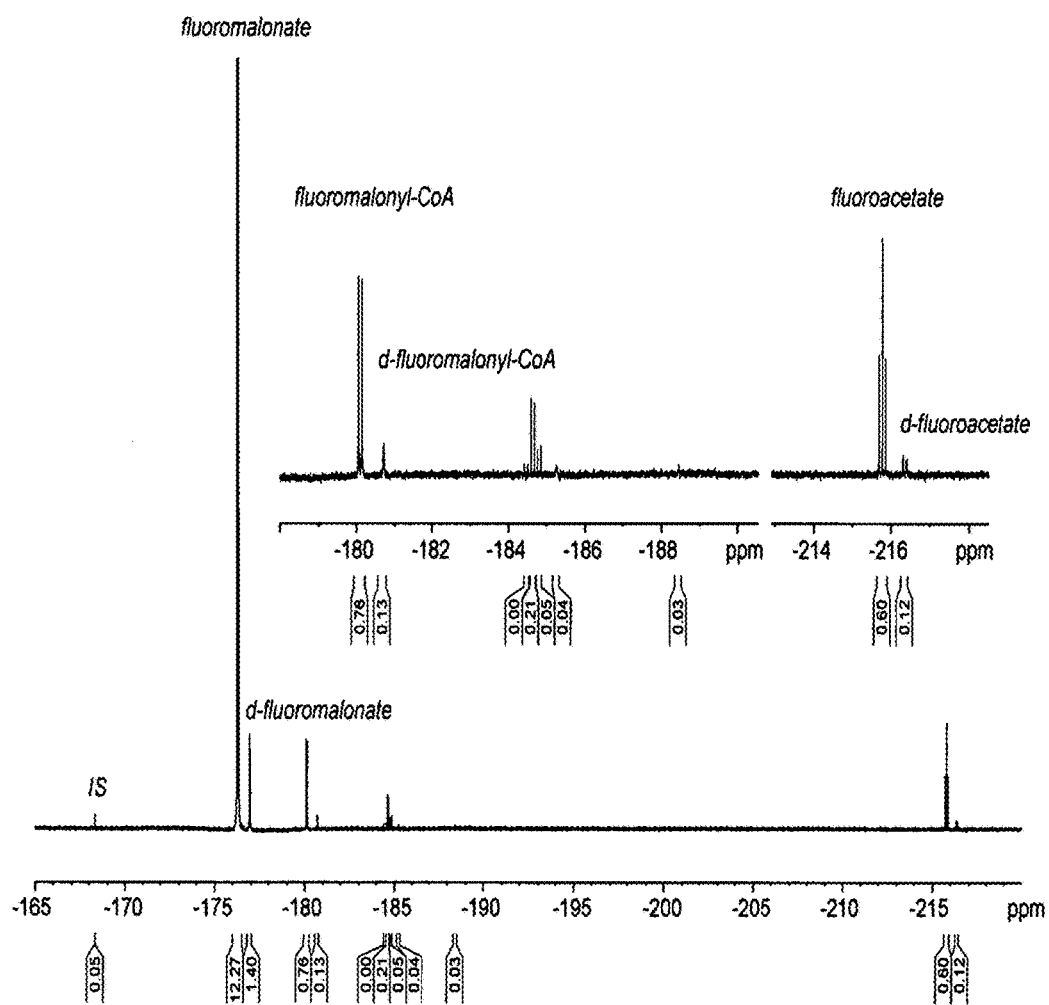
FIG. 19. $^{19}$F NMR (90% H$_2$O, 10% D$_2$O, pH 7.5) of reaction mixture for F-TKL formation by DEBS$_{Mod6}$+TE and MatB. $^{19}$F NMR analysis of the reaction mixture indicates that the major pathway for loss of fluoromalonyl-CoA appears to be hydrolysis rather than unproductive decarboxylation. In addition, no detectable defluorination was observed. (IS, 5-fluorouracil, 50 µM).

In contrast to the chain extension reaction catalyzed by NphT7, DEBSMod6+TE does not incorporate fluorinated extender units into the triketide lactone product as efficiently as its native methylmalonyl-CoA extender. Preliminary studies indicate that the reduced efficiency of DEBSMod6+TE with the fluorinated extender is not due to covalent inactivation of the enzyme (FIG. 18), but rather to the more complex biochemistry of polyketide synthases with regard to monomer selection (Bonnett, et al., *Chem. Biol.*, 18:1075-1081 (2011)). Extender unit hydrolysis, which occurs even for the native substrate (Table S2), appears to limit fluoromalonyl-CoA incorporation based on the observations that MatB and ATP are needed for fluoromalonyl-CoA regeneration and that fluoromalonate remains the major organofluorine species even in their presence (FIG. 19). The fluoromalonyl-CoA extender is however incorporated at higher efficiency by DEBSMod6+TE than malonyl-CoA (R═H), which is reported to be naturally excluded by DEBS (Liou, et al., *Biochemistry*, 42:200-207 (2002)). In fact, DEBSMod6+TE produces at least 10-fold more F-TKL than H-TKL in a direct competition experiment with equimolar amounts (1 mM) of fluoromalonyl-CoA and malonyl-CoA (Table 3).

Figure 4C:
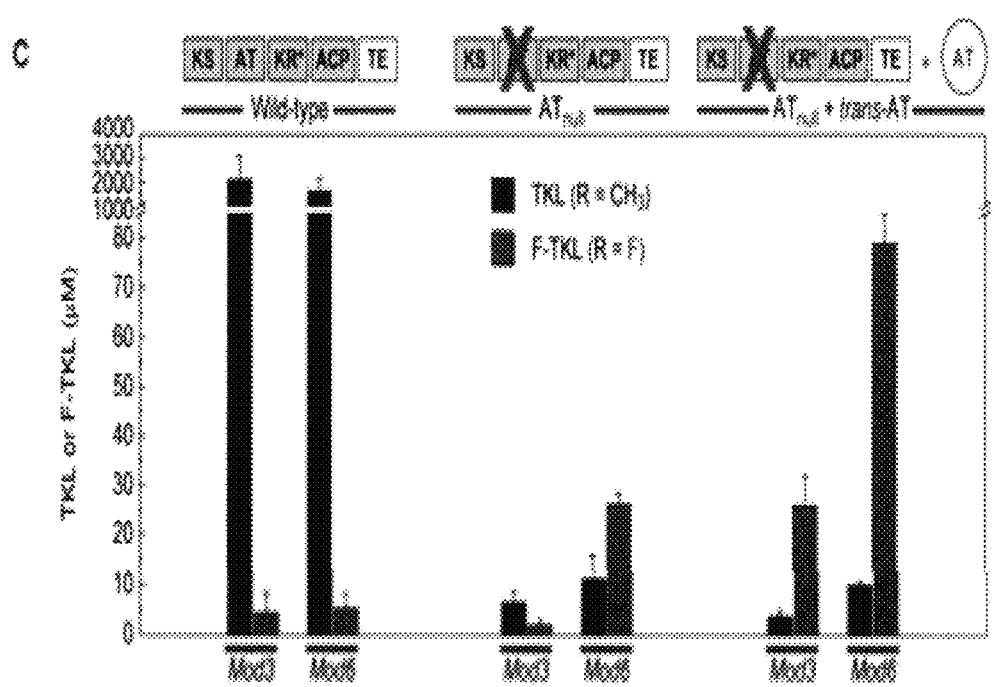

To address the issue of site- or regioselective fluorine incorporation, we turned our attention to exploiting the greater reactivity of the fluorinated extender unit towards acylation reactions. In this regard, we hypothesized that it would be possible for a fluorinated substrate to selectively acylate either the AT or ACP domains of individual DEBS modules in the presence of a catalytically compromised or inactive AT domain, an approach that has been shown to facilitate malonyl incorporation by DEBS (Kumar, et al., *J. Am. Chem. Soc.*, 125:14307-14312 (2003)). Experiments with DEBSMod6+TE showed that not only does F-TKL yield increase as expected but fluorine selectivity also improves upon introduction of a key S2107A mutation, reversing the selectivity of the wild-type module (FIG. 4C).

Figure 20:
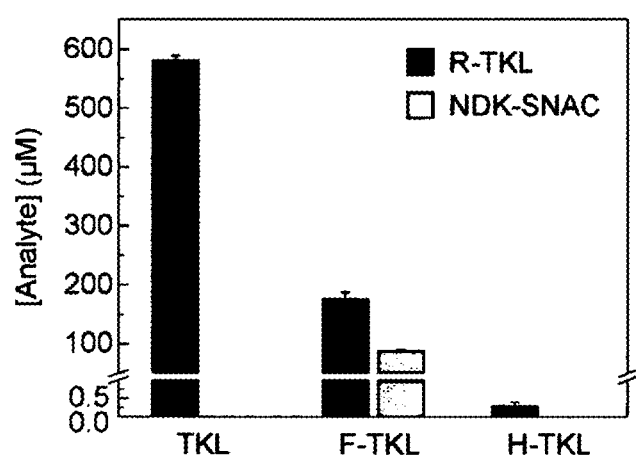
FIG. 20. R-TKL production in vitro by DEBS$_{Mod2}$/AT$^0$ under substrate regeneration conditions. When incubated overnight with NDK-SNAC (500 µM) and the methylmalonyl-CoA regenerating system, DEBS$_{Mod2}$/AT$^0$ converted all the NDK-SNAC to TKL. With the fluoromalonyl-CoA regeneration system it consumed 82% of the NDK-SNAC with 43% conversion to F-TKL. With the malonyl-CoA regeneration system it consumed 100% of the NDK-SNAC with <0.01% conversion to H-TKL. Values are reported as the mean±s.d. (n=3).

Indeed, when the NDK-SNAC substrate is used with its native module, DEBSMod2, in conjunction with the analogous S2652A mutation, extension with fluoromalonyl-CoA to form FTKL reaches 30% efficiency compared to methylmalonyl-CoA (FIG. 20). Furthermore, we found that the standalone trans-AT from the disorazole polyketide synthase (Wong, et al., *Biochemistry*, 49:95-102 (2009); and Wong, et al., *Biochemistry*, 50:6539-6548 (2011)) accepts fluoromalonyl-CoA and can further enhance F-TKL formation by the AT-null mutant (FIG. 4C). Using this approach, we began to explore the possibility of site-selective fluorine incorporation with a mini-PKS model system, consisting of DEBSMod2 and DEBSMod3+TE, that was designed to carry out two chain extension reactions from the NDK-SNAC substrate (Tsuji, et al., *Biochemistry*, 40:2326-2331 (2001)).

Figure 4D:
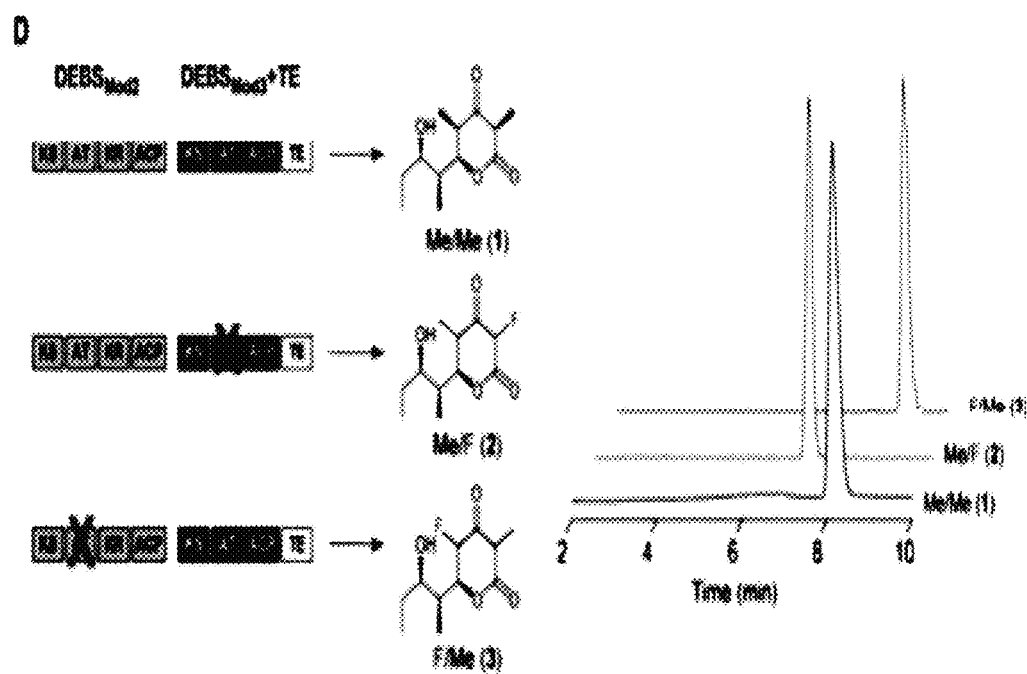
Figure 21:
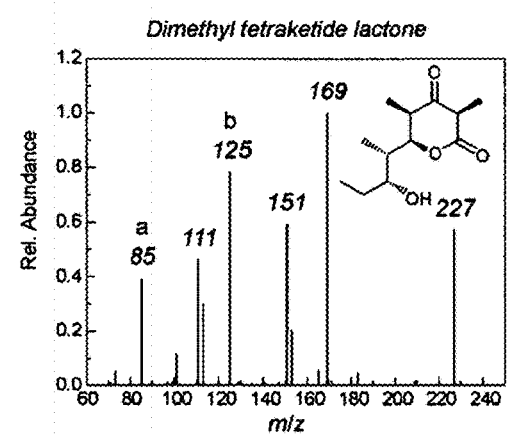
FIG. 21. ESI-MS/MS data for tetraketide lactones. Authentic standards are not available for the fluorinated compounds. Both fluorinated tetraketide lactones exhibit a mass corresponding to the loss of HF (20 amu). Fragments resulting from multiple losses were not assigned structures; however, two of these fragments (a, b) present in the dimethyl tetraketide appear to be shifted by 4 amu in the 2-fluoro-4-methyltetraketide lactone, suggesting a fluorine for methyl substitution. Furthermore, two more fragments (c, d) appear to be present in the methyl form in one of the fluorinated tetraketide lactones and the fluoro form in the other regio-isomer. These fragmentation patterns suggest the 2-fluoro-4-methyl- and the 2-methyl-4-fluoro tetraketide lactones are indeed distinct regio-isomers.
Figure 21:
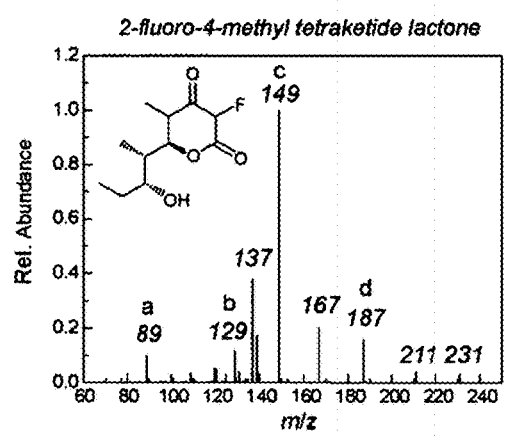
Figure 21:
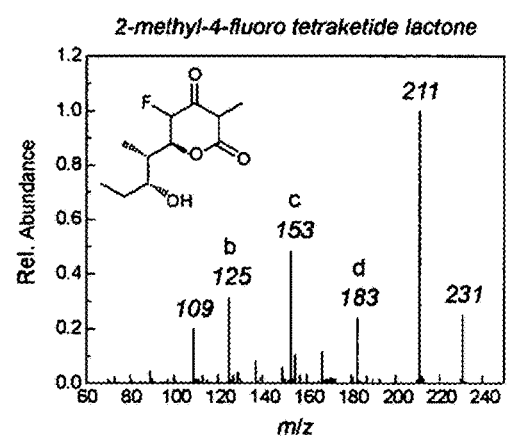

Using the appropriate AT-null constructs, we were able to observe exclusive production of either regioisomer of the fluoro-methyl tetraketide lactone (tetraKL). The identity of the 2-fluoro-4-methyl tetraKL and 2-methyl-4-fluoro tetraKL were established by both HR ESI-MS and LC-MS based on their different retention times, as well as their mass fragmentation patterns which are consistent with the incorporation of fluorine at the expected sites (FIG. 4D, FIG. 21). These studies also indicate that further chain extension after fluorine insertion can be achieved and that downstream reactions of fluorinated intermediates could potentially be tolerated. This observation is consistent with previous work that has shown that intermediates with non-native substituents, including fluorine, can be extended and tailored to the final structure (Cane, et al., *Science* 282:63-68 (1998); Mo, et al., *J. Am. Chem. Soc.*, 133:976-985 (2010); Runguphan, et al., *Proc. Natl. Acad. Sci. U.S.A.*, 106:13673-13678 (2009); Goss, et al., *ChemBioChem*, 11:698-702 (2010); Staunton, et al., *Nat. Prod. Rep.*, 18:380-416 (2001); and McDaniel, et al., *Proc. Natl. Acad. Sci. U.S.A.*, 96:1846-1851 (1999)) and gives promise that larger fluorinated polyketide targets may be accessible through this approach.

Figure 22A:
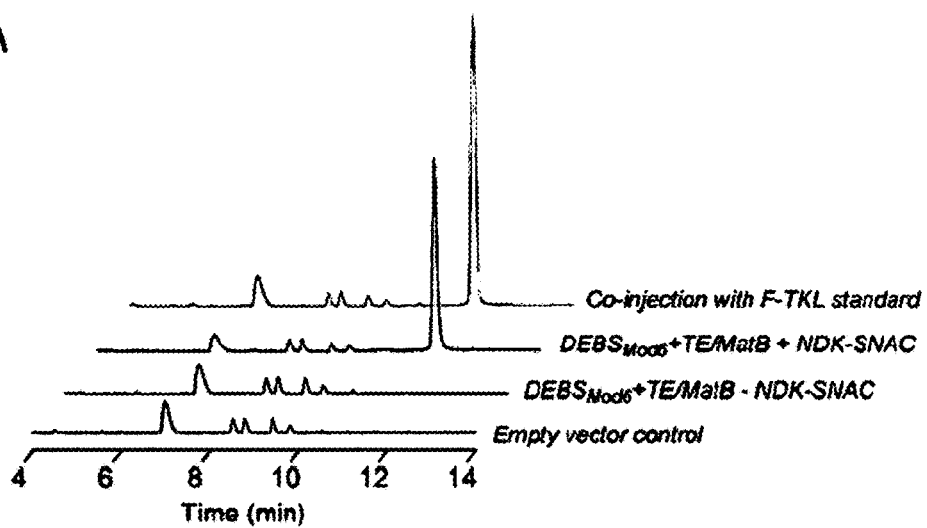
FIG. 22A-C. F-TKL production in vivo. (A) LC/MS traces showing F-TKL formation (m/z 173) in E. coli cell lysate. (B) LC/MS traces showing F-TKL formation (m/z 173) by E. coli cell culture upon feeding with NDK-SNAC. (C) In vivo selectivity data showing F-TKL production compared to H-TKL and TKL in fluoromalonate-fed E. coli resting cells expressing either DEBS$_{Mod6}$+TE or DEBS$_{Mod6}$+TE/AT$^0$ and MatB. Bars represent mean±s.d. (n=3) with individual samples marked (■ ▲ ●).
Figure 22B:
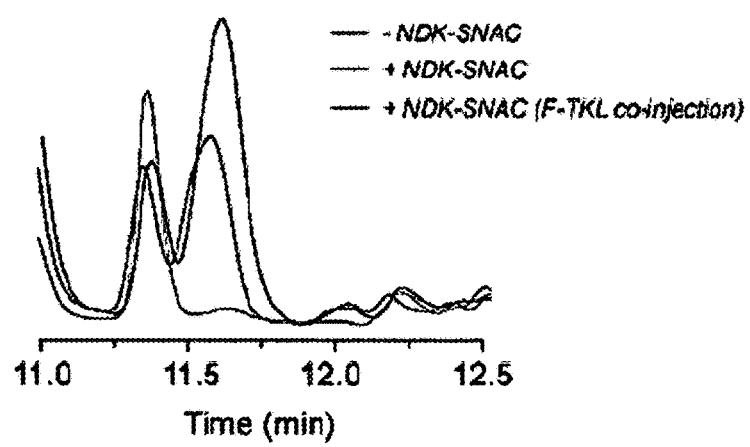
Figure 22C:
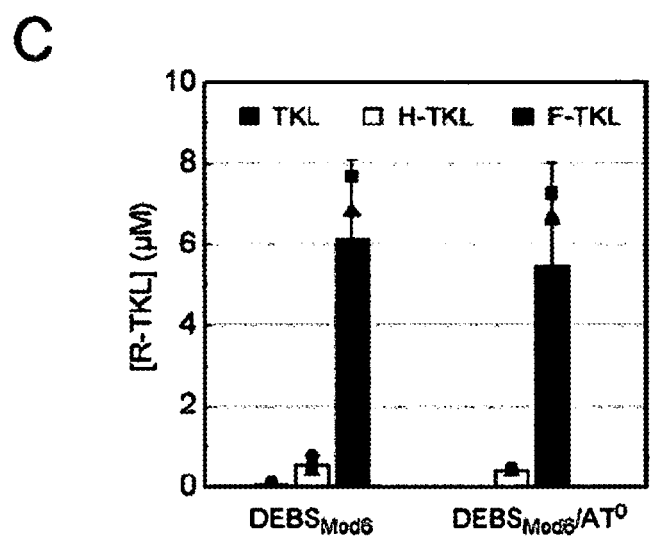
Figure 23:
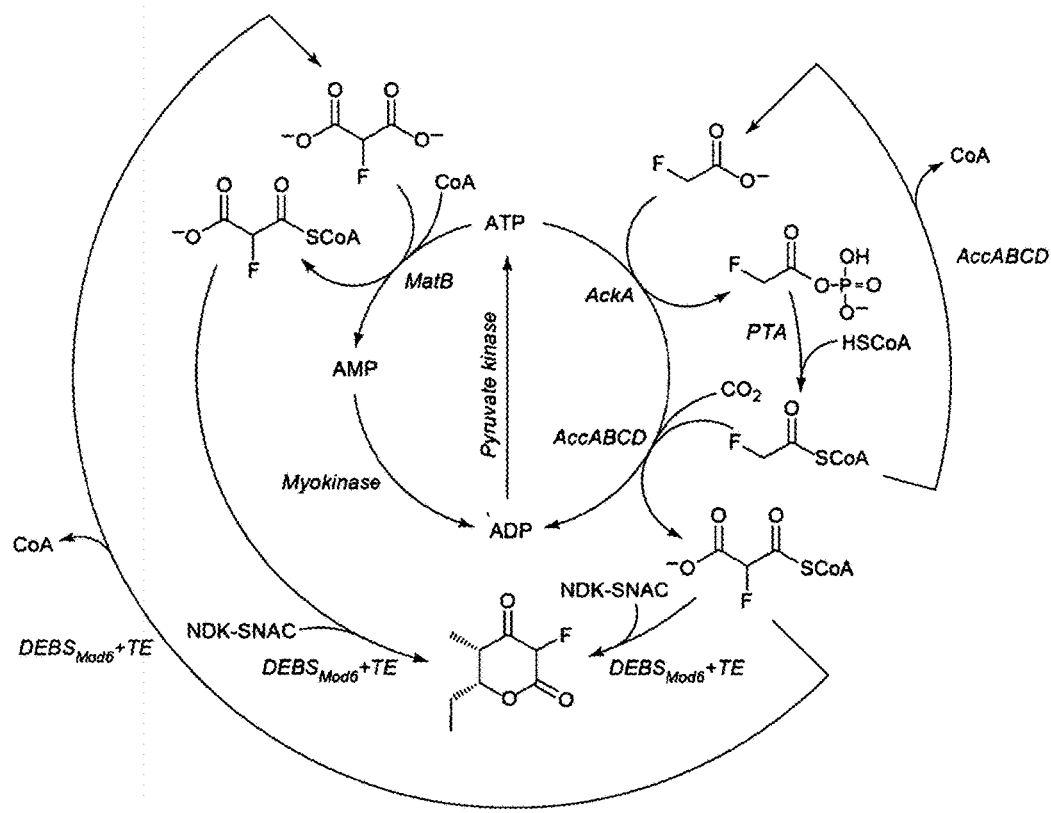
FIG. 23. Hydrolysis and regeneration reactions for F-TKL production by DEBS$_{Mod6}$+TE. Reaction scheme showing enzymes present in F-TKL forming reactions including observed non-productive hydrolysis reactions (red) and the ATP regenerating system (blue).
Figure 24:
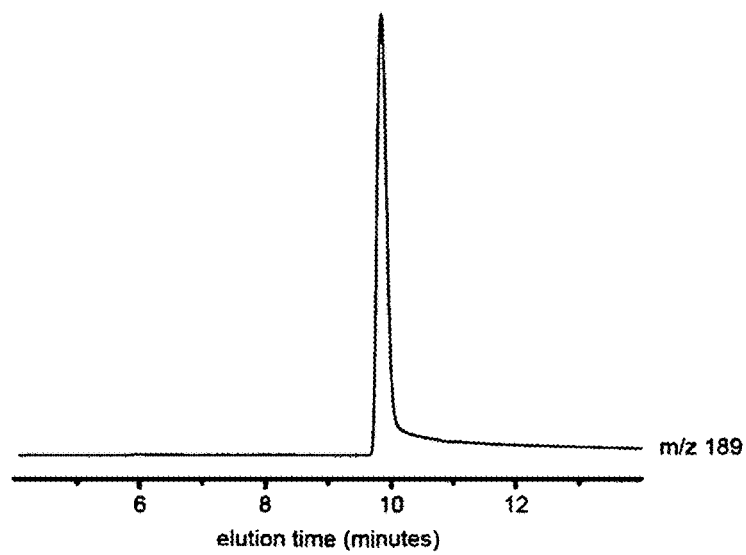
FIG. 24A-B. (A) Extracted ion LC/MS trace of enzymatic chloro-triketide product, m/z 189 (negative mode). (B) ESI mass spectrum of the peak in A. The expected isotopes are observed for 35Cl- and 37Cl-triketide.
Figure 24:
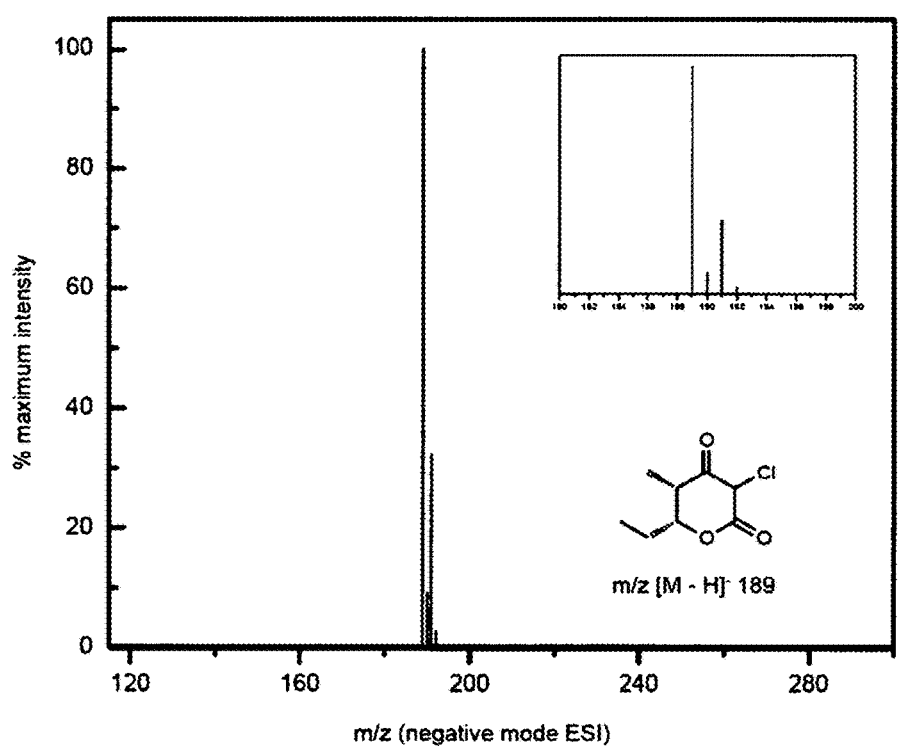
Figure 25:
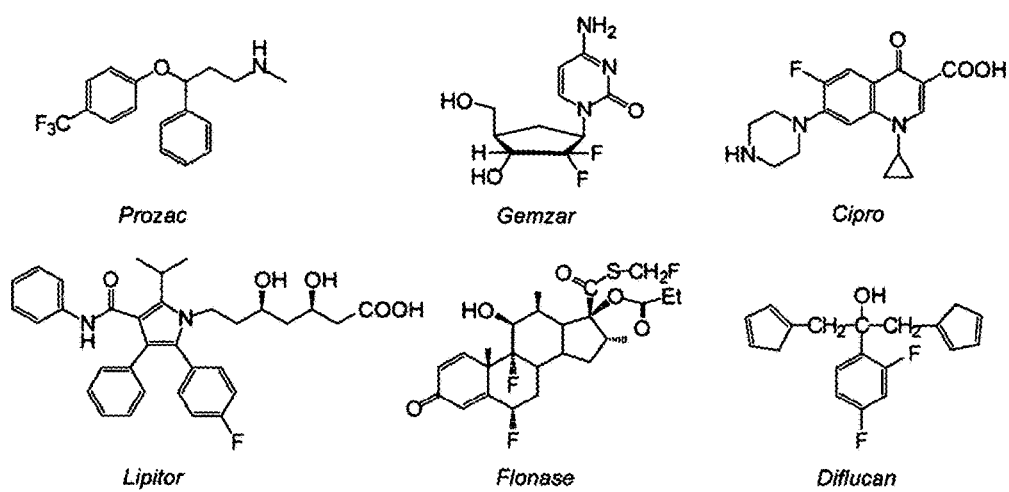
FIG. 25. Organofluorine pharmaceuticals.
Figure 26:
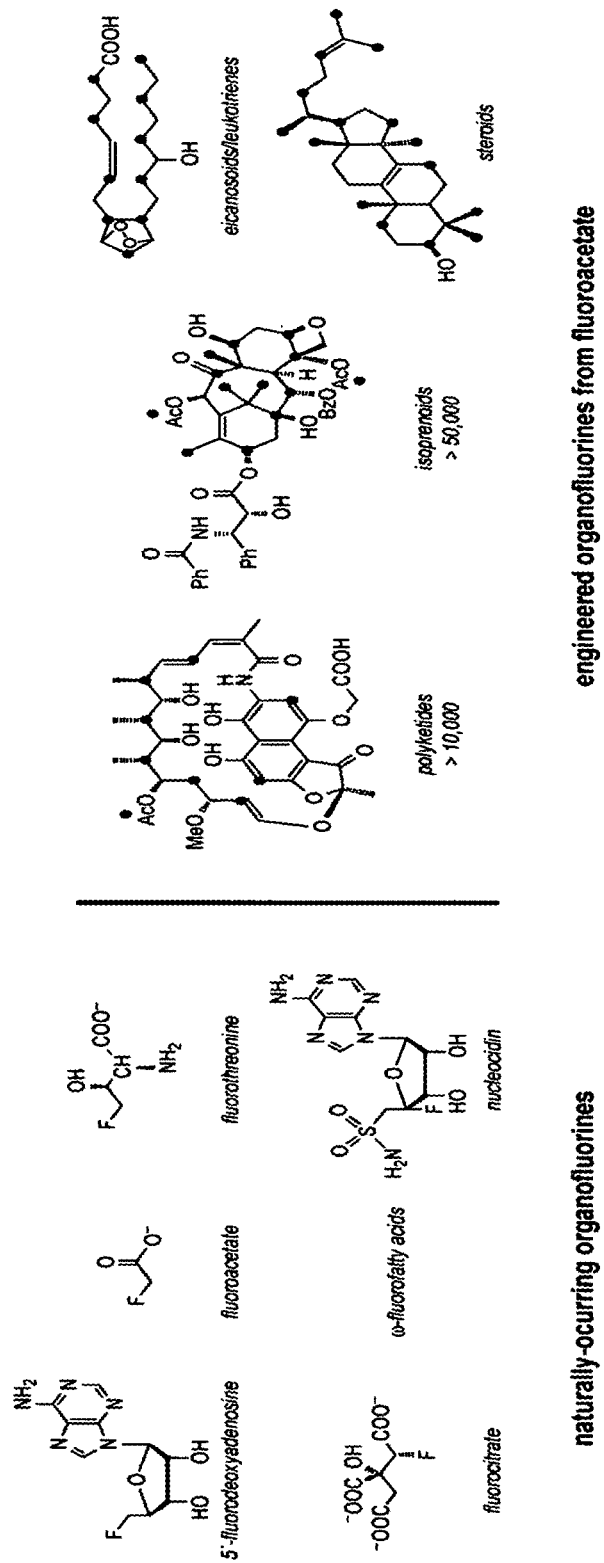
FIG. 26. Naturally-occurring organofluorines that have been identified to date are structurally simple but include highly toxic compounds such as fluoroacetate and fluorocitrate. However, by developing new downstream reactions to utilize fluoroacetate as a building block, fluorine could be incorporated site selectively into the backbones and sidechains of many large classes of modularly synthesized natural products. (Fluorination sites indicated by a red dot).

The observed selectivity for fluoromalonyl- over malonyl-CoA extender units suggested that polyketide chain extension reactions with fluoromalonyl-CoA could possibly be catalyzed in vivo in *E. coli*, which contains a significant malonyl-CoA pool (~35 µM) (Bennett, et al., *Nat. Chem. Biol.*, 5:593-599 (2009)) but almost no methylmalonyl-CoA (Haller, et al., *Biochemistry*, 39:4622-4629 (2000); and Pfeifer, et al., *Science*, 291:1790-1792 (2001)). We carried out preliminary 19F-NMR studies of cells expressing MatB, NphT7 and PhaB and fed with non-toxic levels of fluoromalonate. Analysis of the media and cell extracts indicated that flux through fluoromalonyl-CoA could reach 100 µM to 1 mM, which is sufficient for use by PKSs in live cells (Table S4). Next, we tested the ability of DEBSMod6+TE to catalyze chain elongation in cell lysates prepared from *E. coli* BAP1 coexpressing DEBSMod6+TE and MatB. Under these conditions, F-TKL is produced with no observable H-TKL upon addition of only NDK-SNAC, fluoromalonate, CoA, ATP, and the ATP regeneration system (FIG. 22A). Negative controls with either no DEBSMod6+TE/MatB expressed or no NDK-SNAC substrate show no production of F-TKL (FIG. 22A). These results demonstrate that the intracellular level of expression of the DEBSMod6+TE and MatB enzymes is sufficient for the incorporation of the fluorinated extender unit. They also further imply that fluorine could be introduced into the polyketide backbone inside living cells, which are capable of generating ATP through normal metabolic processes. We therefore cultured *E. coli* BAP1 co-expressing DEBSMod6+TE and MatB and harvested the cells after induction. These cells were then fed with the fluoromalonate precursor, which resulted in the production of FTKL upon addition of NDK-SNAC (FIG. 4B, 9; FIG. 22B). The identity of the F-TKL under these conditions were established by LC-MS, co-injection with an authentic standard, as well as high resolution MS. Moreover, F-TKL can also be produced directly in cell culture with the simple addition of a mixture of both substrates to the media after induction of DEBSMod6+TE and MatB (FIG. 22C). Taken together, these studies show that the natural selectivity of the polyketide synthase allows for the site-selective introduction of fluorine over hydrogen into the polyketide backbone inside living cells.

Example 3

Preparation of chloromalonate. Diethylchloromalonate (Sigma-Aldrich; 0.5 mL, 3.1 mmol) was saponified with methanolic sodium hydroxide (2 M, 3.5 mL) in dichloromethane and methanol (9:1 v/v, 32 mL). The mixture was concentrated in vacuo and the residue dissolved in water, washed with diethyl ether, then acidified to pH~2 with HCl and extracted with ethyl acetate. The combined organic layers were dried (MgSO4), filtered and concentrated, and the residue dissolved in 1.5 M NaOH to give a 1 M solution of sodium chloromalonate.

Chlorotriketide formation. The assay mixture contained 400 mM sodium phosphate, pH 7.5, phosphoenolpyruvate (50 mM), TCEP (5 mM), magnesium chloride (10 mM), ATP (2.5 mM), pyruvate kinase (27 U/mL), myokinase (10 U/mL), CoA (1 mM), methylmalonyl-CoA epimerase (5 µM), MatB (40 µM) and chloromalonate (10 mM). This mixture was incubated at 37° C. for 45 min and then initiated by addition of the N-acetylcysteamine thioester of (2S,3R)-2-methyl-3-hydroxypentanoic acid (NDK-SNAC, 5 mM) and DEBSMod3+TE/AT0 (10 µM). Aliquots (35 µL) were removed and quenched by addition of 70% perchloric acid (1.75 µL). Samples were centrifuged at 18,000×g to pellet the precipitated protein. The supernatant (33 µL) was removed and excess salts were precipitated by freezing in liquid nitrogen and centrifuging at 18,000×g until thawed. The supernatant was removed and analyzed on a Zorbax Eclipse XDB C-18 column (3.5 µm, 3×150 mm, 35° C., Agilent) using a linear gradient from 0 to 40% acetonitrile over 14 min with 0.1% formic acid as the aqueous mobile phase after an initial hold at 0% acetonitrile for 30 s (0.8 mL/min) The product was monitored using an Agilent G1315D diode array detector (255 nm) and an Agilent 6130 single quadruple mass spectrometer operating in negative ion mode ([M–H]– m/z 189).

Published resources cited herein are incorporated by reference herein for their respective teachings of standard laboratory methods found therein. Such incorporation, at a minimum, is for the specific teaching and/or other purpose that may be noted when citing the reference herein. If a specific teaching and/or other purpose is not so noted, then the published resource is specifically incorporated for the teaching(s) indicated by one or more of the title, abstract, and/or summary of the reference. If no such specifically identified teaching and/or other purpose may be so relevant, then the published resource is incorporated in order to more fully describe the state of the art to which the present invention pertains, and/or to provide such teachings as are generally known to those skilled in the art, as may be applicable. However, it is specifically stated that a citation of a published resource herein shall not be construed as an admission that such is prior art to the present invention. Also, in the event that one or more of the incorporated published resources differs from or contradicts this application, including but not limited to defined terms, term usage, described techniques, or the like, this application controls. Subject matter in the Examples is incorporated into this section to the extent not already present.

While various embodiments of the present invention have been shown and described herein, it is emphasized that such embodiments are provided by way of example only. Numerous variations, changes and substitutions may be made without departing from the invention herein in its various embodiments. Specifically, and for whatever reason, for any grouping of compounds, nucleic acid sequences, polypeptides including specific proteins including functional enzymes, metabolic pathway enzymes or intermediates, elements, or other compositions, or concentrations stated or otherwise presented herein in a list, table, or other grouping (such as metabolic pathway enzymes shown in a figure), unless clearly stated otherwise, it is intended that each such grouping provides the basis for and serves to identify various subset embodiments, the subset embodiments in their broadest scope comprising every subset of such grouping by exclusion of one or more members (or subsets) of the respective stated grouping. Moreover, when any range is described herein, unless clearly stated otherwise, that range includes all values therein and all sub-ranges therein. Accordingly, it is intended that the invention be limited only by the spirit and scope of appended claims, and of later claims, and of either such claims as they may be amended during prosecution.

What is claimed is:

1. An enzymatically mediated method for producing a halogenated ketide, said method comprising:
   (a) a first condensation reaction comprising contacting a polyketide synthase and a substrate for the polyketide synthase with a compound according to Formula I:

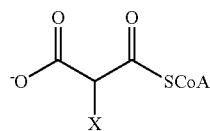

in which X is a member selected from F, Cl, Br and I,
   wherein said polyketide catalyzes the condensation and the contacting is under conditions appropriate for the condensation.

2. The method according to claim 1, further comprising:
   (b) prior to (a), contacting a precursor compound according to Formula II:

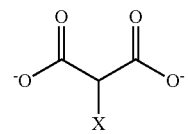

in which X is a member selected from F, Cl, Br and I,
   with one or more enzyme to ligate Co-A onto a carboxyl moiety of the compound according to Formula II under conditions appropriate for the ligation, thereby producing a compound according to Formula I.

3. The method according to claim 1, wherein the halogenated ketide comprises at least one subunit of a 2-halo-3-keto motif.

4. The method according to claim 2, wherein the at least one enzyme is a member selected from malonyl-CoA synthetase (MatB), acetate kinase, acyl-CoA synthase, phosphotransacetylase, acetyl coenzyme A carboxylase, and a combination thereof.

5. The method according to claim 1, wherein said polyketide synthesase is selected from naturally occuring and non-naturally occurring polyketide synthases.

6. The method of claim 1 wherein said polyketide synthase is deoxyerythronolide B synthase.

7. The method according to claim 1 wherein said polyketide synthase is expressed within a host microorganism, and said polyketide synthase performs the condensation within the host microorganism.

8. The method according to claim 7, wherein said host microorganism is fed a non-toxic amount of a compound according to Formula II:

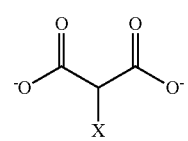

(II)

in which X is a member selected from F, Cl, Br and I.

9. The method according to claim 7, wherein said host microorganism converts said compound according to Formula II:

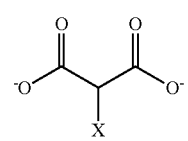

(II)

in which X is a member selected from F, Cl, Br and I, into said compound according to Formula I.

10. The method according to claim 7, wherein said host microorganism converts said compound according to Formula III:

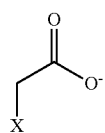

(III)

into said compound according to Formula II:

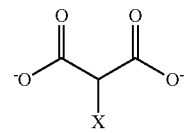

(II)

in which X is a member selected from F, Cl, Br and I.

11. The method according to claim 8, wherein said host microorganism expresses an enzyme selected from acetate kinase, phosphotransacetylase, acetyl coenzyme A carboxylase and a combination thereof.

12. The method according to claim 9, wherein each of said malonyl-CoA sythetase (MatB), acetate kinase, phosphotransacetylase, acyl-CoA synthase, acetyl coenzyme A carboxylase is independently selected from naturally occuring and non-naturally occuring enzymes.

13. The method according to claim 9, wherein said acetyl coenzyme A carboxylase comprises a subunit selected from AccABCD, AccA2, and PccBE.

14. The method according to claim 1, further comprising carrying out a second condensation subsequent to said first condensation reaction, wherein said halogenated ketide is said substrate.

15. The method according to claim 3, wherein the subunit of 2-halo-3-keto motif is reduced by a ketoreductase.

16. The method according to claim 1, further comprising (c), dehydrating the product of step (a).

17. The method according to claim 16, further comprising (d), submitting the product of (c) to an enoyl reduction.

18. The method according to claim 1, further comprising (e), prior to (a), transferring a halomalonyl subunit from a compound according to Formula I onto a polyketide synthase through action of trans-acyl transferase.

19. A host microorganism cell comprising a non-toxic amount of a molecule selected from Formula I:

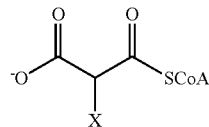

(I)

and
Formula II:

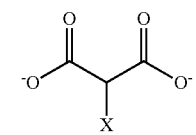

(II)

in which X is a member selected from F, Cl, Br and I, and a combination thereof within the cell.

* * * * *